(12) United States Patent
Kastelein et al.

(10) Patent No.: US 12,157,773 B2
(45) Date of Patent: *Dec. 3, 2024

(54) IL27RALPHA BINDING MOLECULES AND METHODS OF USE

(71) Applicant: Synthekine, Inc., Menlo Park, CA (US)

(72) Inventors: Robert Kastelein, Menlo Park, CA (US); Deepti Rokkam, Menlo Park, CA (US); Patrick J. Lupardus, Menlo Park, CA (US); Sandro Vivona, Redwood City, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/006,370

(22) PCT Filed: Aug. 4, 2021

(86) PCT No.: PCT/US2021/044576
§ 371 (c)(1),
(2) Date: Jan. 20, 2023

(87) PCT Pub. No.: WO2022/031870
PCT Pub. Date: Feb. 10, 2022

(65) Prior Publication Data
US 2023/0295314 A1    Sep. 21, 2023

Related U.S. Application Data

(60) Provisional application No. 63/135,884, filed on Jan. 11, 2021, provisional application No. 63/078,745, filed on Sep. 15, 2020, provisional application No. 63/061,562, filed on Aug. 5, 2020.

(51) Int. Cl.
| | | |
|---|---|---|
| *C07K 14/715* | (2006.01) | |
| *A61P 37/02* | (2006.01) | |
| *C07K 16/28* | (2006.01) | |
| *C07K 16/46* | (2006.01) | |
| *C07K 19/00* | (2006.01) | |
| *C12N 15/63* | (2006.01) | |
| *C12N 15/86* | (2006.01) | |
| *A61K 39/00* | (2006.01) | |

(52) U.S. Cl.
CPC .......... *C07K 16/2866* (2013.01); *A61P 37/02* (2018.01); *C07K 14/7155* (2013.01); *C07K 16/2803* (2013.01); *C07K 16/46* (2013.01); *C07K 16/468* (2013.01); *C07K 19/00* (2013.01); *C12N 15/63* (2013.01); *C12N 15/86* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/569* (2013.01); *C07K 2319/40* (2013.01)

(58) Field of Classification Search
CPC ............ C07K 16/2866; C07K 2317/22; C07K 2317/24; C07K 2317/622; C07K 2317/62; C07K 16/46; C07K 2317/31; C07K 2317/569; A61K 2039/505; A61K 39/3955
See application file for complete search history.

(56) References Cited

U.S. PATENT DOCUMENTS

| | | |
|---|---|---|
| 8,258,268 B2 | 9/2012 | Wu et al. |
| 8,921,528 B2 | 12/2014 | Holt et al. |
| 8,975,382 B2 | 3/2015 | Revets et al. |
| 9,334,331 B2 | 5/2016 | Igawa et al. |
| 10,421,807 B2 | 9/2019 | Gonzales et al. |
| 10,927,186 B2 | 2/2021 | Roobrouck et al. |
| 11,873,349 B1 | 1/2024 | Kastelein et al. |
| 2006/0024295 A1 | 2/2006 | Brunetta |
| 2010/0297127 A1 | 11/2010 | Ghilardi et al. |
| 2011/0028695 A1 | 2/2011 | Revets et al. |
| 2011/0053865 A1* | 3/2011 | Saunders ............... A61P 35/00 536/23.1 |
| 2011/0142831 A1 | 6/2011 | Cua et al. |
| 2012/0201746 A1 | 8/2012 | Liu et al. |
| 2012/0316324 A1 | 12/2012 | Adams et al. |
| 2013/0189262 A1 | 7/2013 | Wong et al. |
| 2014/0065142 A1 | 3/2014 | Roschke et al. |
| 2015/0079088 A1 | 3/2015 | Lowman et al. |
| 2016/0046730 A1 | 2/2016 | Ghayur et al. |

(Continued)

FOREIGN PATENT DOCUMENTS

| | | |
|---|---|---|
| CN | 111018985 A | 6/2019 |
| WO | 2008/011081 A2 | 1/2008 |

(Continued)

OTHER PUBLICATIONS

Bhattacharya et al. Impact of genetic variation on three dimensional structure and function of proteins. PLoS One 12(3): e0171355, 2017.*

(Continued)

*Primary Examiner* — Bridget E Bunner
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human IL27Rα, compositions comprising such antibodies, and methods of use thereof.

53 Claims, No Drawings
Specification includes a Sequence Listing.

(56) References Cited

U.S. PATENT DOCUMENTS

| | | | |
|---|---|---|---|
| 2016/0251440 | A1 | 9/2016 | Roobrouck et al. |
| 2017/0106051 | A1 | 4/2017 | Oh et al. |
| 2017/0298149 | A1 | 10/2017 | Baeuerle et al. |
| 2018/0362655 | A1 | 12/2018 | Wang et al. |
| 2019/0185562 | A1 | 6/2019 | Gromada et al. |
| 2019/0330366 | A1* | 10/2019 | Eckelman .......... C07K 16/2827 |
| 2019/0352404 | A1 | 11/2019 | Xu et al. |
| 2019/0382500 | A1 | 12/2019 | Abujoub et al. |
| 2020/0016202 | A1 | 1/2020 | Kuchroo et al. |
| 2020/0055946 | A1* | 2/2020 | Timmer ................ A61K 35/17 |
| 2020/0157237 | A1 | 5/2020 | Regev et al. |

FOREIGN PATENT DOCUMENTS

| | | |
|---|---|---|
| WO | 2009/068631 A1 | 6/2009 |
| WO | 2013/006544 A1 | 1/2013 |
| WO | 2013/059299 A1 | 4/2013 |
| WO | 2015/142675 A2 | 9/2015 |
| WO | 2016/097313 A1 | 6/2016 |
| WO | 2017/198212 A1 | 11/2017 |
| WO | 2019/129221 A1 | 7/2019 |
| WO | 2019/242632 A1 | 12/2019 |
| WO | 2020/144164 A1 | 7/2020 |
| WO | 2020/187711 A1 | 9/2020 |
| WO | 2022031871 A1 | 2/2022 |
| WO | 2022055641 A2 | 3/2022 |

OTHER PUBLICATIONS

Bork, P. Powers and pitfalls in sequence analysis: the 70% hurdle. Genome Res 10: 398-400, 2000.*

Bork, P. Go hunting in sequence databases but watch out for the traps. Trends in Genetics 12(10): 425-427, 1996.*

Brenner. S.E. Errors in genome annotation. Trends in Genetics 15:132-133, 1999.*

Brorson et al. Mutational analysis of avidity and fine specificity of anti-levan antibodies. J Immunol 163: 6694-6701, 1999.*

Brummell et al. Probing the combining site of an anti-carbohydrate antibody by saturation-mutagenesis: role of the heavy-chain CDR3 residues. Biochem 32(4): 1180-1187, 1993.*

Burks et al. In vitro scanning saturation mutagenesis of an antibody binding pocket. Proc Natl Acad Sci USA 94: 412-417, 1997.*

Colman Research in Immunol. 145:33-36, 1994.*

Doerks et al. Protein annotation: detective work for function prediction. Trends in Genetics 14:248-250, 1998.*

Fenton et al. Rheostat positions: a new classification of protein positions relevant to pharmacogenomics. Medicinal Chem Res 29: 1133-1146, 2020.*

Guo et al. Protein tolerance to random amino acid change. Proc Natl Acad Sci USA 101(25): 9205-9210, 2004.*

Ikeuchi et al. Delicate balance among thermal stability, binding affinity, and conformational space explored by single-domain VHH antibodies. Sci Reports 11: 20624, 2021 (9 total pages).*

Jang et al. The structural basis for DNA binding by an anti-DNA autobody. Mol Immunol 35: 1207-1217, 1998.*

Kobayashi et al. Tryptophan H33 plays an important role in pyrimidine (6-4) pyrimidone photoproduct binding by a high-affinity antibody. Protein Engineering 12(10): 879-884, 1999.*

Rudikoff et al. Single amino acid substitution altering antigenbinding specificity. Proc Natl Acad Sci USA 79: 1979-1983, 1982.*

Skolnick et al. From genes to protein structure and function: novel applications of computational approaches in the genomic era. Trends Biotechnol 18(I):34-39 2000.*

Smith et al. The challenges of genome sequence annotation or "the devil is in the details". Nature Biotechnol 15: 1222-1223, 1997.*

Tokuriki et al. Stability effects of mutations and protein evolvability. Curr Opin Structural Biol 19: 596-604, 2009.*

Vasudevan et al. A single amino acid change in the binding pocket alters specificity of an anti-integrin antibody AP7.4 as revealed by its crystal structure. Blood Cells Mol Diseases 32: 176-181, 2004.*

Zhang et al. Comprehensize optimization of a single-chain variable domain antibody fragment as a targeting ligand for a cytotoxic nanoparticle. mAbs 7(1): 42-52, 2015.*

International Search Report in PCT/US2021/044576, mailed Jan. 12, 2022, 12 pages.

U.S. Appl. No. 18/019,042, filed Aug. 5, 2021, Kastelein et al.

U.S. Appl. No. 18/164,386, filed Feb. 3, 2023, Kastelein et al..

Cairo, et al. "Control of multivalent interactions by binding epitope density." Journal of the American Chemical Society 124, No. 8 (2002): 1615-1619.

De Weerd, et al. "The interferons and their receptors—distribution and regulation." Immunology and cell biology 90, No. 5 (2012): 483-491.

Fan, et al. "Bispecific antibodies and their applications." Journal of hematology & oncology 8 (2015): 1-14.

Heldin, Carl-Henrik. "Dimerization of cell surface receptors in signal transduction." Cell 80, No. 2 (1995): 213-223.

Holliger, et al. ""Diabodies": small bivalent and bispecific antibody fragments." Proceedings of the National Academy of Sciences 90, No. 14 (1993): 6444-6448.

Kontermann, Roland. "Dual targeting strategies with bispecific antibodies." In MAbs, vol. 4, No. 2, pp. 182-197. Taylor & Francis, 2012.

Nie, et al. "Biology drives the discovery of bispecific antibodies as innovative therapeutics." Antibody therapeutics 3, No. 1 (2020): 18-62.

Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

Saerens, et al. "Single-domain antibodies as building blocks for novel therapeutics." Current opinion in pharmacology 8, No. 5 (2008): 600-608.

Shahangain et al., VVH Against VEGF-RBD, Genbank entry (online) National Center for Biotechnology Information, May 12, 2015, retrieved from the internet www.ncbi.nlm.nih.gov/protein/BAR73350.1, 2 pages.

Shouval, et al. "Interleukin 10 receptor signaling: master regulator of intestinal mucosal homeostasis in mice and humans." Advances in immunology 122 (2014): 177-210.

U.S. Appl. No. 18/164,386, Non-Final Office Action, Mailed on Jul. 25, 2023, 25 pages.

U.S. Appl. No. 18/164,386, Notice of Allowance, Mailed on Aug. 25, 2023, 10 pages.

U.S. Appl. No. 18/464,998, filed Sep. 11, 2023, specification and drawings.

Akbar et al., "A Compact Vocabulary of Paratope-Epitope Interactions Enables Predictability of Antibodyantigen Binding", Cell Reports, vol. 34, 108856, Mar. 16, 2021, 21 pages.

Deweerd, "The Interferons and Their Receptors Distribution and Regulation", Immunology and Cell Biology, vol. 90, No. 5, May 2012, pp. 483-491.

Edwards et al., "The Remarkable Flexibility of the Human Antibody Repertoire; Isolation of Over One Thousand Different Antibodies to a Single Protein, BLyS", Journal of Molecular Biology, vol. 334, No. 1, Nov. 14, 2003, pp. 103-118.

Goel et al., "Plasticity Within the Antigen-Combining Site May Manifest as Molecular Mimicry in the Humoral Immune Response", The Journal of Immunology, vol. 173, No. 12, Dec. 2004, pp. 7358-7367.

Khan et al., "Adjustable Locks and Flexible Keys: Plasticity of Epitope-Paratope Interactions in Germline Antibodies", The Journal of Immunology, vol. 192, Issue 11, 2014, pp. 5398-5405.

Lloyd et al., "Modelling the Human Immune Response: Performance of a 1011 Human Antibody Repertoire Against a Broad Panel of Therapeutically Relevant Antigens", Protein Engineering, Design and Selection, vol. 22, No. 3, Mar. 2009, pp. 159-168.

Lo et al., "Conformational Epitope Matching and Prediction Based on Protein Surface Spiral Features", BMC Genomics, vol. 22, May 31, 2021, pp. 1-16.

Marks et al., "How Repertoire Data are Changing Antibody Science", Journal of Biological Chemistry, vol. 295, No. 29, Jul. 17, 2020, pp. 9823-9837.

(56) References Cited

OTHER PUBLICATIONS

Application No. PCT/US2021/044575, International Preliminary Report on Patentability, Mailed on Feb. 16, 2023, 10 pages.
Application No. PCT/US2021/044575, International Search Report and Written Opinion, Mailed on Feb. 2, 2022, 14 pages.
PCT/US2021/044575, "Invitation to Pay Additional Fees and, Where Applicable, Protest Fee", Nov. 18, 2021, 2 pages.
PCT/US2021/044576, "Invitation to Pay Additional Fees and, Where Applicable, Protest Fee", Nov. 12, 2021, 2 pages.
Application No. PCT/US2021/044577, International Preliminary Report on Patentability, Mailed on Feb. 16, 2023, 7 pages.
Application No. PCT/US2021/044577, International Search Report and Written Opinion, Mailed on Dec. 9, 2021, 10 pages.
Poosarla et al., "Computational de novo Design of Antibodies binding to a Peptide with High Affinity", Biotechnology and Bioengineering, vol. 114, No. 6, Jan. 6, 2017, pp. 1331-1342.
Vajda et al., "Progress Toward Improved Understanding of Antibody Maturation", Current Opinion in Structural Biology, vol. 67, Apr. 2021, pp. 226-231.

\* cited by examiner

SEQUENCE LISTING

<160> NUMBER OF SEQ ID NOS: 202

<210> SEQ ID NO 1
<211> LENGTH: 636
<212> TYPE: PRT
<213> ORGANISM: Homo sapiens

<400> SEQUENCE: 1

```
Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
            20                  25                  30

Gln Gly Ser Ala Gly Pro Leu Gln Cys Tyr Gly Val Gly Pro Leu Gly
        35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
```

```
                100             105             110
Pro Leu Trp Pro Pro Val Phe Val Asn Leu Glu Thr Gln Met Lys Pro
            115             120             125
Asn Ala Pro Arg Leu Gly Pro Asp Val Asp Phe Ser Glu Asp Asp Pro
            130             135             140
Leu Glu Ala Thr Val His Trp Ala Pro Pro Thr Trp Pro Ser His Lys
145             150             155             160
Val Leu Ile Cys Gln Phe His Tyr Arg Arg Cys Gln Glu Ala Ala Trp
            165             170             175
Thr Leu Leu Glu Pro Glu Leu Lys Thr Ile Pro Leu Thr Pro Val Glu
            180             185             190
Ile Gln Asp Leu Glu Leu Ala Thr Gly Tyr Lys Val Tyr Gly Arg Cys
            195             200             205
Arg Met Glu Lys Glu Glu Asp Leu Trp Gly Glu Trp Ser Pro Ile Leu
            210             215             220
Ser Phe Gln Thr Pro Pro Ser Ala Pro Lys Asp Val Trp Val Ser Gly
225             230             235             240
Asn Leu Cys Gly Thr Pro Gly Gly Glu Glu Pro Leu Leu Leu Trp Lys
            245             250             255
Ala Pro Gly Pro Cys Val Gln Val Ser Tyr Lys Val Trp Phe Trp Val
            260             265             270
Gly Gly Arg Glu Leu Ser Pro Glu Gly Ile Thr Cys Cys Cys Ser Leu
            275             280             285
Ile Pro Ser Gly Ala Glu Trp Ala Arg Val Ser Ala Val Asn Ala Thr
            290             295             300
Ser Trp Glu Pro Leu Thr Asn Leu Ser Leu Val Cys Leu Asp Ser Ala
305             310             315             320
Ser Ala Pro Arg Ser Val Ala Val Ser Ser Ile Ala Gly Ser Thr Glu
            325             330             335
Leu Leu Val Thr Trp Gln Pro Gly Pro Gly Glu Pro Leu Glu His Val
            340             345             350
Val Asp Trp Ala Arg Asp Gly Asp Pro Leu Glu Lys Leu Asn Trp Val
            355             360             365
Arg Leu Pro Pro Gly Asn Leu Ser Ala Leu Leu Pro Gly Asn Phe Thr
            370             375             380
Val Gly Val Pro Tyr Arg Ile Thr Val Thr Ala Val Ser Ala Ser Gly
385             390             395             400
Leu Ala Ser Ala Ser Ser Val Trp Gly Phe Arg Glu Glu Leu Ala Pro
            405             410             415
Leu Val Gly Pro Thr Leu Trp Arg Leu Gln Asp Ala Pro Pro Gly Thr
            420             425             430
Pro Ala Ile Ala Trp Gly Glu Val Pro Arg His Gln Leu Arg Gly His
            435             440             445
Leu Thr His Tyr Thr Leu Cys Ala Gln Ser Gly Thr Ser Pro Ser Val
            450             455             460
Cys Met Asn Val Ser Gly Asn Thr Gln Ser Val Thr Leu Pro Asp Leu
465             470             475             480
Pro Trp Gly Pro Cys Glu Leu Trp Val Thr Ala Ser Thr Ile Ala Gly
            485             490             495
Gln Gly Pro Pro Gly Pro Ile Leu Arg Leu His Leu Pro Asp Asn Thr
            500             505             510
Leu Arg Trp Lys Val Leu Pro Gly Ile Leu Phe Leu Trp Gly Leu Phe
            515             520             525
```

```
Leu Leu Gly Cys Gly Leu Ser Leu Ala Thr Ser Gly Arg Cys Tyr His
            530                 535                 540

Leu Arg His Lys Val Leu Pro Arg Trp Val Trp Glu Lys Val Pro Asp
545                 550                 555                 560

Pro Ala Asn Ser Ser Ser Gly Gln Pro His Met Glu Gln Val Pro Glu
                565                 570                 575

Ala Gln Pro Leu Gly Asp Leu Pro Ile Leu Glu Val Glu Glu Met Glu
            580                 585                 590

Pro Pro Pro Val Met Glu Ser Ser Gln Pro Ala Gln Ala Thr Ala Pro
        595                 600                 605

Leu Asp Ser Gly Tyr Glu Lys His Phe Leu Pro Thr Pro Glu Glu Leu
            610                 615                 620

Gly Leu Leu Gly Pro Pro Arg Pro Gln Val Leu Ala
625                 630                 635

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Ile
        35                  40                  45

Ser Thr Ile Ser Ala Gly Gly Asp Thr Thr Leu Tyr Ala Asp Ser Val
    50                  55                  60

Lys Gly Arg Phe Thr Ser Ser Arg Asp Asn Ala Lys Asn Thr Leu Tyr
65                  70                  75                  80

Leu Gln Leu Asn Ser Leu Lys Thr Glu Asp Ala Ala Ile Tyr Tyr Cys
                85                  90                  95

Ala Lys Arg Ile Asp Cys Asn Ser Gly Tyr Cys Tyr Arg Arg Asn Tyr
            100                 105                 110

Trp Gly Gln Gly Thr Gln Val Thr Val Ser Ser
        115                 120

<210> SEQ ID NO 3
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Leu Ser
            20                  25                  30

Gly Met Ser Trp Val Arg Gln Ala Pro Gly Lys Gly Leu Glu Trp Val
        35                  40                  45

Ser Ala Ile Ser Ser Gly Gly Ala Ser Thr Tyr Tyr Thr Asp Ser Val
    50                  55                  60
```

```
Lys Gly Arg Phe Thr Ile Ser Arg Asp Asn Ala Lys Asn Ile Leu Tyr
 65                  70                  75                  80

Leu Gln Leu Asn Ser Leu Lys Thr Glu Asp Thr Ala Met Tyr Tyr Cys
                 85                  90                  95

Ala Lys Gly Gly Ser Gly Tyr Gly Asp Ala Ser Arg Met Thr Ser Pro
            100                 105                 110

Gly Ser Gln Gly Thr Gln Val Thr Val Ser Ser
        115                 120

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Ser Val Gln Ala Gly Gly
 1               5                  10                  15

Ser Leu Arg Leu Ser Cys Val Ala Ser Gly Tyr Val Ser Cys Asp Tyr
             20                  25                  30

Phe Leu Pro Ser Trp Tyr Arg Gln Ala Pro Gly Lys Glu Arg Glu Phe
         35                  40                  45

Val Ser Ile Ile Asp Gly Thr Gly Ser Thr Ser Tyr Ala Ala Ser Val
     50                  55                  60

Lys Gly Arg Phe Thr Ala Ser Glu Asp Lys Gly Lys Asn Ile Ala Tyr
 65                  70                  75                  80

Leu Gln Met Asn Ser Leu Lys Pro Glu Asp Thr Ala Met Tyr Tyr Cys
                 85                  90                  95

Lys Ala Ser Cys Val Arg Gly Arg Ala Val Ser Glu Tyr Trp Gly Gln
            100                 105                 110

Gly Thr Gln Val Thr Val Ser Ser
        115                 120

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Leu Val Gln Pro Gly Glu
 1               5                  10                  15

Ser Leu Arg Leu Ser Cys Thr Ala Ser Gly Phe Thr Phe Ser Asn Tyr
             20                  25                  30

Ala Met Ser Trp Val Arg Gln Ala Pro Gly Lys Gly Leu Glu Trp Val
         35                  40                  45

Ser Gly Ile Asn Val Ala Tyr Gly Ile Thr Ser Tyr Ala Asp Ser Val
     50                  55                  60

Lys Gly Arg Phe Thr Ile Ser Arg Asp Asn Thr Lys Asn Thr Leu Tyr
 65                  70                  75                  80

Leu Gln Leu Asn Ser Leu Lys Thr Glu Asp Thr Ala Ile Tyr Tyr Cys
                 85                  90                  95

Val Lys His Ser Gly Thr Thr Ile Pro Arg Gly Phe Ile Ser Tyr Thr
            100                 105                 110
```

Lys Arg Gly Gln Gly Thr Gln Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Val Ser Cys Asp Tyr
            20                  25                  30

Phe Leu Pro Ser Trp Tyr Arg Gln Ala Pro Gly Lys Glu Arg Glu Phe
        35                  40                  45

Val Ser Val Ile Asp Gly Thr Gly Ser Thr Ser Tyr Ala Ala Ser Val
    50                  55                  60

Lys Gly Arg Phe Thr Ala Ser Gln Asp Lys Gly Lys Asn Ile Ala Tyr
65                  70                  75                  80

Leu Gln Met Asn Ser Leu Lys Pro Glu Asp Thr Ala Met Tyr Tyr Cys
                85                  90                  95

Lys Ala Ser Cys Val Arg Gly Arg Ala Ile Ser Glu Tyr Trp Gly Gln
            100                 105                 110

Gly Thr Gln Val Thr Val Ser Ser
        115                 120

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Lys Trp Val Arg Gln Ala Pro Gly Lys Gly Leu Glu Trp Val
        35                  40                  45

Ser Thr Ile Ser Ser Gly Gly Ser Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Ile Glu Asp Thr Ala Met Tyr Tyr Cys
                85                  90                  95

Ala Lys Ala Ile Val Pro Thr Gly Ala Thr Met Glu Arg Gly Gln Gly
            100                 105                 110

Thr Gln Val Thr Val Ser Ser
        115

<210> SEQ ID NO 8
<211> LENGTH: 123
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Ile
        35                  40                  45

Ser Thr Ile Ser Ala Gly Gly Asp Thr Thr Leu Tyr Ala Asp Ser Val
    50                  55                  60

Lys Gly Arg Phe Thr Ser Ser Arg Asp Asn Ala Lys Asn Thr Leu Tyr
65                  70                  75                  80

Leu Gln Leu Asn Ser Leu Lys Thr Glu Asp Thr Ala Ile Tyr Tyr Cys
                85                  90                  95

Ala Lys Arg Ile Asp Cys Asn Ser Gly Tyr Cys Tyr Arg Arg Asn Tyr
            100                 105                 110

Trp Gly Gln Gly Thr Gln Val Thr Val Ser Ser
        115                 120

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Ser Val Gln Val Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Ile
        35                  40                  45

Ser Thr Ile Ser Ala Gly Gly Asp Thr Thr Leu Tyr Ala Asp Ser Val
    50                  55                  60

Lys Gly Arg Phe Thr Ser Ser Arg Asp Asn Ala Lys Asn Thr Leu Tyr
65                  70                  75                  80

Leu Gln Leu Asn Ser Leu Lys Thr Glu Asp Thr Ala Ile Tyr Tyr Cys
                85                  90                  95

Ala Lys Arg Ile Asp Cys Asn Ser Gly Tyr Cys Tyr Arg Arg Asn Tyr
            100                 105                 110

Trp Gly Gln Gly Thr Gln Val Thr Val Ser Ser
        115                 120

<210> SEQ ID NO 10
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Ser Val Gln Ser Gly Gly
1               5                   10                  15
```

Ser Leu Arg Leu Ser Cys Ala Ala Ser Gly Phe Thr Tyr Ser Thr Ser
            20                  25                  30

Asn Ser Trp Met Ala Trp Phe Arg Gln Ala Pro Gly Lys Glu Arg Glu
            35                  40                  45

Gly Val Ala Ala Ile Tyr Thr Val Gly Gly Ser Ile Phe Tyr Ala Asp
            50                  55                  60

Ser Val Arg Gly Arg Phe Thr Ile Ser Gln Asp Ala Thr Lys Asn Met
65                  70                  75                  80

Phe Tyr Leu Gln Met Asn Thr Leu Lys Pro Glu Asp Thr Ala Met Tyr
                85                  90                  95

Tyr Cys Ala Ala Ala Ser Gly Arg Leu Arg Gly Lys Trp Phe Trp Pro
            100                 105                 110

Tyr Glu Tyr Asn Tyr Trp Gly Gln Gly Thr Gln Val Thr Val Ser Ser
            115                 120                 125

<210> SEQ ID NO 11
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Ser Val Gln Ala Gly Gly
1               5                   10                  15

Ser Leu Arg Leu Ser Cys Arg Ala Ser Gly Ser Thr Tyr Ser Asn Tyr
            20                  25                  30

Cys Leu Gly Trp Phe Arg Gln Ile Thr Gly Lys Glu Arg Glu Gly Val
            35                  40                  45

Ala Val Ile Asn Trp Val Gly Gly Met Leu Tyr Phe Ala Asp Ser Val
            50                  55                  60

Lys Gly Arg Phe Thr Val Ser Gln Asp Gln Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Glu Ser Val Ser Ser Phe Ser Cys Gly Gly Trp Leu Thr Arg
            100                 105                 110

Pro Asp Arg Val Pro Tyr Trp Gly Gln Gly Thr Gln Val Thr Val Ser
            115                 120                 125

Ser

<210> SEQ ID NO 12
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Arg Ala Ser Gly Ser Thr Tyr Ser Asn Tyr
            20                  25                  30

Cys Leu Gly Trp Phe Arg Gln Ser Thr Gly Lys Glu Arg Glu Gly Val
            35                  40                  45

Ala Val Ile Asn Trp Val Gly Gly Met Leu Tyr Phe Ala Asp Ser Val

```
                50                  55                  60
Lys Gly Arg Phe Thr Val Ser Gln Asp His Ala Lys Asn Thr Val Thr
 65                  70                  75                  80

Leu Gln Met Asn Ser Leu Lys Pro Glu Asp Thr Ala Met Tyr Tyr Cys
                 85                  90                  95

Ala Ala Glu Ser Val Ser Ser Phe Ser Cys Gly Gly Trp Leu Thr Arg
                100                 105                 110

Pro Gly Arg Val Pro Tyr Trp Gly Gln Gly Thr Gln Val Thr Val Ser
            115                 120                 125

Ser

<210> SEQ ID NO 13
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Gly Gly Ser Val Gln Ala Gly Glu
 1               5                  10                  15

Ser Leu Arg Leu Ser Cys Arg Ala Ser Gly Ser Thr Tyr Ser Asn Tyr
                20                  25                  30

Cys Leu Gly Trp Phe Arg Gln Ile Thr Gly Lys Glu Arg Glu Gly Val
             35                  40                  45

Ala Val Ile Asn Trp Val Gly Gly Met Leu Tyr Phe Ala Asp Ser Val
         50                  55                  60

Lys Gly Arg Phe Thr Val Ser Gln Asp Gln Ala Lys Asn Thr Val Tyr
 65                  70                  75                  80

Leu Glu Met Asn Ser Leu Lys Pro Glu Asp Thr Ala Met Tyr Tyr Cys
                 85                  90                  95

Ala Thr Glu Ser Val Ser Ser Phe Ser Cys Gly Gly Trp Leu Thr Arg
                100                 105                 110

Pro Asp Arg Val Pro Tyr Trp Gly Gln Gly Thr Gln Val Thr Val Ser
            115                 120                 125

Ser

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Gly Gly Ser Val Gln Ala Gly Gly
 1               5                  10                  15

Ser Leu Arg Leu Ser Cys Val Ala Ser Gly Tyr Val Ser Cys Asp Tyr
                20                  25                  30

Phe Leu Pro Ser Trp Tyr Arg Gln Ala Pro Gly Lys Glu Arg Glu Phe
             35                  40                  45

Val Ser Ile Ile Asp Gly Thr Gly Ser Thr Tyr Ala Ala Ser Val
         50                  55                  60

Lys Gly Arg Phe Thr Ala Ser Gln Asp Arg Gly Lys Asn Ile Ala Tyr
 65                  70                  75                  80
```

-continued

```
Leu Gln Met Asn Ser Leu Lys Pro Glu Asp Thr Ala Met Tyr Tyr Cys
                 85                  90                  95

Lys Ala Ser Cys Val Arg Gly Arg Thr Ile Ser Glu Tyr Trp Gly Gln
            100                 105                 110

Gly Thr Gln Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Val Ser Cys Asp Tyr
            20                  25                  30

Phe Leu Pro Ser Trp Tyr Arg Gln Ala Pro Gly Lys Glu Arg Glu Phe
        35                  40                  45

Val Ser Ile Ile Asp Gly Thr Gly Ser Thr Ser Tyr Ala Ala Ser Val
    50                  55                  60

Lys Gly Arg Phe Thr Ala Ser Gln Asp Lys Gly Lys Asn Ile Ala Tyr
65                  70                  75                  80

Leu Gln Met Asn Ser Leu Lys Pro Glu Asp Thr Ala Met Tyr Tyr Cys
                 85                  90                  95

Lys Ala Ser Cys Val Arg Gly Arg Ala Ile Ser Glu Tyr Trp Gly Gln
            100                 105                 110

Gly Thr Gln Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Val Ser Cys Asp Tyr
            20                  25                  30

Phe Leu Pro Ser Trp Tyr Arg Gln Ala Pro Gly Lys Glu Arg Glu Phe
        35                  40                  45

Val Ser Ile Ile Asp Gly Thr Gly Ser Thr Ser Tyr Ala Ala Ser Val
    50                  55                  60

Lys Gly Arg Phe Thr Ala Ser Gln Asp Lys Gly Lys Asn Ile Ala Tyr
65                  70                  75                  80

Leu Gln Met Asn Thr Leu Lys Pro Glu Asp Thr Ala Met Tyr Tyr Cys
                 85                  90                  95

Lys Ala Ser Cys Val Arg Gly Arg Ala Ile Ser Glu Tyr Trp Gly Gln
            100                 105                 110

Gly Thr Gln Val Thr Val Ser Ser
        115                 120
```

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Gln Val Gln Leu Gln Glu Ser Gly Gly Gly Ser Val Gln Ala Gly Gly
1               5                   10                  15

Ser Leu Arg Leu Ser Cys Arg Ala Ser Gly Ser Thr Tyr Ser Asn Tyr
            20                  25                  30

Cys Leu Gly Trp Phe Arg Gln Ile Thr Gly Lys Glu Arg Glu Gly Val
        35                  40                  45

Ala Val Ile Asn Trp Val Gly Gly Met Leu Tyr Phe Ala Asp Ser Val
    50                  55                  60

Lys Gly Arg Phe Thr Val Ser Gln Asp Gln Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Ser Ala Ser Ser Phe Ser Cys Gly Gly Trp Leu Thr Arg
            100                 105                 110

Pro Asp Arg Val Pro Tyr Trp Gly Gln Gly Thr Gln Val Thr Val Ser
        115                 120                 125

Ser

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Leu Ser
            20                  25                  30

Gly Met Ser Trp Val Arg Gln Ala Pro Gly Lys Gly Leu Glu Trp Val
        35                  40                  45

Ser Ala Ile Ser Ser Gly Gly Ala Ser Thr Tyr Tyr Thr Asp Ser Val
    50                  55                  60

Lys Gly Arg Phe Thr Ile Ser Arg Asp Asn Ala Lys Asn Met Leu Tyr
65                  70                  75                  80

Leu Gln Leu Asn Ser Leu Lys Thr Glu Asp Thr Ala Met Tyr Tyr Cys
                85                  90                  95

Ala Lys Gly Gly Ser Gly Tyr Gly Asp Ala Ser Arg Met Thr Ser Pro
            100                 105                 110

Gly Ser Gln Gly Thr Gln Val Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Val Ser Cys Asp Tyr
            20                  25                  30

Phe Leu Pro Ser Trp Tyr Arg Gln Ala Pro Gly Lys Glu Arg Glu Phe
        35                  40                  45

Val Ser Ile Ile Asp Gly Thr Gly Ser Thr Tyr Ala Ala Ser Val
    50                  55                  60

Lys Gly Arg Phe Thr Ala Ser Gln Asp Lys Gly Lys Asn Ile Ala Tyr
65                  70                  75                  80

Leu Gln Met Asn Ser Leu Lys Pro Glu Asp Thr Ala Met Tyr Tyr Cys
                85                  90                  95

Lys Ala Ser Cys Val Arg Gly Arg Gly Ile Ser Glu Tyr Trp Gly Gln
            100                 105                 110

Gly Thr Gln Val Thr Val Ser Ser
        115                 120

<210> SEQ ID NO 20
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Gly Gly Ser Val Gln Ala Gly Gly
1               5                   10                  15

Ser Leu Arg Leu Ser Cys Arg Ala Ser Gly Ser Thr Tyr Ser Asn Tyr
            20                  25                  30

Cys Leu Gly Trp Phe Arg Gln Ile Thr Gly Lys Glu Arg Glu Gly Val
        35                  40                  45

Ala Val Ile Asn Trp Val Gly Gly Met Leu Tyr Phe Ala Asp Ser Val
    50                  55                  60

Lys Gly Arg Phe Thr Val Ser Gln Asp Gln Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Ser Val Ser Ser Phe Ser Cys Gly Gly Trp Leu Thr Arg
            100                 105                 110

Pro Asp Arg Val Pro Tyr Trp Gly Gln Gly Thr Gln Val Thr Val Ser
        115                 120                 125

Ser

<210> SEQ ID NO 21
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Leu Val Gln Pro Gly Gly
1               5                   10                  15

-continued

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Thr Ile Ser Ser Gly Gly Asp Thr Thr Leu Tyr Ala Asp Ser Val
    50                  55                  60

Lys Gly Arg Phe Thr Ser Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
                85                  90                  95

Ala Lys Arg Ile Asp Cys Asn Ser Gly Tyr Cys Tyr Lys Arg Ser Tyr
            100                 105                 110

Trp Gly Gln Gly Thr Gln Val Thr Val Ser Ser
            115                 120

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Leu Ser
            20                  25                  30

Ser Met Ser Trp Val Arg Gln Ala Pro Gly Lys Gly Leu Glu Trp Val
        35                  40                  45

Ser Ala Ile Ser Ser Gly Gly Ala Ser Thr Tyr Tyr Thr Asp Ser Val
    50                  55                  60

Lys Gly Arg Phe Thr Ile Ser Arg Asp Asn Ala Lys Asn Met Leu Tyr
65                  70                  75                  80

Leu Gln Leu Asn Ser Leu Lys Thr Glu Asp Thr Ala Met Tyr Tyr Cys
                85                  90                  95

Ala Lys Gly Gly Ser Gly Tyr Gly Asp Ala Ser Arg Met Thr Ser Pro
            100                 105                 110

Gly Ser Gln Gly Thr Gln Val Thr Val Ser Ser
            115                 120

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Gly Gly Ser Val Gln Ala Gly Gly
1               5                   10                  15

Ser Leu Arg Leu Ser Cys Arg Ala Ser Gly Ser Thr Tyr Ser Asn Tyr
            20                  25                  30

Cys Leu Gly Trp Phe Arg Gln Thr Thr Gly Lys Glu Arg Glu Gly Val
        35                  40                  45

Ala Val Ile Asn Trp Val Gly Gly Met Leu Tyr Phe Ala Asp Ser Val
    50                  55                  60

Lys Gly Arg Phe Thr Val Ser Gln Asp Gln Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Glu Ser Val Ser Ser Phe Ser Cys Gly Gly Trp Leu Thr Arg
            100                 105                 110

Pro Asp Arg Val Pro Tyr Trp Gly Gln Gly Thr Gln Val Thr Val Ser
        115                 120                 125

Ser

<210> SEQ ID NO 24
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Gly Gly Ser Val Gln Ala Gly Gly
1               5                   10                  15

Ser Leu Arg Leu Ser Cys Arg Ala Ser Arg Ser Pro Tyr Gly Asn Tyr
            20                  25                  30

Cys Leu Gly Trp Phe Arg Gln Ser Thr Gly Lys Glu Arg Glu Gly Val
        35                  40                  45

Ala Val Ile Asn Trp Val Gly Met Leu Tyr Phe Ala Asp Ser Val
    50                  55                  60

Lys Gly Arg Phe Thr Val Ser Gln Asp His Ala Lys Asn Thr Val Thr
 65                  70                  75                  80

Leu Gln Met Asn Ser Leu Lys Pro Glu Asp Thr Ala Met Tyr Tyr Cys
                 85                  90                  95

Ala Ala Glu Ser Val Ser Ser Phe Ser Cys Gly Gly Trp Leu Thr Arg
            100                 105                 110

Pro Asp Arg Val Pro Tyr Trp Gly Gln Gly Thr Gln Val Thr Val Ser
        115                 120                 125

Ser

<210> SEQ ID NO 25
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser His Ser
            20                  25                  30

Gly Met Ser Trp Val Arg Gln Ala Pro Gly Lys Gly Leu Glu Trp Val
        35                  40                  45

Ser Thr Ile Asn Ser Gly Gly Ala Ser Thr Tyr Tyr Thr Asp Ser Val
    50                  55                  60

Lys Gly Arg Phe Thr Ile Ser Arg Asp Asn Ala Lys Asn Met Leu Tyr
 65                  70                  75                  80

Leu Gln Leu Asn Ser Leu Lys Thr Glu Asp Thr Ala Met Tyr Tyr Cys
                 85                  90                  95

```
Ala Lys Gly Gly Ser Gly Tyr Gly Asp Ala Ser Arg Met Thr Ser Pro
            100                 105                 110

Gly Ser Gln Gly Thr Gln Val Thr Val Ser Ser
        115                 120
```

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Phe Thr Phe Ser Ser Tyr Pro Met Ser
1               5
```

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Thr Ile Ser Ala Gly Gly Asp Thr Thr Leu Tyr Ala Asp Ser Val Lys
1               5                   10                  15

Gly
```

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Arg Ile Asp Cys Asn Ser Gly Tyr Cys Tyr Arg Arg Asn Tyr
1               5                   10
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Phe Thr Phe Ser Leu Ser Gly Met Ser
1               5
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Ala Ile Ser Ser Gly Gly Ala Ser Thr Tyr Tyr Thr Asp Ser Val Lys
1               5                   10                  15
```

Gly

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Ser Gly Tyr Gly Asp Ala Ser Arg Met Thr Ser Pro
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Val Ser Cys Asp Tyr Phe Leu Pro Ser
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Ile Asp Gly Thr Gly Ser Thr Ser Tyr Ala Ala Ser Val Lys Gly
1               5                   10                  15

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Cys Val Arg Gly Arg Ala Val Ser Glu Tyr
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Thr Phe Ser Asn Tyr Ala Met Ser
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 36

Gly Ile Asn Val Ala Tyr Gly Ile Thr Ser Tyr Ala Asp Ser Val Lys
1               5                   10                  15
Gly

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Ser Gly Thr Thr Ile Pro Arg Gly Phe Ile Ser Tyr Thr Lys
1               5                   10                  15

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Val Ser Cys Asp Tyr Phe Leu Pro Ser
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ile Asp Gly Thr Gly Ser Thr Ser Tyr Ala Ala Ser Val Lys Gly
1               5                   10                  15

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Cys Val Arg Gly Arg Ala Ile Ser Glu Tyr
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Ser Phe Ser Ser Tyr Ala Met Lys
1               5
```

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Ile Ser Ser Gly Gly Ser Ser Thr Asn Tyr Ala Asp Ser Val Lys
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ile Val Pro Thr Gly Ala Thr Met Glu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Thr Phe Ser Ser Tyr Pro Met Ser
1               5

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Ile Ser Ala Gly Gly Asp Thr Thr Leu Tyr Ala Asp Ser Val Lys
1               5                   10                  15

Gly

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ile Asp Cys Asn Ser Gly Tyr Cys Tyr Arg Arg Asn Tyr
1               5                   10

<210> SEQ ID NO 47
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 47

Phe Thr Phe Ser Ser Tyr Pro Met Ser
1               5

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ile Ser Ala Gly Gly Asp Thr Thr Leu Tyr Ala Asp Ser Val Lys
1               5                   10                  15

Gly

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ile Asp Cys Asn Ser Gly Tyr Cys Tyr Arg Arg Asn Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Thr Tyr Ser Thr Ser Asn Ser Trp Met Ala
1               5                   10

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Ile Tyr Thr Val Gly Gly Ser Ile Phe Tyr Ala Asp Ser Val Arg
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

```
Ala Ser Gly Arg Leu Arg Gly Lys Trp Phe Trp Pro Tyr Glu Tyr Asn
1               5                   10                  15
Tyr

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Thr Tyr Ser Asn Tyr Cys Leu Gly
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Ile Asn Trp Val Gly Gly Met Leu Tyr Phe Ala Asp Ser Val Lys
1               5                   10                  15
Gly

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Ser Val Ser Ser Phe Ser Cys Gly Gly Trp Leu Thr Arg Pro Asp
1               5                   10                  15
Arg Val Pro Tyr
            20

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Thr Tyr Ser Asn Tyr Cys Leu Gly
1               5

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Ile Asn Trp Val Gly Gly Met Leu Tyr Phe Ala Asp Ser Val Lys
```

```
<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Ser Val Ser Ser Phe Ser Cys Gly Gly Trp Leu Thr Arg Pro Gly
1               5                   10                  15

Arg Val Pro Tyr
            20

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Thr Tyr Ser Asn Tyr Cys Leu Gly
1               5

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Ile Asn Trp Val Gly Gly Met Leu Tyr Phe Ala Asp Ser Val Lys
1               5                   10                  15

Gly

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Ser Val Ser Ser Phe Ser Cys Gly Gly Trp Leu Thr Arg Pro Asp
1               5                   10                  15

Arg Val Pro Tyr
            20

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

Preceding sequence (top of page):

```
1               5                   10                  15
Gly
```

```
Tyr Val Ser Cys Asp Tyr Phe Leu Pro Ser
1               5                   10
```

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Ile Ile Asp Gly Thr Gly Ser Thr Ser Tyr Ala Ala Ser Val Lys Gly
1               5                   10                  15
```

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Ser Cys Val Arg Gly Arg Thr Ile Ser Glu Tyr
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Tyr Val Ser Cys Asp Tyr Phe Leu Pro Ser
1               5                   10
```

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Ile Ile Asp Gly Thr Gly Ser Thr Ser Tyr Ala Ala Ser Val Lys Gly
1               5                   10                  15
```

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Ser Cys Val Arg Gly Arg Ala Ile Ser Glu Tyr
1               5                   10
```

<210> SEQ ID NO 68
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 68

Tyr Val Ser Cys Asp Tyr Phe Leu Pro Ser
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Ile Asp Gly Thr Gly Ser Thr Ser Tyr Ala Ala Ser Val Lys Gly
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Cys Val Arg Gly Arg Ala Ile Ser Glu Tyr
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Thr Tyr Ser Asn Tyr Cys Leu Gly
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Val Ile Asn Trp Val Gly Gly Met Leu Tyr Phe Ala Asp Ser Val Lys
1               5                   10                  15

Gly

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Ser Ala Ser Ser Phe Ser Cys Gly Gly Trp Leu Thr Arg Pro Asp
1               5                   10                  15
```

Arg Val Pro Tyr
            20

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Thr Phe Ser Leu Ser Gly Met Ser
1               5

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Ile Ser Ser Gly Gly Ala Ser Thr Tyr Tyr Thr Asp Ser Val Lys
1               5                   10                  15

Gly

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Ser Gly Tyr Gly Asp Ala Ser Arg Met Thr Ser Pro
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Val Ser Cys Asp Tyr Phe Leu Pro Ser
1               5                   10

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Ile Asp Gly Thr Gly Ser Thr Ser Tyr Ala Ala Ser Val Lys Gly
1               5                   10                  15

<210> SEQ ID NO 79
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Cys Val Arg Gly Arg Gly Ile Ser Glu Tyr
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Thr Tyr Ser Asn Tyr Cys Leu Gly
1               5

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Ile Asn Trp Val Gly Gly Met Leu Tyr Phe Ala Asp Ser Val Lys
1               5                   10                  15

Gly

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Ser Val Ser Ser Phe Ser Cys Gly Gly Trp Leu Thr Arg Pro Asp
1               5                   10                  15

Arg Val Pro Tyr
            20

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Thr Phe Ser Ser Tyr Pro Met Ser
1               5

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                                     peptide

<400> SEQUENCE: 84

Thr Ile Ser Ser Gly Gly Asp Thr Thr Leu Tyr Ala Asp Ser Val Lys
1               5                   10                  15

Gly

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ile Asp Cys Asn Ser Gly Tyr Cys Tyr Lys Arg Ser Tyr
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Phe Thr Phe Ser Leu Ser Ser Met Ser
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Ile Ser Ser Gly Gly Ala Ser Thr Tyr Tyr Thr Asp Ser Val Lys
1               5                   10                  15

Gly

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Ser Gly Tyr Gly Asp Ala Ser Arg Met Thr Ser Pro
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Thr Tyr Ser Asn Tyr Cys Leu Gly
```

```
1               5
```

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Val Ile Asn Trp Val Gly Gly Met Leu Tyr Phe Ala Asp Ser Val Lys
1               5                   10                  15

Gly
```

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Glu Ser Val Ser Ser Phe Ser Cys Gly Gly Trp Leu Thr Arg Pro Asp
1               5                   10                  15

Arg Val Pro Tyr
            20
```

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Ser Pro Tyr Gly Asn Tyr Cys Leu Gly
1               5
```

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Val Ile Asn Trp Val Gly Gly Met Leu Tyr Phe Ala Asp Ser Val Lys
1               5                   10                  15

Gly
```

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Glu Ser Val Ser Ser Phe Ser Cys Gly Gly Trp Leu Thr Arg Pro Asp
1               5                   10                  15
```

Arg Val Pro Tyr
            20

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Thr Phe Ser His Ser Gly Met Ser
1               5

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Ile Asn Ser Gly Gly Ala Ser Thr Tyr Tyr Thr Asp Ser Val Lys
1               5                   10                  15

Gly

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Ser Gly Tyr Gly Asp Ala Ser Arg Met Thr Ser Pro
1               5                   10

<210> SEQ ID NO 98
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caggtgcagc tgcaggagag cggcggcggc ctggtgcagc ccggcggcag cctgaggctg      60
agctgcgccg ccagcggctt caccttcagc agctacccca tgagctgggt gaggcaggcc     120
cccggcaagg gcctggagtg gatcagcacc atcagcgccg gcggcgacac caccctgtac     180
gccgacagcg tgaagggcag gttcaccagc agcagggaca cgccaagaa caccctgtac      240 ctgcagctga acagcctgaa gaccgaggac gccgccatct actactgcgc caagaggatc     300
gactgcaaca gcggctactg ctacaggagg aactactggg gccagggcac ccaggtgacc     360
gtgagcagc                                                             369

<210> SEQ ID NO 99
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
caggtgcagc tgcaggagag cggcggcggc ctggtgcagc ccggcggcag cctgaggctg      60
agctgcgccg ccagcggctt caccttcagc ctgagcggca tgagctgggt gaggcaggcc     120
cccggcaagg gcctggagtg ggtgagcgcc atcagcagcg gcggcgccag cacctactac     180
accgacagcg tgaagggcag gttcaccatc agcagggaca cgccaagaa catcctgtac      240
ctgcagctga acagcctgaa gaccgaggac accgccatgt actactgcgc caagggcggc     300
agcggctacg gcgacgccag caggatgacc agccccggca gccagggcac ccaggtgacc     360
gtgagcagc                                                             369
```

<210> SEQ ID NO 100
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
caggtgcagc tgcaggagag cggcggcggc agcgtgcagg ccggcggcag cctgaggctg      60
agctgcgtgg ccagcggcta cgtgagctgc gactacttcc tgcccagctg gtacaggcag     120
gcccccggca aggagaggga gttcgtgagc atcatcgacg gcaccggcag caccagctac     180
gccgccagcg tgaagggcag gttcaccgcc agcgaggaca agggcaagaa catcgcctac     240
ctgcagatga acagcctgaa gcccgaggac accgccatgt actactgcaa ggccagctgc     300
gtgaggggca gggccgtgag cgagtactgg ggccagggca cccaggtgac cgtgagcagc     360
```

<210> SEQ ID NO 101
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
caggtgcagc tgcaggagag cggcggcggc ctggtgcagc ccggcgagag cctgaggctg      60
agctgcaccg ccagcggctt caccttcagc aactacgcca tgagctgggt gaggcaggcc     120
cccggcaagg gcctggagtg ggtgagcggc atcaacgtgg cctacggcat caccagctac     180
gccgacagcg tgaagggcag gttcaccatc agcagggaca caccaagaa caccctgtac      240
ctgcagctga acagcctgaa gaccgaggac accgccatct actactgcgt gaagcacagc     300
ggcaccacca tccccagggg cttcatcagc tacaccaaga ggggcagggg cacccaggtg     360
accgtgagca gc                                                         372
```

<210> SEQ ID NO 102
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
caggtgcagc tgcaggagag cggcggcggc agcgtgcagg ccggcggcag cctgaggctg      60
```

```
agctgcaccg ccagcggcta cgtgagctgc gactacttcc tgcccagctg gtacaggcag    120
gcccccggca aggagaggga gttcgtgagc gtgatcgacg gcaccggcag caccagctac    180
gccgccagcg tgaagggcag gttcaccgcc agccaggaca agggcaagaa catcgcctac    240
ctgcagatga acagcctgaa gcccgaggac accgccatgt actactgcaa ggccagctgc    300
gtgaggggca gggccatcag cgagtactgg ggccagggca cccaggtgac cgtgagcagc    360

<210> SEQ ID NO 103
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
caggtgcagc tgcaggagag cggcggcggc ctggtgcagc ccggcggcag cctgaggctg     60
agctgcgccg ccagcggctt cagcttcagc agctacgcca tgaagtgggt gaggcaggcc    120
cccggcaagg gcctggagtg ggtgagcacc atcagcagcg gcggcagcag caccaactac    180
gccgacagcg tgaagggcag gttcaccatc agcagggaca cgccaagaa cacccctgtac    240 ctgcagctga acagcctgaa gatcgaggac accgccatgt actactgcgc caaggccatc    300
gtgcccaccg cgccaccat ggagaggggc cagggcaccc aggtgaccgt gagcagc        357

<210> SEQ ID NO 104
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
caggtgcagc tgcaggagag cggcggcggc ctggtgcagc ccggcggcag cctgaggctg     60
agctgcgccg ccagcggctt caccttcagc agctaccca tgagctgggt gaggcaggcc    120
cccggcaagg gcctggagtg gatcagcacc atcagcgccg gcggcgacac cacccctgtac   180 gccgacagcg tgaagggcag gttcaccagc agcagggaca cgccaagaa cacccctgtac    240 ctgcagctga acagcctgaa gaccgaggac accgccatct actactgcgc caagaggatc    300
gactgcaaca gcggctactg ctacaggagg aactactggg gccagggcac ccaggtgacc    360
gtgagcagc                                                             369

<210> SEQ ID NO 105
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
caggtgcagc tgcaggagag cggcggcggc agcgtgcagg tgggcggcag cctgaggctg     60
agctgcgccg ccagcggctt caccttcagc agctaccca tgagctgggt gaggcaggcc    120
cccggcaagg gcctggagtg gatcagcacc atcagcgccg gcggcgacac cacccctgtac   180 gccgacagcg tgaagggcag gttcaccagc agcagggaca cgccaagaa cacccctgtac    240 ctgcagctga acagcctgaa gaccgaggac accgccatct actactgcgc caagaggatc    300
```

```
gactgcaaca gcggctactg ctacaggagg aactactggg gccagggcac ccaggtgacc    360
gtgagcagc                                                            369

<210> SEQ ID NO 106
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
caggtgcagc tgcaggagag cggcggcggc agcgtgcaga gcggcggcag cctgaggctg     60
agctgcgccg ccagcggctt cacctacagc accagcaaca gctggatggc ctggttcagg    120
caggcccccg gcaaggagag ggagggcgtg gccgccatct acaccgtggg cggcagcatc    180
ttctacgccg acagcgtgag gggcaggttc accatcagcc aggacgccac caagaacatg    240
ttctacctgc agatgaacac cctgaagccc gaggacaccg ccatgtacta ctgcgccgcc    300
gccagcggca ggctgagggg caagtggttc tggccctacg agtacaacta ctggggccag    360
ggcacccagg tgaccgtgag cagc                                           384

<210> SEQ ID NO 107
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
caggtgcagc tgcaggagag cggcggcggc agcgtgcagg ccggcggcag cctgaggctg     60
agctgcaggg ccagcggcag cacctacagc aactactgcc tgggctggtt caggcagatc    120
accggcaagg agagggaggg cgtggccgtg atcaactggg tgggcggcat gctgtacttc    180
gccgacagcg tgaagggcag gttcaccgtg agccaggacc aggccaagaa caccctgtac    240
ctgcagatga acagcctgaa gcccgaggac accgccatgt actactgcgc cgccgagagc    300
gtgagcagct tcagctgcgg cggctggctg accaggcccg cagggtgcc ctactggggc    360 cagggcaccc aggtgaccgt gagcagc                                        387

<210> SEQ ID NO 108
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
caggtgcagc tgcaggagag cggcggcggc agcgtgcagg ccggcggcag cctgaggctg     60
agctgcaggg ccagcggcag cacctacagc aactactgcc tgggctggtt caggcagagc    120
accggcaagg agagggaggg cgtggccgtg atcaactggg tgggcggcat gctgtacttc    180
gccgacagcg tgaagggcag gttcaccgtg agccaggacc acgccaagaa caccgtgacc    240
ctgcagatga acagcctgaa gcccgaggac accgccatgt actactgcgc cgccgagagc    300
gtgagcagct tcagctgcgg cggctggctg accaggcccg cagggtgcc ctactggggc    360 cagggcaccc aggtgaccgt gagcagc                                        387
```

<210> SEQ ID NO 109
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
caggtgcagc tgcaggagag cggcggcggc agcgtgcagg ccggcgagag cctgaggctg    60
agctgcaggg ccagcggcag cacctacagc aactactgcc tgggctggtt caggcagatc   120
accggcaagg agagggaggg cgtggccgtg atcaactggg tgggcggcat gctgtacttc   180
gccgacagcg tgaagggcag gttcaccgtg agccaggacc aggccaagaa caccgtgtac   240
ctggagatga acagcctgaa gcccgaggac accgccatgt actactgcgc caccgagagc   300
gtgagcagct tcagctgcgg cggctggctg accaggcccg acagggtgcc ctactgggc   360 cagggcaccc aggtgaccgt gagcagc                                       387

<210> SEQ ID NO 110
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
caggtgcagc tgcaggagag cggcggcggc agcgtgcagg ccggcggcag cctgaggctg    60
agctgcgtgg ccagcggcta cgtgagctgc gactacttcc tgcccagctg gtacaggcag   120
gcccccggca aggagaggga gttcgtgagc atcatcgacg gcaccggcag caccagctac   180
gccgccagcg tgaagggcag gttcaccgcc agccaggaca ggggcaagaa catcgcctac   240
ctgcagatga acagcctgaa gcccgaggac accgccatgt actactgcaa ggccagctgc   300
gtgaggggca ggaccatcag cgagtactgg ggccagggca cccaggtgac cgtgagcagc   360

<210> SEQ ID NO 111
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
caggtgcagc tgcaggagag cggcggcggc agcgtgcagg ccggcggcag cctgaggctg    60
agctgcgtgg ccagcggcta cgtgagctgc gactacttcc tgcccagctg gtacaggcag   120
gcccccggca aggagaggga gttcgtgagc atcatcgacg gcaccggcag caccagctac   180
gccgccagcg tgaagggcag gttcaccgcc agccaggaca gggcaagaa catcgcctac    240 ctgcagatga acagcctgaa gcccgaggac accgccatgt actactgcaa ggccagctgc   300
gtgaggggca gggccatcag cgagtactgg ggccagggca cccaggtgac cgtgagcagc   360

<210> SEQ ID NO 112
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
caggtgcagc tgcaggagag cggcggcggc agcgtgcagg ccggcggcag cctgaggctg      60
agctgcgtgg ccagcggcta cgtgagctgc gactacttcc tgcccagctg gtacaggcag     120
gcccccggca aggagaggga gttcgtgagc atcatcgacg gcaccggcag caccagctac     180
gccgccagcg tgaagggcag gttcaccgcc agccaggaca agggcaagaa catcgcctac     240
ctgcagatga cacccctgaa gcccgaggac accgccatgt actactgcaa ggccagctgc     300
gtgaggggca gggccatcag cgagtactgg ggccagggca cccaggtgac cgtgagcagc     360
```

<210> SEQ ID NO 113
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
caggtgcagc tgcaggagag cggcggcggc agcgtgcagg ccggcggcag cctgaggctg      60
agctgcaggg ccagcggcag cacctacagc aactactgcc tgggctggtt caggcagatc     120
accggcaagg agagggaggg cgtggccgtg atcaactggg tgggcggcat gctgtacttc     180
gccgacagcg tgaagggcag gttcaccgtg agccaggacc aggccaagaa caccgtgtac     240
ctgcagatga cagcctgaa gcccgaggac accgccatgt actactgcgc cgccgagagc     300
gccagcagct tcagctgcgg cggctggctg accaggcccg acagggtgcc ctactggggc     360
cagggcaccc aggtgaccgt gagcagc                                         387
```

<210> SEQ ID NO 114
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
caggtgcagc tgcaggagag cggcggcggc ctggtgcagc ccggcggcag cctgaggctg      60
agctgcgccg ccagcggctt caccttcagc ctgagcggca tgagctgggt gaggcaggcc     120
cccggcaagg gcctggagtg ggtgagcgcc atcagcagcg gcggcgccag cacctactac     180
accgacagcg tgaagggcag gttcaccatc agcagggaca cgccaagaa catgctgtac     240
ctgcagctga cagcctgaa gaccgaggac accgccatgt actactgcgc caagggcggc     300
agcggctacg gcgacgccag caggatgacc agccccggca gccagggcac ccaggtgacc     360
gtgagcagc                                                             369
```

<210> SEQ ID NO 115
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
caggtgcagc tgcaggagag cggcggcggc agcgtgcagg ccggcggcag cctgaggctg      60
agctgcgtgg ccagcggcta cgtgagctgc gactacttcc tgcccagctg gtacaggcag     120
```

```
gcccccggca aggagaggga gttcgtgagc atcatcgacg gcaccggcag caccagctac    180
gccgccagcg tgaagggcag gttcaccgcc agccaggaca agggcaagaa catcgcctac    240
ctgcagatga acagcctgaa gcccgaggac accgccatgt actactgcaa ggccagctgc    300
gtgaggggca gggcatcag cgagtactgg ggccagggca cccaggtgac cgtgagcagc     360
```

<210> SEQ ID NO 116
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
caggtgcagc tgcaggagag cggcggcggc agcgtgcagg ccggcggcag cctgaggctg    60
agctgcaggg ccagcggcag cacctacagc aactactgcc tgggctggtt caggcagatc   120
accggcaagg agagggaggg cgtggccgtg atcaactggg tgggcggcat gctgtacttc   180
gccgacagcg tgaagggcag gttcaccgtg agccaggacc aggccaagaa caccgtgtac   240
ctgcagatga acagcctgaa gcccgaggac accgccatgt actactgcgc cgccgagagc   300
gtgagcagct tcagctgcgg cggctggctg accaggcccg acagggtgcc ctactgggc   360 cagggcaccc aggtgaccgt gagcagc                                       387
```

<210> SEQ ID NO 117
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
caggtgcagc tgcaggagag cggcggcggc ctggtgcagc ccggcggcag cctgaggctg    60
agctgcgccg ccagcggctt caccttcagc agctacccca tgagctgggt gaggcaggcc   120
cccggcaagg gcctggagtg ggtgagcacc atcagcagcg gcggcgacac caccctgtac   180
gccgacagcg tgaagggcag gttcaccagc agcagggaca acgccaagaa cccctgtac   240 ctgcagctga acagcctgaa gaccgaggac accgccatgt actactgcgc caagaggatc   300
gactgcaaca gcggctactg ctacaagagg agctactggg gccagggcac ccaggtgacc   360
gtgagcagc                                                           369
```

<210> SEQ ID NO 118
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
caggtgcagc tgcaggagag cggcggcggc ctggtgcagc ccggcggcag cctgaggctg    60
agctgcgccg ccagcggctt caccttcagc ctgagcagca tgagctgggt gaggcaggcc   120
cccggcaagg gcctggagtg ggtgagcgcc atcagcagcg gcggcgccag cacctactac   180
accgacagcg tgaagggcag gttcaccatc agcagggaca acgccaagaa catgctgtac   240
ctgcagctga acagcctgaa gaccgaggac accgccatgt actactgcgc caagggcggc   300
```

```
agcggctacg gcgacgccag caggatgacc agccccggca gccagggcac ccaggtgacc    360
gtgagcagc                                                            369
```

<210> SEQ ID NO 119
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
caggtgcagc tgcaggagag cggcggcggc agcgtgcagg ccggcggcag cctgaggctg    60
agctgcaggg ccagcggcag cacctacagc aactactgcc tgggctggtt caggcagacc    120
accggcaagg agagggaggg cgtggccgtg atcaactggg tgggcggcat gctgtacttc    180
gccgacagcg tgaagggcag gttcaccgtg agccaggacc aggccaagaa caccgtgtac    240
ctgcagatga acagcctgaa gcccgaggac accgccatgt actactgcgc cgccgagagc    300
gtgagcagct tcagctgcgg cggctggctg accaggcccg acagggtgcc ctactggggc    360
cagggcaccc aggtgaccgt gagcagc                                        387
```

<210> SEQ ID NO 120
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
caggtgcagc tgcaggagag cggcggcggc agcgtgcagg ccggcggcag cctgaggctg    60
agctgcaggg ccagcaggag cccctacggc aactactgcc tgggctggtt caggcagagc    120
accggcaagg agagggaggg cgtggccgtg atcaactggg tgggcggcat gctgtacttc    180
gccgacagcg tgaagggcag gttcaccgtg agccaggacc acgccaagaa caccgtgacc    240
ctgcagatga acagcctgaa gcccgaggac accgccatgt actactgcgc cgccgagagc    300
gtgagcagct tcagctgcgg cggctggctg accaggcccg acagggtgcc ctactggggc    360
cagggcaccc aggtgaccgt gagcagc                                        387
```

<210> SEQ ID NO 121
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
caggtgcagc tgcaggagag cggcggcggc ctggtgcagc ccggcggcag cctgaggctg    60
agctgcgccg ccagcggctt caccttcagc cacagcggca tgagctgggt gaggcaggcc    120
cccggcaagg gcctggagtg ggtgagcacc atcaacagcg gcggcgccag cacctactac    180
accgacagcg tgaagggcag gttcaccatc agcagggaca acgccaagaa catgctgtac    240
ctgcagctga acagcctgaa gaccgaggac accgccatgt actactgcgc caagggcggc    300
agcggctacg gcgacgccag caggatgacc agccccggca gccagggcac ccaggtgacc    360
gtgagcagc                                                            369
```

```
<210> SEQ ID NO 122
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Gln Glu Ser Gly Gly Gly Ser Val Gln Ala Gly Gly
1               5                   10                  15

Ser Leu Arg Leu Ser Cys Ala Ala Ser Lys Asn Ser Asn Phe Met Gly
            20                  25                  30

Trp Phe Arg Gln Ala Pro Gly Lys Glu Arg Glu Gly Val Ala Ala Met
        35                  40                  45

Met Thr Lys Asn Asn Asn Thr Tyr Tyr Ala Asp Ser Val Lys Gly Arg
    50                  55                  60

Phe Thr Ile Ser His Asp Asn Ala Lys Asn Thr Val Tyr Leu Gln Met
65                  70                  75                  80

Asp Ser Leu Lys Pro Glu Asp Thr Ala Val Tyr Tyr Cys Ala Ala Val
                85                  90                  95

Tyr Arg Thr Arg Arg Leu Arg Val Leu Glu Ala Ala Asn Phe Asp Tyr
            100                 105                 110

Trp Gly Gln Gly Thr Gln Val Thr Val Ser Ser
        115                 120

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asn Ser Asn Phe Met Gly
1               5

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Met Met Thr Lys Asn Asn Asn Thr Tyr Tyr Ala Asp Ser Val Lys
1               5                   10                  15

Gly

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Val Tyr Arg Thr Arg Arg Leu Arg Val Leu Glu Ala Ala Asn Phe Asp
1               5                   10                  15
```

Tyr

<210> SEQ ID NO 126
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Ser Ser Arg Tyr
            20                  25                  30

Cys Met Gly Trp Phe Arg Gln Thr Pro Gly Lys Lys Arg Glu Gly Val
        35                  40                  45

Ala Ala Ile Tyr Thr Gly Gly Thr Thr Phe Tyr His Gly Ser Val
    50                  55                  60

Lys Gly Arg Phe Thr Ile Ser Gln Asp Asn Thr Thr Asn Thr Val Tyr
65                  70                  75                  80

Leu Gln Met His Asn Leu Lys Pro Glu Asp Thr Ala Met Tyr Tyr Cys
                85                  90                  95

Ala Ala Gly Pro Val Thr Arg Ala Cys Asp Glu Tyr Asn Tyr Trp Gly
            100                 105                 110

Gln Gly Thr Gln Val Thr Val Ser Ser
        115                 120

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Thr Ser Ser Arg Tyr Cys Met Gly
1               5

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Ile Tyr Thr Gly Gly Gly Thr Thr Phe Tyr His Gly Ser Val Lys
1               5                   10                  15

Gly

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Gly Pro Val Thr Arg Ala Cys Asp Glu Tyr Asn Tyr
1               5                   10
```

<210> SEQ ID NO 130
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Gln Val Gln Leu Gln Glu Ser Gly Gly Ser Val Gln Ala Gly Gly
1               5                   10                  15

Ser Leu Arg Leu Ser Cys Ala Gly Ser Gly Tyr Ser Leu Ser Asn Tyr
            20                  25                  30

Cys Met Gly Trp Phe Arg Gln Ala Pro Gly Gln Gly Arg Glu Gly Val
        35                  40                  45

Ala Ser Leu Arg Phe Val Ser Gly Ala Thr Phe Tyr Ala Asp Ser Val
    50                  55                  60

Lys Gly Arg Phe Thr Ile Ala Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Gly Ile Lys Ser Arg Gly Ile Cys Gly Gly Arg Leu Val Asp Val Asp
            100                 105                 110

Phe Gly Asn Trp Gly Gln Gly Thr Gln Val Thr Val Ser Ser
        115                 120                 125
```

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Tyr Ser Leu Ser Asn Tyr Cys Met Gly
1               5
```

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Ser Leu Arg Phe Val Ser Gly Ala Thr Phe Tyr Ala Asp Ser Val Lys
1               5                   10                  15

Gly
```

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

```
Lys Ser Arg Gly Ile Cys Gly Gly Arg Leu Val Asp Val Asp Phe Gly
1               5                   10                  15

Asn

<210> SEQ ID NO 134
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ser Ile Asn Arg Met
            20                  25                  30

Gly Trp Phe Arg Gln Ala Pro Gly Lys Glu Arg Glu Gly Val Ala Ala
        35                  40                  45

Ile Ser Ile Gly Gly Gly Gln Thr Tyr Tyr Ala Asp Ser Val Lys Gly
    50                  55                  60

Arg Phe Thr Ile Ser Gln Asp Asn Ala Lys Asn Thr Val Asp Leu Gln
65                  70                  75                  80

Met Asn Ser Leu Lys Pro Glu Asp Thr Ala Met Tyr Tyr Cys Ala Ala
                85                  90                  95

Gly Leu Val Tyr Gly Glu Ala Trp Leu Asp Ser Arg His Tyr Asn Lys
            100                 105                 110

Trp Gly Gln Gly Thr Gln Val Thr Val Ser Ser
        115                 120

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Ser Ile Asn Arg Met Gly
1               5

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ile Ser Ile Gly Gly Gly Gln Thr Tyr Tyr Ala Asp Ser Val Lys
1               5                   10                  15

Gly

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 137

Gly Leu Val Tyr Gly Glu Ala Trp Leu Asp Ser Arg His Tyr Asn Lys
1               5                   10                  15

<210> SEQ ID NO 138
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Gly Val Ala Ala
        35                  40                  45

Ile Ala Lys Asp Gly Ile Thr Ile His Ala Asp Ser Val Lys Gly Arg
    50                  55                  60

Phe Thr Ile Ser Lys Asp Asn Ala Lys Asn Thr Leu Tyr Leu Gln Met
65                  70                  75                  80

Asn Ser Leu Lys Pro Glu Asp Thr Ala Met Tyr Tyr Cys Ala Ala His
                85                  90                  95

Arg Pro Tyr Gly Pro Pro Leu Asn Pro Arg Trp Tyr Thr Tyr Trp Gly
            100                 105                 110

Gln Gly Thr Gln Val Thr Val Ser Ser
        115                 120

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Ser Thr Tyr Ser Met Gly
1               5

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ile Ala Lys Asp Gly Ile Thr Ile His Ala Asp Ser Val Lys Gly
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

His Arg Pro Tyr Gly Pro Pro Leu Asn Pro Arg Trp Tyr Thr Tyr
1               5                   10                  15

<210> SEQ ID NO 142
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Tyr
            20                  25                  30

Cys Met Ala Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Ala Ser Gly Arg Cys Leu Gly Pro Gly Ile Arg Ser Leu Ile Trp
            100                 105                 110

Gly Gln Gly Thr Gln Val Thr Val Ser Ser
        115                 120

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Tyr Thr Tyr Ser Ser Tyr Cys Met Ala
1               5

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ile Asp Ser Asp Gly Ser Thr Ser Tyr Ala Asp Ser Val Lys Gly
1               5                   10                  15

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ser Gly Arg Cys Leu Gly Pro Gly Ile Arg Ser Leu Ile
1               5                   10

```
<210> SEQ ID NO 146
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Gly Val Ala Ala
        35                  40                  45

Ile Thr Lys Asp Ile Thr Ile His Ala Asp Ser Val Lys Gly Arg Phe
    50                  55                  60

Thr Ile Ser Lys Asp Asn Ala Lys Asn Thr Leu Tyr Leu Gln Met Asn
65                  70                  75                  80

Ser Leu Lys Pro Glu Asp Thr Ala Met Tyr Tyr Cys Ala Ala His Arg
                85                  90                  95

Pro Tyr Gly Pro Pro Leu Asn Pro Arg Trp Tyr Thr Tyr Trp Gly Gln
            100                 105                 110

Gly Thr Gln Val Thr Val Ser Ser
        115                 120

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Ser Thr Tyr Ser Met Gly
1               5

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Ile Thr Lys Asp Ile Thr Ile His Ala Asp Ser Val Lys Gly
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

His Arg Pro Tyr Gly Pro Pro Leu Asn Pro Arg Trp Tyr Thr Tyr
1               5                   10                  15
```

```
<210> SEQ ID NO 150
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Gly Val Ala Ala
        35                  40                  45

Ile Pro Thr Asp Gly Ile Thr Ile His Ala Asp Ser Val Lys Gly Arg
    50                  55                  60

Phe Thr Ile Ser Lys Asp Asn Ala Lys Asn Thr Leu Tyr Leu Gln Met
65                  70                  75                  80

Asn Ser Leu Lys Pro Glu Asp Thr Ala Met Tyr Tyr Cys Ala Ala His
                85                  90                  95

Arg Pro Tyr Gly Pro Pro Leu Asn Pro Arg Trp Tyr Thr Tyr Trp Gly
            100                 105                 110

Gln Gly Thr Gln Val Thr Val Ser Ser
        115                 120

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Ser Thr Tyr Ser Met Gly
1               5

<210> SEQ ID NO 152
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Ile Pro Thr Asp Gly Ile Thr Ile His Ala Asp Ser Val Lys Gly
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His Arg Pro Tyr Gly Pro Pro Leu Asn Pro Arg Trp Tyr Thr Tyr
1               5                   10                  15

<210> SEQ ID NO 154
<211> LENGTH: 121
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Gly Val Ala Ala
        35                  40                  45

Ile Ala Lys Asp Gly Ile Thr Ile His Ala Asp Ser Val Lys Gly Arg
    50                  55                  60

Phe Thr Ile Ser Lys Asp Asn Ala Lys Asn Thr Leu Tyr Leu Gln Met
65                  70                  75                  80

Ser Ser Leu Lys Pro Glu Asp Thr Ala Met Tyr Tyr Cys Ala Ala His
                85                  90                  95

Arg Pro Tyr Gly Pro Pro Leu Asn Pro Arg Trp Tyr Thr Tyr Trp Gly
            100                 105                 110

Gln Gly Thr Gln Val Thr Val Ser Ser
        115                 120

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Ser Thr Tyr Ser Met Gly
1               5

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Ile Ala Lys Asp Gly Ile Thr Ile His Ala Asp Ser Val Lys Gly
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

His Arg Pro Tyr Gly Pro Pro Leu Asn Pro Arg Trp Tyr Thr Tyr
1               5                   10                  15

<210> SEQ ID NO 158
<211> LENGTH: 121
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 158

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Val Ala Ala
        35                  40                  45

Ile Gly Lys Asp Gly Ile Thr Ile His Ala Asp Ser Val Lys Gly Arg
50                  55                  60

Phe Thr Ile Ser Lys Asp Asn Ala Lys Asn Thr Leu Tyr Leu Gln Met
65                  70                  75                  80

Asn Ser Leu Lys Pro Glu Asp Thr Ala Met Tyr Tyr Cys Ala Ala His
                85                  90                  95

Arg Pro Tyr Gly Pro Pro Leu Asn Pro Arg Trp Tyr Thr Tyr Trp Gly
            100                 105                 110

Gln Gly Thr Gln Val Thr Val Ser Ser
        115                 120

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Ser Thr Tyr Ser Met Gly
1               5

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ile Gly Lys Asp Gly Ile Thr Ile His Ala Asp Ser Val Lys Gly
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

His Arg Pro Tyr Gly Pro Pro Leu Asn Pro Arg Trp Tyr Thr Tyr
1               5                   10                  15

<210> SEQ ID NO 162
<211> LENGTH: 120
<212> TYPE: PRT
<213> ORGANISM: Artificial Sequence
<220> FEATURE:
<223> OTHER INFORMATION: Description of Artificial Sequence: Synthetic
```

```
                    polypeptide

<400> SEQUENCE: 162

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Gly Val Ala Ala
        35                  40                  45

Ile Thr Lys Asp Ile Thr Ile His Ala Asp Ser Val Lys Gly Arg Phe
    50                  55                  60

Thr Ile Ser Lys Asp Asn Ala Lys Asn Thr Leu Tyr Leu Gln Met Asn
65                  70                  75                  80

Ser Leu Arg Pro Glu Asp Thr Ala Met Tyr Tyr Cys Ala Ala His Arg
                85                  90                  95

Pro Tyr Gly Pro Pro Leu Asn Pro Arg Trp Tyr Thr Tyr Trp Gly Gln
            100                 105                 110

Gly Thr Gln Val Thr Val Ser Ser
        115                 120

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Ser Thr Tyr Ser Met Gly
1               5

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Ile Thr Lys Asp Ile Thr Ile His Ala Asp Ser Val Lys Gly
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

His Arg Pro Tyr Gly Pro Pro Leu Asn Pro Arg Trp Tyr Thr Tyr
1               5                   10                  15

<210> SEQ ID NO 166
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 166

```
Gln Val Gln Leu Gln Glu Ser Gly Gly Gly Ser Val Gln Thr Gly Gly
1               5                   10                  15

Ser Leu Arg Leu Ser Cys Ala Ala Ser Gly Tyr Ser Ile Asn Arg Met
            20                  25                  30

Ala Trp Phe Arg Gln Ala Pro Gly Lys Glu Arg Glu Gly Val Ala Ala
        35                  40                  45

Ile Ser Ile Gly Gly Asp Arg Thr Tyr Tyr Ala Asp Ser Val Lys Gly
    50                  55                  60

Arg Phe Thr Ile Ser Gln Asp Asn Ala Lys His Thr Val Asp Leu Gln
65                  70                  75                  80

Met Asn Ser Leu Lys Pro Glu Asp Thr Ala Met Tyr Tyr Cys Ala Ala
                85                  90                  95

Gly Leu Val Tyr Gly Glu Ala Trp Leu Asp Ser Arg His Tyr Asn Lys
            100                 105                 110

Trp Gly Gln Gly Thr Gln Val Thr Val Ser Ser
        115                 120
```

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
Tyr Ser Ile Asn Arg Met Ala
1               5
```

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Ala Ile Ser Ile Gly Gly Asp Arg Thr Tyr Tyr Ala Asp Ser Val Lys
1               5                   10                  15

Gly
```

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Gly Leu Val Tyr Gly Glu Ala Trp Leu Asp Ser Arg His Tyr Asn Lys
1               5                   10                  15
```

<210> SEQ ID NO 170
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 170

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ser Ile Asn Arg Met
            20                  25                  30

Gly Trp Phe Arg Gln Ala Pro Gly Lys Glu Arg Glu Gly Val Ala Ala
        35                  40                  45

Ile Ser Ile Gly Gly Gly Arg Thr Tyr Tyr Ala Asp Ser Val Lys Gly
    50                  55                  60

Arg Phe Thr Ile Ser Gln Asp Asn Ala Lys Asn Thr Val Asp Leu Gln
65                  70                  75                  80

Met Asn Ser Leu Lys Pro Glu Asp Thr Ala Met Tyr Tyr Cys Ala Ala
                85                  90                  95

Gly Leu Val Tyr Gly Glu Ala Trp Leu Asp Ser Arg His Tyr Asn Lys
            100                 105                 110

Trp Gly Gln Gly Thr Gln Val Thr Val Ser Ser
        115                 120
```

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

```
Tyr Ser Ile Asn Arg Met Gly
1               5
```

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

```
Ala Ile Ser Ile Gly Gly Gly Arg Thr Tyr Tyr Ala Asp Ser Val Lys
1               5                   10                  15

Gly
```

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Gly Leu Val Tyr Gly Glu Ala Trp Leu Asp Ser Arg His Tyr Asn Lys
1               5                   10                  15
```

<210> SEQ ID NO 174
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Gln Glu Ser Gly Gly Gly Ser Val Gln Ala Gly Gly
1               5                   10                  15

Ser Leu Arg Leu Ser Cys Ala Val Ser Gly Asp Ser Thr Tyr Ser Met
            20                  25                  30

Gly Trp Phe Arg Gln Pro Pro Gly Lys Glu Arg Glu Gly Val Ala Ala
        35                  40                  45

Ile Thr Lys Asp Gly Ile Thr Ile His Ala Asp Ser Val Lys Gly Arg
    50                  55                  60

Phe Thr Ile Ser Gly Asp Asn Ala Lys Asn Thr Leu Tyr Leu Gln Met
65                  70                  75                  80

Asn Asn Leu Lys Pro Glu Asp Thr Ala Met Tyr Tyr Cys Ala Ala His
                85                  90                  95

Arg Pro Tyr Gly Pro Pro Leu Asn Pro Arg Trp Tyr Thr Tyr Trp Gly
            100                 105                 110

Gln Gly Thr Gln Val Thr Val Ser Ser
        115                 120

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Ser Thr Tyr Ser Met
1               5

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Ile Thr Lys Asp Gly Ile Thr Ile His Ala Asp Ser Val Lys Gly
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

His Arg Pro Tyr Gly Pro Pro Leu Asn Pro Arg Trp Tyr Thr Tyr
1               5                   10                  15

<210> SEQ ID NO 178
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178

```
caggtgcagc tgcaggagag cggcggcggc agcgtgcagg ccggcggcag cctgaggctg    60
agctgcgccg ccagcaagaa cagcaacttc atgggctggt tcaggcaggc ccccggcaag   120
gagagggagg gcgtggccgc catgatgacc aagaacaaca cacctacta cgccgacagc   180 gtgaagggca ggttcaccat cagccacgac aacgccaaga acaccgtgta cctgcagatg   240
gacagcctga agcccgagga caccgccgtg tactactgcg ccgccgtgta caggaccagg   300
aggctgaggg tgctggaggc cgccaacttc gactactggg gccagggcac ccaggtgacc   360
gtgagcagc                                                          369
```

<210> SEQ ID NO 179
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179

```
caggtgcagc tgcaggagag cggcggcggc agcgtgcagg ccggcggcag cctgaggctg    60
agctgcaccg ccagcggcta caccagcagc aggtactgca tgggctggtt caggcagacc   120
cccggcaaga gagggaggg cgtggccgcc atctacaccg gcggcggcac caccttctac   180
cacggcagcg tgaagggcag gttcaccatc agccaggaca acaccaccaa caccgtgtac   240
ctgcagatgc acaacctgaa gcccgaggac accgccatgt actactgcgc cgccggcccc   300
gtgaccaggg cctgcgacga gtacaactac tggggccagg gcacccaggt gaccgtgagc   360
agc                                                                363
```

<210> SEQ ID NO 180
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

```
caggtgcagc tgcaggagag cggcggcggc agcgtgcagg ccggcggcag cctgaggctg    60
agctgcgccg gcagcggcta cagcctgagc aactactgca tgggctggtt caggcaggcc   120
cccggccagg gcagggaggg cgtggccagc ctgaggttcg tgagcggcgc caccttctac   180
gccgacagcg tgaagggcag gttcaccatc gcccaggaca cgccaagaa caccctgtac   240 ctgcagatga acagcctgaa gcccgaggac accgccatgt actactgcgg catcaagagc   300
aggggcatct gcggcggcag gctggtggac gtggacttcg gcaactgggg ccagggcacc   360
caggtgaccg tgagcagc                                                378
```

<210> SEQ ID NO 181
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181

```
caggtgcagc tgcaggagag cggcggcggc agcgtgcagg ccggcggcag cctgaggctg    60
agctgcgccg ccagcggcta cagcatcaac aggatgggct ggttcaggca ggccccggc   120
```

| | | |
|---|---|---|
| aaggagaggg agggcgtggc cgccatcagc atcggcggcg gccagaccta ctacgccgac | 180 | |
| agcgtgaagg gcaggttcac catcagccag gacaacgcca agaacaccgt ggacctgcag | 240 | |
| atgaacagcc tgaagcccga ggacaccgcc atgtactact gcgccgccgg cctggtgtac | 300 | |
| ggcgaggcct ggctggacag caggcactac aacaagtggg gccagggcac ccaggtgacc | 360 | |
| gtgagcagc | 369 | |

```
<210> SEQ ID NO 182
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
```

| | | |
|---|---|---|
| caggtgcagc tgcaggagag cggcggcggc agcgtgcagg ccggcggcag cctgaggctg | 60 | |
| agctgcgccg tgagcggcga cagcacctac agcatgggct ggttcaggca gcccccggc | 120 | |
| aaggagaggg agggcgtggc cgccatcgcc aaggacggca tcaccatcca cgccgacagc | 180 | |
| gtgaagggca ggttcaccat cagcaaggac aacgccaaga cacccctgta cctgcagatg | 240 | |
| aacagcctga gcccgagga caccgccatg tactactgcg ccgcccacag gccctacggc | 300 | |
| cccccctga accccaggtg gtacacctac tggggccagg gcacccaggt gaccgtgagc | 360 | |
| agc | 363 | |

```
<210> SEQ ID NO 183
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
```

| | | |
|---|---|---|
| caggtgcagc tgcaggagag cggcggcggc agcgtgcagg ccggcggcag cctgaggctg | 60 | |
| agctgcgccg ccagcggcta cacctacagc agctactgca tggcctggtt caggcaggcc | 120 | |
| cccggcaagg agagggaggg cgtggccgcc atcgacagcg acggcagcac cagctacgcc | 180 | |
| gacagcgtga agggcaggtt caccatcagc aaggacaacg ccaagaacac cctgtacctg | 240 | |
| cagatgaaca gcctgaagcc cgaggacacc gccatgtact actgcgccgc cgccagcggc | 300 | |
| aggtgcctgg ccccggcat caggagcctg atctggggcc agggcacccc ggtgaccgtg | 360 | |
| agcagc | 366 | |

```
<210> SEQ ID NO 184
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184
```

| | | |
|---|---|---|
| caggtgcagc tgcaggagag cggcggcggc agcgtgcagg ccggcggcag cctgaggctg | 60 | |
| agctgcgccg tgagcggcga cagcacctac agcatgggct ggttcaggca gcccccggc | 120 | |
| aaggagaggg agggcgtggc cgccatcacc aaggacatca ccatccacgc cgacagcgtg | 180 | |
| aagggcaggt tcaccatcag caaggacaac gccaagaaca ccctgtacct gcagatgaac | 240 | | agcctgaagc ccgaggacac cgccatgtac tactgcgccg cccacaggcc ctacggcccc    300 cccctgaacc ccaggtggta cacctactgg ggccagggca cccaggtgac cgtgagcagc    360

<210> SEQ ID NO 185
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
caggtgcagc tgcaggagag cggcggcggc agcgtgcagg ccggcggcag cctgaggctg    60
agctgcgccg tgagcggcga cagcacctac agcatgggct ggttcaggca gccccccggc    120
aaggagaggg agggcgtggc cgccatcccc accgacggca tcaccatcca cgccgacagc    180
gtgaagggca ggttcaccat cagcaaggac aacgccaaga cacccctgta cctgcagatg    240
aacagcctga gcccgagga caccgccatg tactactgcg ccgcccacag gccctacggc    300 cccccccctga accccaggtg gtacacctac tggggccagg gcacccaggt gaccgtgagc    360
agc                                                                  363

<210> SEQ ID NO 186
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
caggtgcagc tgcaggagag cggcggcggc agcgtgcagg ccggcggcag cctgaggctg    60
agctgcgccg tgagcggcga cagcacctac agcatgggct ggttcaggca gccccccggc    120
aaggagaggg agggcgtggc cgccatcgcc aaggacggca tcaccatcca cgccgacagc    180
gtgaagggca ggttcaccat cagcaaggac aacgccaaga cacccctgta cctgcagatg    240
agcagcctga gcccgagga caccgccatg tactactgcg ccgcccacag gccctacggc    300 cccccccctga accccaggtg gtacacctac tggggccagg gcacccaggt gaccgtgagc    360
agc                                                                  363

<210> SEQ ID NO 187
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
caggtgcagc tgcaggagag cggcggcggc agcgtgcagg ccggcggcag cctgaggctg    60
agctgcgccg tgagcggcga cagcacctac agcatgggct ggttcaggca gccccccggc    120
aaggagaggg agggcgtggc cgccatcggc aaggacggca tcaccatcca cgccgacagc    180
gtgaagggca ggttcaccat cagcaaggac aacgccaaga cacccctgta cctgcagatg    240
aacagcctga gcccgagga caccgccatg tactactgcg ccgcccacag gccctacggc    300 cccccccctga accccaggtg gtacacctac tggggccagg gcacccaggt gaccgtgagc    360
agc                                                                  363

<210> SEQ ID NO 188
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
caggtgcagc tgcaggagag cggcggcggc agcgtgcagg ccggcggcag cctgaggctg    60
agctgcgccg tgagcggcga cagcacctac agcatgggct ggttcaggca gccccccggc   120
aaggagaggg agggcgtggc cgccatcacc aaggacatca ccatccacgc cgacagcgtg   180
aagggcaggt tcaccatcag caaggacaac gccaagaaca ccctgtacct gcagatgaac   240
agcctgaggc ccgaggacac cgccatgtac tactgcgccg cccacaggcc ctacggcccc   300
cccctgaacc ccaggtggta cacctactgg ggccagggca ccaggtgac cgtgagcagc    360

<210> SEQ ID NO 189
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189
caggtgcagc tgcaggagag cggcggcggc agcgtgcaga ccggcggcag cctgaggctg    60
agctgcgccg ccagcggcta cagcatcaac aggatggcct ggttcaggca ggccccccggc  120 aaggagaggg agggcgtggc cgccatcagc atcggcggcg acaggaccta ctacgccgac   180
agcgtgaagg gcaggttcac catcagccag gacaacgcca gcacaccgt ggacctgcag    240 atgaacagcc tgaagcccga ggacaccgcc atgtactact gcgccgccgg cctggtgtac   300
ggcgaggcct ggctggacag caggcactac aacaagtggg gccagggcac ccaggtgacc   360
gtgagcagc                                                          369

<210> SEQ ID NO 190
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
caggtgcagc tgcaggagag cggcggcggc agcgtgcagg ccggcggcag cctgaggctg    60
agctgcgccg ccagcggcta cagcatcaac aggatgggct ggttcaggca ggccccccggc  120 aaggagaggg agggcgtggc cgccatcagc atcggcggcg caggaccta ctacgccgac    180 agcgtgaagg gcaggttcac catcagccag gacaacgcca gaacaccgt ggacctgcag    240 atgaacagcc tgaagcccga ggacaccgcc atgtactact gcgccgccgg cctggtgtac   300
ggcgaggcct ggctggacag caggcactac aacaagtggg gccagggcac ccaggtgacc   360
gtgagcagc                                                          369

<210> SEQ ID NO 191
<211> LENGTH: 363
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 191

```
caggtgcagc tgcaggagag cggcggcggc agcgtgcagg ccggcggcag cctgaggctg    60
agctgcgccg tgagcggcga cagcacctac agcatgggct ggttcaggca gcccccggc    120
aaggagaggg agggcgtggc cgccatcacc aaggacggca tcaccatcca cgccgacagc   180
gtgaagggca ggttcaccat cagcggcgac aacgccaaga acaccctgta cctgcagatg   240
aacaacctga gcccgagga caccgccatg tactactgcg ccgcccacag gccctacggc    300
ccccccctga accccaggtg gtacacctac tggggccagg gcacccaggt gaccgtgagc   360
agc                                                                 363
```

<210> SEQ ID NO 192
<211> LENGTH: 484
<212> TYPE: PRT
<213> ORGANISM: Homo sapiens

<400> SEQUENCE: 192

```
Gln Gly Ser Ala Gly Pro Leu Gln Cys Tyr Gly Val Gly Pro Leu Gly
1               5                   10                  15

Asp Leu Asn Cys Ser Trp Glu Pro Leu Gly Asp Leu Gly Ala Pro Ser
            20                  25                  30

Glu Leu His Leu Gln Ser Gln Lys Tyr Arg Ser Asn Lys Thr Gln Thr
        35                  40                  45

Val Ala Val Ala Ala Gly Arg Ser Trp Val Ala Ile Pro Arg Glu Gln
    50                  55                  60

Leu Thr Met Ser Asp Lys Leu Leu Val Trp Gly Thr Lys Ala Gly Gln
65                  70                  75                  80

Pro Leu Trp Pro Pro Val Phe Val Asn Leu Glu Thr Gln Met Lys Pro
                85                  90                  95

Asn Ala Pro Arg Leu Gly Pro Asp Val Asp Phe Ser Glu Asp Asp Pro
            100                 105                 110

Leu Glu Ala Thr Val His Trp Ala Pro Pro Thr Trp Pro Ser His Lys
        115                 120                 125

Val Leu Ile Cys Gln Phe His Tyr Arg Arg Cys Gln Glu Ala Ala Trp
    130                 135                 140

Thr Leu Leu Glu Pro Glu Leu Lys Thr Ile Pro Leu Thr Pro Val Glu
145                 150                 155                 160

Ile Gln Asp Leu Glu Leu Ala Thr Gly Tyr Lys Val Tyr Gly Arg Cys
                165                 170                 175

Arg Met Glu Lys Glu Glu Asp Leu Trp Gly Glu Trp Ser Pro Ile Leu
            180                 185                 190

Ser Phe Gln Thr Pro Pro Ser Ala Pro Lys Asp Val Trp Val Ser Gly
        195                 200                 205

Asn Leu Cys Gly Thr Pro Gly Gly Glu Glu Pro Leu Leu Leu Trp Lys
    210                 215                 220

Ala Pro Gly Pro Cys Val Gln Val Ser Tyr Lys Val Trp Phe Trp Val
225                 230                 235                 240

Gly Gly Arg Glu Leu Ser Pro Glu Gly Ile Thr Cys Cys Cys Ser Leu
                245                 250                 255

Ile Pro Ser Gly Ala Glu Trp Ala Arg Val Ser Ala Val Asn Ala Thr
            260                 265                 270

Ser Trp Glu Pro Leu Thr Asn Leu Ser Leu Val Cys Leu Asp Ser Ala
```

```
              275                 280                 285
Ser Ala Pro Arg Ser Val Ala Val Ser Ser Ile Ala Gly Ser Thr Glu
290                 295                 300

Leu Leu Val Thr Trp Gln Pro Gly Pro Gly Glu Pro Leu Glu His Val
305                 310                 315                 320

Val Asp Trp Ala Arg Asp Gly Asp Pro Leu Glu Lys Leu Asn Trp Val
                325                 330                 335

Arg Leu Pro Pro Gly Asn Leu Ser Ala Leu Leu Pro Gly Asn Phe Thr
                340                 345                 350

Val Gly Val Pro Tyr Arg Ile Thr Val Thr Ala Val Ser Ala Ser Gly
                355                 360                 365

Leu Ala Ser Ala Ser Ser Val Trp Gly Phe Arg Glu Glu Leu Ala Pro
370                 375                 380

Leu Val Gly Pro Thr Leu Trp Arg Leu Gln Asp Ala Pro Pro Gly Thr
385                 390                 395                 400

Pro Ala Ile Ala Trp Gly Glu Val Pro Arg His Gln Leu Arg Gly His
                405                 410                 415

Leu Thr His Tyr Thr Leu Cys Ala Gln Ser Gly Thr Ser Pro Ser Val
                420                 425                 430

Cys Met Asn Val Ser Gly Asn Thr Gln Ser Val Thr Leu Pro Asp Leu
                435                 440                 445

Pro Trp Gly Pro Cys Glu Leu Trp Val Thr Ala Ser Thr Ile Ala Gly
450                 455                 460

Gln Gly Pro Pro Gly Pro Ile Leu Arg Leu His Leu Pro Asp Asn Thr
465                 470                 475                 480

Leu Arg Trp Lys

<210> SEQ ID NO 193
<211> LENGTH: 623
<212> TYPE: PRT
<213> ORGANISM: Mus sp.

<400> SEQUENCE: 193

Met Asn Arg Leu Arg Val Ala Arg Leu Thr Pro Leu Glu Leu Leu
1               5                   10                  15

Ser Leu Met Ser Leu Leu Gly Thr Arg Pro His Gly Ser Pro Gly
                20                  25                  30

Pro Leu Gln Cys Tyr Ser Val Gly Pro Leu Gly Ile Leu Asn Cys Ser
                35                  40                  45

Trp Glu Pro Leu Gly Asp Leu Glu Thr Pro Val Leu Tyr His Gln
50                  55                  60

Ser Gln Lys Tyr His Pro Asn Arg Val Trp Glu Val Lys Val Pro Ser
65                  70                  75                  80

Lys Gln Ser Trp Val Thr Ile Pro Arg Glu Gln Phe Thr Met Ala Asp
                85                  90                  95

Lys Leu Leu Ile Trp Gly Thr Gln Lys Gly Arg Pro Leu Trp Ser Ser
                100                 105                 110

Val Ser Val Asn Leu Glu Thr Gln Met Lys Pro Asp Thr Pro Gln Ile
                115                 120                 125

Phe Ser Gln Val Asp Ile Ser Glu Glu Ala Thr Leu Glu Ala Thr Val
                130                 135                 140

Gln Trp Ala Pro Pro Val Trp Pro Gln Lys Val Leu Ile Cys Gln
145                 150                 155                 160

Phe Arg Tyr Lys Glu Cys Gln Ala Glu Thr Trp Thr Arg Leu Glu Pro
```

```
                165                 170                 175
Gln Leu Lys Thr Asp Gly Leu Thr Pro Val Glu Met Gln Asn Leu Glu
            180                 185                 190

Pro Gly Thr Cys Tyr Gln Val Ser Gly Arg Cys Gln Val Glu Asn Gly
        195                 200                 205

Tyr Pro Trp Gly Glu Trp Ser Ser Pro Leu Ser Phe Gln Thr Pro Phe
    210                 215                 220

Leu Asp Pro Glu Asp Val Trp Val Ser Gly Thr Val Cys Glu Thr Ser
225                 230                 235                 240

Gly Lys Arg Ala Ala Leu Leu Val Trp Lys Asp Pro Arg Pro Cys Val
                245                 250                 255

Gln Val Thr Tyr Thr Val Trp Phe Gly Ala Gly Asp Ile Thr Thr Thr
            260                 265                 270

Gln Glu Glu Val Pro Cys Cys Lys Ser Pro Val Pro Ala Trp Met Glu
        275                 280                 285

Trp Ala Val Val Ser Pro Gly Asn Ser Thr Ser Trp Val Pro Pro Thr
    290                 295                 300

Asn Leu Ser Leu Val Cys Leu Ala Pro Glu Ser Ala Pro Cys Asp Val
305                 310                 315                 320

Gly Val Ser Ser Ala Asp Gly Ser Pro Gly Ile Lys Val Thr Trp Lys
                325                 330                 335

Gln Gly Thr Arg Lys Pro Leu Glu Tyr Val Val Asp Trp Ala Gln Asp
            340                 345                 350

Gly Asp Ser Leu Asp Lys Leu Asn Trp Thr Arg Leu Pro Pro Gly Asn
        355                 360                 365

Leu Ser Thr Leu Leu Pro Gly Glu Phe Lys Gly Val Pro Tyr Arg
    370                 375                 380

Ile Thr Val Thr Ala Val Tyr Ser Gly Gly Leu Ala Ala Ala Pro Ser
385                 390                 395                 400

Val Trp Gly Phe Arg Glu Glu Leu Val Pro Leu Ala Gly Pro Ala Val
                405                 410                 415

Trp Arg Leu Pro Asp Asp Pro Pro Gly Thr Pro Val Val Ala Trp Gly
            420                 425                 430

Glu Val Pro Arg His Gln Leu Arg Gly Gln Ala Thr His Tyr Thr Phe
        435                 440                 445

Cys Ile Gln Ser Arg Gly Leu Ser Thr Val Cys Arg Asn Val Ser Ser
    450                 455                 460

Gln Thr Gln Thr Ala Thr Leu Pro Asn Leu His Leu Gly Ser Phe Lys
465                 470                 475                 480

Leu Trp Val Thr Val Ser Thr Val Ala Gly Gln Gly Pro Pro Gly Pro
                485                 490                 495

Asn Leu Ser Leu His Leu Pro Asp Asn Arg Ile Arg Trp Lys Ala Leu
            500                 505                 510

Pro Trp Phe Leu Ser Leu Trp Gly Leu Leu Met Gly Cys Gly Leu
        515                 520                 525

Ser Leu Ala Ser Thr Arg Cys Leu Gln Ala Arg Cys Leu His Trp Arg
    530                 535                 540

His Lys Leu Leu Pro Gln Trp Ile Trp Glu Arg Val Pro Asp Pro Ala
545                 550                 555                 560

Asn Ser Asn Ser Gly Gln Pro Tyr Ile Lys Glu Val Ser Leu Pro Gln
                565                 570                 575

Pro Pro Lys Asp Gly Pro Ile Leu Glu Val Glu Val Glu Leu Gln
            580                 585                 590
```

```
Pro Val Val Glu Ser Pro Lys Ala Ser Ala Pro Ile Tyr Ser Gly Tyr
        595                 600                 605

Glu Lys His Phe Leu Pro Thr Pro Glu Glu Leu Gly Leu Leu Val
    610                 615                 620

<210> SEQ ID NO 194
<211> LENGTH: 486
<212> TYPE: PRT
<213> ORGANISM: Mus sp.

<400> SEQUENCE: 194

Thr Arg Pro His Gly Ser Pro Gly Pro Leu Gln Cys Tyr Ser Val Gly
1               5                   10                  15

Pro Leu Gly Ile Leu Asn Cys Ser Trp Glu Pro Leu Gly Asp Leu Glu
            20                  25                  30

Thr Pro Pro Val Leu Tyr His Ser Gln Lys Tyr His Pro Asn Arg
        35                  40                  45

Val Trp Glu Val Lys Val Pro Ser Lys Gln Ser Trp Val Thr Ile Pro
    50                  55                  60

Arg Glu Gln Phe Thr Met Ala Asp Lys Leu Leu Ile Trp Gly Thr Gln
65                  70                  75                  80

Lys Gly Arg Pro Leu Trp Ser Ser Val Ser Val Asn Leu Glu Thr Gln
                85                  90                  95

Met Lys Pro Asp Thr Pro Gln Ile Phe Ser Gln Val Asp Ile Ser Glu
            100                 105                 110

Glu Ala Thr Leu Glu Ala Thr Val Gln Trp Ala Pro Pro Val Trp Pro
        115                 120                 125

Pro Gln Lys Val Leu Ile Cys Gln Phe Arg Tyr Lys Glu Cys Gln Ala
    130                 135                 140

Glu Thr Trp Thr Arg Leu Glu Pro Gln Leu Lys Thr Asp Gly Leu Thr
145                 150                 155                 160

Pro Val Glu Met Gln Asn Leu Glu Pro Gly Thr Cys Tyr Gln Val Ser
                165                 170                 175

Gly Arg Cys Gln Val Glu Asn Gly Tyr Pro Trp Gly Glu Trp Ser Ser
            180                 185                 190

Pro Leu Ser Phe Gln Thr Pro Phe Leu Asp Pro Glu Asp Val Trp Val
        195                 200                 205

Ser Gly Thr Val Cys Glu Thr Ser Gly Lys Arg Ala Ala Leu Leu Val
    210                 215                 220

Trp Lys Asp Pro Arg Pro Cys Val Gln Val Thr Tyr Thr Val Trp Phe
225                 230                 235                 240

Gly Ala Gly Asp Ile Thr Thr Gln Glu Glu Val Pro Cys Cys Lys
                245                 250                 255

Ser Pro Val Pro Ala Trp Met Glu Trp Ala Val Val Ser Pro Gly Asn
            260                 265                 270

Ser Thr Ser Trp Val Pro Pro Thr Asn Leu Ser Leu Val Cys Leu Ala
        275                 280                 285

Pro Glu Ser Ala Pro Cys Asp Val Gly Val Ser Ser Ala Asp Gly Ser
    290                 295                 300

Pro Gly Ile Lys Val Thr Trp Lys Gln Gly Thr Arg Lys Pro Leu Glu
305                 310                 315                 320

Tyr Val Val Asp Trp Ala Gln Asp Gly Asp Ser Leu Asp Lys Leu Asn
                325                 330                 335

Trp Thr Arg Leu Pro Pro Gly Asn Leu Ser Thr Leu Leu Pro Gly Glu
```

```
                    340                 345                 350
Phe Lys Gly Gly Val Pro Tyr Arg Ile Thr Val Thr Ala Val Tyr Ser
                355                 360                 365
Gly Gly Leu Ala Ala Pro Ser Val Trp Gly Phe Arg Glu Glu Leu
        370                 375                 380
Val Pro Leu Ala Gly Pro Ala Val Trp Arg Leu Pro Asp Asp Pro
385                 390                 395                 400
Gly Thr Pro Val Val Ala Trp Gly Glu Val Pro Arg His Gln Leu Arg
                405                 410                 415
Gly Gln Ala Thr His Tyr Thr Phe Cys Ile Gln Ser Arg Gly Leu Ser
                420                 425                 430
Thr Val Cys Arg Asn Val Ser Ser Gln Thr Gln Thr Ala Thr Leu Pro
        435                 440                 445
Asn Leu His Leu Gly Ser Phe Lys Leu Trp Val Thr Val Ser Thr Val
        450                 455                 460
Ala Gly Gln Gly Pro Pro Gly Pro Asn Leu Ser Leu His Leu Pro Asp
465                 470                 475                 480
Asn Arg Ile Arg Trp Lys
                485

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 195

His His His His His His
1               5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 196

His His His His His His His His
1               5

<210> SEQ ID NO 197
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 197

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30
```

Gly Gly Gly Ser Gly Gly Gly Ser
         35                  40

<210> SEQ ID NO 198
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Ser Gly" repeating units

<400> SEQUENCE: 198

Gly Gly Gly Ser Gly Gly Gly Ser Gly Gly Gly Ser Gly Gly
1               5                   10                  15

Gly Gly Ser Gly Gly Gly Gly Ser Gly Gly Gly Ser Gly Gly
            20                  25                  30

Gly Ser Gly Gly Gly Gly Ser Gly Gly Gly Ser Gly Gly Gly
        35                  40                  45

Ser Gly
    50

<210> SEQ ID NO 199
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Gly Ser" repeating units

<400> SEQUENCE: 199

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly
            20                  25                  30

Gly Gly Ser Gly Gly Gly Gly Ser Gly Gly Gly Ser Gly Gly
        35                  40                  45

Gly Ser
    50

<210> SEQ ID NO 200
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 1-10 "Gly Gly Ser"
      repeating units

<400> SEQUENCE: 200

Gly Gly Ser Gly Gly Ser Gly Gly Ser Gly Gly Ser Gly Gly Ser
1               5                   10                  15

Gly Ser Gly Gly Ser Gly Gly Ser Gly Gly Ser Gly Gly Ser Gly

```
<210> SEQ ID NO 201
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 201

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(6)
<223> OTHER INFORMATION: This sequence may encompass 3-6 residues

<400> SEQUENCE: 202

His His His His His His
1               5
```

IL27RALPHA BINDING MOLECULES AND METHODS OF USE

CROSS-REFERENCES TO RELATED APPLICATIONS

This application is a U.S. National phase of PCT Patent Application No. PCT/US2021/044576, filed, Aug. 4, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 20, 2023, is named 106249-1364210-Sequence-Listing.txt and is 125,573 bytes in size.

FIELD OF THE INVENTION

The present disclosure relates to biologically active molecules comprising a single domain antibody that specifically binds to the extracellular domain of the IL27 receptor alpha (IL27Rα), compositions comprising such single domain antibodies, and methods of use thereof.

BACKGROUND

The cytokine IL-27 is a heterodimeric cytokine consisting out of two non-covalently linked subunits, p28 and EBI3. The p28 subunit belongs to the 4-helix bundle cytokine family, while EBI3 is the shortest form possible of a soluble cytokine receptor, with two typical cytokine binding domains (Pflanz S, et al., Immunity. 2002 June; 16(6):779-90).

The interleukin-27 receptor (IL27R) is a type I cytokine receptor for interleukin-27 (IL27). IL27R is a heterodimer composed of the IL27Rα subunit and glycoprotein 130 (IL6Rb). IL27 is expressed by antigen presenting cells and induces differentiation of a diverse populations of T cells in the immune system. The binding of IL27 to IL27R initiates intracellular signaling several Jak family kinases which induce phosphorylation of STAT1 and STAT3. In activated T cells, IL27 predominantly signals through STAT3 [23], while in memory B cells it signals predominately through STAT3. IL27 has been shown to have both proinflammatory and anti-inflammatory properties and that the pro- or anti-inflammatory response is influenced by the context of the cell expressing the IL27R.

IL27Rα subunit (also known as TCCR- or WSX-1 receptor) is the proprietary subunit of the IL27 receptor. The mature (less signal peptide) IL27Rα is a 604 amino acid polypeptide with a 484 amino acid extracellular domain. The extracellular domain of IL27Rα has 5 domains: D1-D5. D1 and D2 are the primary cytokine binding domains while the fibronectin type III (Fn3) domains D3, D4 and D5 are involved in ligand recognition to a much lesser extent. Based on structural analyses, the Fn3 domains do not contribute to binding in the complex when IL27 ligand is bound. While domains D1 and D2 are highly conserved, the sequence of the Fn3 domains are more variable.

The IL27 demonstrates high (nanomolar) affinity for the IL27Ra subunit. The [IL27/IL27Rα] complex associates with IL27Ra to complete the IL27 receptor signaling complex. The binding of gp130 to the to the [IL27/IL27Rα] complex is much weaker than the interaction between IL-27 and IL-27R. (Pflanz S, et al., J Immunol. 2004 Feb. 15; 172(4):2225-31) which is somewhat conventional with respect to shared cytokine receptor subunits. The D5 domain of IL-27R and the D6 domain of gp130 come close together at the membrane because of the 'C' shape of each receptor. This is required for the receptor complex to trigger binding of JAKs at the intracellular domains of both receptors.

Although monoclonal antibodies are the most widely used reagents for the detection and quantification of proteins, monoclonal antibodies are large molecules of about 150 kDa and their size could potentially limit their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicunas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents.

SUMMARY OF THE INVENTION

The present disclosure provides polypeptides that specifically bind to IL27Ra.

The present disclosure provides polypeptides that specifically bind to the extracellular domain of IL27Ra.

The present disclosure provides a IL27Ra binding molecule that specifically bind to the extracellular domain of human IL27Ra (hIL27Ra).

In some embodiments, the IL27Ra binding molecule comprises a single domain antibody (sdAb) that specifically binds to the extracellular domain of the human IL27Ra.

In some embodiments, the IL27Ra binding molecule is a sdAb, the sdAb comprising a set of CDRs corresponding to CDR1, CDR2, and CDR3 as shown in a row of Table 1 below.

In some embodiments, the IL27Ra binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IL27Ra binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that are optionally are conservative amino acid substitutions) or 100% identity to a polypeptide sequence of any one of SEQ ID NOS: 2-25, as shown in Table 1 below.

TABLE 1

| Name | VHH Sequence (CDRs underlined) | CDR1 | CDR2 | CDR3 |
|---|---|---|---|---|
| hIL27Ra VHH1 | QVQLQESGGGLVQPGGSLRLSCAAS GFTFSSYPMSWVRQAPGKGLEWIST ISAGGDTTLYADSVKGRFTSSRDNA KNTLYLQLNSLKTEDAAIYYCAKRI DCNSGYCYRRNYWGQGTQVTVSS (SEQ ID NO: 2) | FTFSSYPMS (SEQ ID NO: 26) | TISAGGDTT LYADSVKG (SEQ ID NO: 27) | RIDCNSGYC YRRNY (SEQ ID NO: 28) |
| hIL27Ra VHH2 | QVQLQESGGGLVQPGGSLRLSCAAS GFTFSLSGMSWVRQAPGKGLEWVS AISSGGASTYYTDSVKGRFTISRDNA KNILYLQLNSLKTEDTAMYYCAKG GSGYGDASRMTSPGSQGTQVTVSS (SEQ ID NO: 3) | FTFSLSGMS (SEQ ID NO: 29) | AISSGGAST YYTDSVKG (SEQ ID NO: 30) | GGSGYGDAS RMTSP (SEQ ID NO: 31) |
| hIL27Ra VHH3 | QVQLQESGGGSVQAGGSLRLSCVAS GYVSCDYFLPSWYRQAPGKEREFVS IIDGTGSTSYAASVKGRFTASEDKGK NIAYLQMNSLKPEDTAMYYCKASC VRGRAVSEYWGQGTQVTVSS (SEQ ID NO: 4) | YVSCDYFLPS (SEQ ID NO: 32) | IIDGTGSTSY AASVKG (SEQ ID NO: 33) | SCVRGRAVS EY (SEQ ID NO: 34) |
| hIL27Ra VHH4 | QVQLQESGGGLVQPGESLRLSCTAS GFTFSNYAMSWVRQAPGKGLEWVS GINVAYGITSYADSVKGRFTISRDNT KNTLYLQLNSLKTEDTAIYYCVKHS GTTIPRGFISYTKRGQGTQVTVSS (SEQ ID NO: 5) | FTFSNYAMS (SEQ ID NO: 35) | GINVAYGIT SYADSVKG (SEQ ID NO: 36) | HSGTTIPRGFI SYTK (SEQ ID NO: 37) |
| hIL27Ra VHH5 | QVQLQESGGGSVQAGGSLRLSCTAS GYVSCDYFLPSWYRQAPGKEREFVS VIDGTGSTSYAASVKGRFTASQDKG KNIAYLQMNSLKPEDTAMYYCKAS CVRGRAISEYWGQGTQVTVSS (SEQ ID NO: 6) | YVSCDYFLPS (SEQ ID NO: 38) | VIDGTGSTS YAASVKG (SEQ ID NO: 39) | SCVRGRAISE Y (SEQ ID NO: 40) |
| hIL27Ra VHH6 | QVQLQESGGGLVQPGGSLRLSCAAS GFSFSSYAMKWVRQAPGKGLEWVS TISSGGSSTNYADSVKGRFTISRDNA KNTLYLQLNSLKIEDTAMYYCAKAI VPTGATMERGQGTQVTVSS (SEQ ID NO: 7) | FSFSSYAMK (SEQ ID NO: 41) | TISSGGSSTN YADSVKG (SEQ ID NO: 42) | AIVPTGATM E (SEQ ID NO: 43) |
| hIL27Ra VHH7 | QVQLQESGGGLVQPGGSLRLSCAAS GFTFSSYPMSWVRQAPGKGLEWIST ISAGGDTTLYADSVKGRFTSSRDNA KNTLYLQLNSLKTEDTAIYYCAKRI DCNSGYCYRRNYWGQGTQVTVSS (SEQ ID NO: 8) | FTFSSYPMS (SEQ ID NO: 44) | TISAGGDTT LYADSVKG (SEQ ID NO: 45) | RIDCNSGYC YRRNY (SEQ ID NO: 46) |
| hIL27Ra VHH8 | QVQLQESGGGSVQVGGSLRLSCAAS GFTFSSYPMSWVRQAPGKGLEWIST ISAGGDTTLYADSVKGRFTSSRDNA KNTLYLQLNSLKTEDTAIYYCAKRI DCNSGYCYRRNYWGQGTQVTVSS (SEQ ID NO: 9) | FTFSSYPMS (SEQ ID NO: 47) | TISAGGDTT LYADSVKG (SEQ ID NO: 48) | RIDCNSGYC YRRNY (SEQ ID NO: 49) |
| hIL27Ra VHH9 | QVQLQESGGGSVQSGGSLRLSCAAS GFTYSTSNSWMAWFRQAPGKEREG VAAIYTVGGSIFYADSVRGRFTISQD ATKNMFYLQMNTLKPEDTAMYYC AAASGRLRGKWFWPYEYNYWGQG TQVTVSS (SEQ ID NO: 10) | FTYSTSNSWM A (SEQ ID NO: 50) | AIYTVGGSIF YADSVRG (SEQ ID NO: 51) | ASGRLRGKW FWPYEYNY (SEQ ID NO: 52) |

TABLE 1-continued

| Name | VHH Sequence (CDRs underlined) | CDR1 | CDR2 | CDR3 |
|---|---|---|---|---|
| hIL27Ra VHH10 | QVQLQESGGGSVQAGGSLRLSCRAS GSTYSNYCLGWFRQITGKEREGVAV INWVGGMLYFADSVKGRFTVSQDQ AKNTLYLQMNSLKPEDTAMYYCAA ESVSSFSCGGWLTRPDRVPYWGQG TQVTVSS (SEQ ID NO: 11) | STYSNYCLG (SEQ ID NO: 53) | VINWVGGM LYFADSVKG (SEQ ID NO: 54) | ESVSSFSCGG WLTRPDRVP Y (SEQ ID NO: 55) |
| hIL27Ra VHH11 | QVQLQESGGGSVQAGGSLRLSCRAS GSTYSNYCLGWFRQSTGKEREGVA VINWVGGMLYFADSVKGRFTVSQD HAKNTVTLQMNSLKPEDTAMYYCA AESVSSFSCGGWLTRPGRVPYWGQ GTQVTVSS (SEQ ID NO: 12) | STYSNYCLG (SEQ ID NO: 56) | VINWVGGM LYFADSVKG (SEQ ID NO: 57) | ESVSSFSCGG WLTRPGRVP Y (SEQ ID NO: 58) |
| hIL27Ra VHH12 | QVQLQESGGGSVQAGESLRLSCRAS GSTYSNYCLGWFRQITGKEREGVAV INWVGGMLYFADSVKGRFTVSQDQ AKNTVYLEMNSLKPEDTAMYYCAT ESVSSFSCGGWLTRPDRVPYWGQG TQVTVSS (SEQ ID NO: 13) | STYSNYCLG (SEQ ID NO: 59) | VINWVGGM LYFADSVKG (SEQ ID NO: 60) | ESVSSFSCGG WLTRPDRVP Y (SEQ ID NO: 61) |
| hIL27Ra VHH13 | QVQLQESGGGSVQAGGSLRLSCVAS GYVSCDYFLPSWYRQAPGKEREFVS IIDGTGSTSYAASVKGRFTASQDRG KNIAYLQMNSLKPEDTAMYYCKAS CVRGRTISEYWGQGTQVTVSS (SEQ ID NO: 14) | YVSCDYFLPS (SEQ ID NO: 62) | IIDGTGSTSY AASVKG (SEQ ID NO: 63) | SCVRGRTISE Y (SEQ ID NO: 64) |
| hIL27Ra VHH14 | QVQLQESGGGSVQAGGSLRLSCVAS GYVSCDYFLPSWYRQAPGKEREFVS IIDGTGSTSYAASVKGRFTASQDKG KNIAYLQMNSLKPEDTAMYYCKAS CVRGRAISEYWGQGTQVTVSS (SEQ ID NO: 15) | YVSCDYFLPS (SEQ ID NO: 65) | IIDGTGSTSY AASVKG (SEQ ID NO: 66) | SCVRGRAISE Y (SEQ ID NO: 67) |
| hIL27Ra VHH15 | QVQLQESGGGSVQAGGSLRLSCVAS GYVSCDYFLPSWYRQAPGKEREFVSK IIDGTGSTSYAASVKGRFTASQDKG KNIAYLQMNTLKPEDTAMYYCKAS CVRGRAISEYWGQGTQVTVSS (SEQ ID NO: 16) | YVSCDYFLPS (SEQ ID NO: 68) | IIDGTGSTSY AASVKG (SEQ ID NO: 69) | SCVRGRAISE Y (SEQ ID NO: 70) |
| hIL27Ra VHH16 | QVQLQESGGGSVQAGGSLRLSCRAS GSTYSNYCLGWFRQITGKEREGVAV INWVGGMLYFADSVKGRFTVSQDQ AKNTVYLQMNSLKPEDTAMYYCA AESASSFSCGGWLTRPDRVPYWGQ GTQVTVSS (SEQ ID NO: 17) | STYSNYCLG (SEQ ID NO: 71) | VINWVGGM LYFADSVKG (SEQ ID NO: 72) | ESASSFSCGG WLTRPDRVP Y (SEQ ID NO: 73) |
| hIL27Ra VHH17 | QVQLQESGGGLVQPGGSLRLSCAAS GFTFSLSGMSWVRQAPGKGLEWVS AISSGGASTYYTDSVKGRFTISRDNA KNMLYLQLNSLKTEDTAMYYCAKG GSGYGDASRMTSPGSQGTQVTVSS (SEQ ID NO: 18) | FTFSLSGMS (SEQ ID NO: 74) | AISSGGAST YYTDSVKG (SEQ ID NO: 75) | GGSGYGDAS RMTSP (SEQ ID NO: 76) |
| hIL27Ra VHH18 | QVQLQESGGGSVQAGGSLRLSCVAS GYVSCDYFLPSWYRQAPGKEREFVS IIDGTGSTSYAASVKGRFTASQDKG KNIAYLQMNSLKPEDTAMYYCKAS CVRGRGISEYWGQGTQVTVSS (SEQ ID NO: 19) | YVSCDYFLPS (SEQ ID NO: 77) | IIDGTGSTSY AASVKG (SEQ ID NO: 78) | SCVRGRGISE Y (SEQ ID NO: 79) |
| hIL27Ra VHH19 | QVQLQESGGGSVQAGGSLRLSCRAS GSTYSNYCLGWFRQITGKEREGVAV INWVGGMLYFADSVKGRFTVSQDQ AKNTVYLQMNSLKPEDTAMYYCA AESVSSFSCGGWLTRPDRVPYWGQ GTQVTVSS (SEQ ID NO: 20) | STYSNYCLG (SEQ ID NO: 80) | VINWVGGM LYFADSVKG (SEQ ID NO: 81) | ESVSSFSCGG WLTRPDRVP Y (SEQ ID NO: 82) |

TABLE 1-continued

| Name | VHH Sequence (CDRs underlined) | CDR1 | CDR2 | CDR3 |
|---|---|---|---|---|
| hIL27Ra VHH20 | QVQLQESGGGLVQPGGSLRLSCAAS GFTFSSYPMSWVRQAPGKGLEWVS TISSGGDTTLYADSVKGRFTSSRDN AKNTLYLQLNSLKTEDTAMYYCAK RIDCNSGYCYKRSYWGQGTQVTVS S (SEQ ID NO: 21) | FTFSSYPMS (SEQ ID NO: 83) | TISSGGDTTL YADSVKG (SEQ ID NO: 84) | RIDCNSGYC YKRSY (SEQ ID NO: 85) |
| hIL27Ra VHH21 | QVQLQESGGGLVQPGGSLRLSCAAS GFTFSLSSMSWVRQAPGKGLEWVS AISSGGASTYYTDSVKGRFTISRDNA KNMLYLQLNSLKTEDTAMYYCAKG GSGYGDASRMTSPGSQGTQVTVSS (SEQ ID NO: 22) | FTFSLSSMS (SEQ ID NO: 86) | AISSGGAST YYTDSVKG (SEQ ID NO: 87) | GGSGYGDAS RMTSP (SEQ ID NO: 88) |
| hIL27Ra VHH22 | QVQLQESGGGSVQAGGSLRLSCRAS GSTYSNYCLGWFRQTTGKEREGVA VINWVGGMLYFADSVKGRFTVSQD QAKNTVYLQMNSLKPEDTAMYYC AAESVSSFSCGGWLTRPDRVPYWG QGTQVTVSS (SEQ ID NO: 23) | STYSNYCLG (SEQ ID NO: 89) | VINWVGGM LYFADSVKG (SEQ ID NO: 90) | ESVSSFSCGG WLTRPDRVP Y (SEQ ID NO: 91) |
| hIL27Ra VHH23 | QVQLQESGGGSVQAGGSLRLSCRAS RSPYGNYCLGWFRQSTGKEREGVA VINWVGGMLYFADSVKGRFTVSQD HAKNTVTLQMNSLKPEDTAMYYCA AESVSSFSCGGWLTRPDRVPYWGQ GTQVTVSS (SEQ ID NO: 24) | SPYGNYCLG (SEQ ID NO: 92) | VINWVGGM LYFADSVKG (SEQ ID NO: 93) | ESVSSFSCGG WLTRPDRVP Y (SEQ ID NO: 94) |
| hIL27Ra VHH24 | QVQLQESGGGLVQPGGSLRLSCAAS GFTFSHSGMSWVRQAPGKGLEWVS TINSGGASTYYTDSVKGRFTISRDNA KNMLYLQLNSLKTEDTAMYYCAKG GSGYGDASRMTSPGSQGTQVTVSS (SEQ ID NO: 25) | FTFSHSGMS (SEQ ID NO: 95) | TINSGGAST YYTDSVKG (SEQ ID NO: 96) | GGSGYGDAS RMTSP SEQ ID NO: 97) |

In some embodiments, the foregoing sets of CDRs are incorporated in a humanized VHH framework to provide "humanized" sdAb IL27Ra binding molecules.

The disclosure further provides methods of chemical or recombinant processes for the preparation of the IL27Ra binding molecules of the present disclosure.

The disclosure further provides nucleic acids encoding the IL27Ra binding molecules. Table 2 below provides examples of DNA sequences encoding IL27Ra binding molecules as described herein.

TABLE 2

DNA Sequences Encoding VHHs of Table 1.

| Name | Sequence |
|---|---|
| hIL27Ra VHH1 | CAGGTGCAGCTGCAGGAGAGCGGCGGCGGCCTGGTGCAGCCCGGCGGCA GCCTGAGGCTGAGCTGCGCCGCCAGCGGCTTCACCTTCAGCAGCTACCCC ATGAGCTGGGTGAGGCAGGCCCCCGGCAAGGGCCTGGAGTGGATCAGCA CCATCAGCGCCGGCGGCGACACCACCCTGTACGCCGACAGCGTGAAGGG CAGGTTCACCAGCAGCAGGGACAACGCCAAGAACACCCTGTACCTGCAG CTGAACAGCCTGAAGACCGAGGACGCCGCCATCTACTACTGCGCCAAGA GGATCGACTGCAACAGCGGCTACTGCTACAGGAGGAACTACTGGGGCCA GGGCACCCAGGTGACCGTGAGCAGC (SEQ ID NO: 98) |
| hIL27Ra VHH2 | CAGGTGCAGCTGCAGGAGAGCGGCGGCGGCCTGGTGCAGCCCGGCGGCA GCCTGAGGCTGAGCTGCGCCGCCAGCGGCTTCACCTTCAGCCTGAGCGGC ATGAGCTGGGTGAGGCAGGCCCCCGGCAAGGGCCTGGAGTGGGTGAGCG CCATCAGCAGCGGCGGCGCCAGCACCTACTACACCGACAGCGTGAAGGG CAGGTTCACCATCAGCAGGGACAACGCCAAGAACATCCTGTACCTGCAG |

TABLE 2-continued

DNA Sequences Encoding VHHs of Table 1.

| Name | Sequence |
|---|---|
|  | CTGAACAGCCTGAAGACCGAGGACACCGCCATGTACTACTGCGCCAAGG<br>GCGGCAGCGGCTACGGCGACGCCAGCAGGATGACCAGCCCCGGCAGCCA<br>GGGCACCCAGGTGACCGTGAGCAGC<br>(SEQ ID NO: 99) |
| hIL27Ra VHH3 | CAGGTGCAGCTGCAGGAGAGCGGCGGCGGCAGCGTGCAGGCCGGCGG<br>AGCCTGAGGCTGAGCTGCGTGGCCAGCGGCTACGTGAGCTGCGACTACT<br>TCCTGCCCAGCTGGTACAGGCAGGCCCCCGGCAAGGAGAGGGAGTTCGT<br>GAGCATCATCGACGGCACCGGCAGCACCAGCTACGCCGCCAGCGTGAAG<br>GGCAGGTTCACCGCCAGCGAGGACAAGGGCAAGAACATCGCCTACCTGC<br>AGATGAACAGCCTGAAGCCCGAGGACACCGCCATGTACTACTGCAAGGC<br>CAGCTGCGTGAGGGGCAGGGCCGTGAGCGAGTACTGGGGCCAGGGCACC<br>CAGGTGACCGTGAGCAGC<br>(SEQ ID NO: 100) |
| hIL27Ra VHH4 | CAGGTGCAGCTGCAGGAGAGCGGCGGCGGCCTGGTGCAGCCCGGCGAGA<br>GCCTGAGGCTGAGCTGCACCGCCAGCGGCTTCACCTTCAGCAACTACGCC<br>ATGAGCTGGGTGAGGCAGGCCCCCGGCAAGGGCCTGGAGTGGGTGAGCG<br>GCATCAACGTGGCCTACGGCATCACCAGCTACGCCGACAGCGTGAAGGG<br>CAGGTTCACCATCAGCAGGGACAACACCAAGAACACCCTGTACCTGCAG<br>CTGAACAGCCTGAAGACCGAGGACACCGCCATCTACTACTGCGTGAAGC<br>ACAGCGGCACCACCATCCCCAGGGGCTTCATCAGCTACACCAAGAGGGG<br>CCAGGGCACCCAGGTGACCGTGAGCAGC<br>(SEQ ID NO: 101) |
| hIL27Ra VHH5 | CAGGTGCAGCTGCAGGAGAGCGGCGGCGGCAGCGTGCAGGCCGGCGGC<br>AGCCTGAGGCTGAGCTGCACCGCCAGCGGCTACGTGAGCTGCGACTACT<br>TCCTGCCCAGCTGGTACAGGCAGGCCCCCGGCAAGGAGAGGGAGTTCGT<br>GAGCGTGATCGACGGCACCGGCAGCACCAGCTACGCCGCCAGCGTGAAG<br>GGCAGGTTCACCGCCAGCCAGGACAAGGGCAAGAACATCGCCTACCTGC<br>AGATGAACAGCCTGAAGCCCGAGGACACCGCCATGTACTACTGCAAGGC<br>CAGCTGCGTGAGGGGCAGGGCCATCAGCGAGTACTGGGGCCAGGGCACC<br>CAGGTGACCGTGAGCAGC<br>(SEQ ID NO: 102) |
| hIL27Ra VHH6 | CAGGTGCAGCTGCAGGAGAGCGGCGGCGGCCTGGTGCAGCCCGGCGGCA<br>GCCTGAGGCTGAGCTGCGCCGCCAGCGGCTTCAGCTTCAGCAGCTACGCC<br>ATGAAGTGGGTGAGGCAGGCCCCCGGCAAGGGCCTGGAGTGGGTGAGCA<br>CCATCAGCAGCGGCGGCAGCAGCACCAACTACGCCGACAGCGTGAAGGG<br>CAGGTTCACCATCAGCAGGGACAACGCCAAGAACACCCTGTACCTGCAG<br>CTGAACAGCCTGAAGATCGAGGACACCGCCATGTACTACTGCGCCAAGG<br>CCATCGTGCCCACCGGCGCCACCATGGAGAGGGGCCAGGGCACCCAGGT<br>GACCGTGAGCAGC<br>(SEQ ID NO: 103) |
| hIL27Ra VHH7 | CAGGTGCAGCTGCAGGAGAGCGGCGGCGGCCTGGTGCAGCCCGGCGGCA<br>GCCTGAGGCTGAGCTGCGCCGCCAGCGGCTTCACCTTCAGCAGCTACCCC<br>ATGAGCTGGGTGAGGCAGGCCCCCGGCAAGGGCCTGGAGTGGATCAGCA<br>CCATCAGCGCCGGCGGCGACACCACCCTGTACGCCGACAGCGTGAAGGG<br>CAGGTTCACCAGCAGCAGGGACAACGCCAAGAACACCCTGTACCTGCAG<br>CTGAACAGCCTGAAGACCGAGGACACCGCCATCTACTACTGCGCCAAGA<br>GGATCGACTGCAACAGCGGCTACTGCTACAGGAGGAACTACTGGGGCCA<br>GGGCACCCAGGTGACCGTGAGCAGC<br>(SEQ ID NO: 104) |
| hIL27Ra VHH8 | CAGGTGCAGCTGCAGGAGAGCGGCGGCGGCAGCGTGCAGGTGGGCGGC<br>AGCCTGAGGCTGAGCTGCGCCGCCAGCGGCTTCACCTTCAGCAGCTACCC<br>CATGAGCTGGGTGAGGCAGGCCCCCGGCAAGGGCCTGGAGTGGATCAGC<br>ACCATCAGCGCCGGCGGCGACACCACCCTGTACGCCGACAGCGTGAAGG<br>GCAGGTTCACCAGCAGCAGGGACAACGCCAAGAACACCCTGTACCTGCA<br>GCTGAACAGCCTGAAGACCGAGGACACCGCCATCTACTACTGCGCCAAG<br>AGGATCGACTGCAACAGCGGCTACTGCTACAGGAGGAACTACTGGGGCC<br>AGGGCACCCAGGTGACCGTGAGCAGC<br>(SEQ ID NO: 105) |
| hIL27Ra VHH9 | CAGGTGCAGCTGCAGGAGAGCGGCGGCGGCAGCGTGCAGAGCGGCGGC<br>AGCCTGAGGCTGAGCTGCGCCGCCAGCGGCTTCACCTACAGCACCAGCA<br>ACAGCTGGATGGCCTGGTTCAGGCAGGCCCCCGGCAAGGAGAGGGAGG<br>CGTGGCCGCCATCTACACCGTGGGCGGCAGCATCTTCTACGCCGACAGCG<br>TGAGGGGCAGGTTCACCATCAGCCAGGACGCCACCAAGAACATGTTCTA<br>CCTGCAGATGAACACCCTGAAGCCCGAGGACACCGCCATGTACTACTGC<br>GCCGCCGCCAGCGGCAGGCTGAGGGGCAAGTGGTTCTGGCCCTACGAGT<br>ACAACTACTGGGGCCAGGGCACCCAGGTGACCGTGAGCAGC<br>(SEQ ID NO: 106) |

TABLE 2-continued

DNA Sequences Encoding VHHs of Table 1.

| Name | Sequence |
|---|---|
| hIL27Ra VHH10 | CAGGTGCAGCTGCAGGAGAGCGGCGGCGGCAGCGTGCAGGCCGGCGGC<br>AGCCTGAGGCTGAGCTGCAGGGCCAGCGGCAGCACCTACAGCAACTACT<br>GCCTGGGCTGGTTCAGGCAGATCACCGGCAAGGAGAGGGAGGGCGTGGC<br>CGTGATCAACTGGGTGGGCGGCATGCTGTACTTCGCCGACAGCGTGAAG<br>GGCAGGTTCACCGTGAGCCAGGACCAGGCCAAGAACACCCTGTACCTGC<br>AGATGAACAGCCTGAAGCCCGAGGACACCGCCATGTACTACTGCGCCGC<br>CGAGAGCGTGAGCAGCTTCAGCTGCGGCGGCTGGCTGACCAGGCCCGAC<br>AGGGTGCCCTACTGGGGCCAGGGCACCCAGGTGACCGTGAGCAGC<br>(SEQ ID NO: 107) |
| hIL27Ra VHH11 | CAGGTGCAGCTGCAGGAGAGCGGCGGCGGCAGCGTGCAGGCCGGCGGC<br>AGCCTGAGGCTGAGCTGCAGGGCCAGCGGCAGCACCTACAGCAACTACT<br>GCCTGGGCTGGTTCAGGCAGAGCACCGGCAAGGAGAGGGAGGGCGTGG<br>CCGTGATCAACTGGGTGGGCGGCATGCTGTACTTCGCCGACAGCGTGAA<br>GGGCAGGTTCACCGTGAGCCAGGACCACGCCAAGAACACCGTGACCCTG<br>CAGATGAACAGCCTGAAGCCCGAGGACACCGCCATGTACTACTGCGCCG<br>CCGAGAGCGTGAGCAGCTTCAGCTGCGGCGGCTGGCTGACCAGGCCCGG<br>CAGGGTGCCCTACTGGGGCCAGGGCACCCAGGTGACCGTGAGCAGC<br>(SEQ ID NO: 108) |
| hIL27Ra VHH12 | CAGGTGCAGCTGCAGGAGAGCGGCGGCGGCAGCGTGCAGGCCGGCGAG<br>AGCCTGAGGCTGAGCTGCAGGGCCAGCGGCAGCACCTACAGCAACTACT<br>GCCTGGGCTGGTTCAGGCAGATCACCGGCAAGGAGAGGGAGGGCGTGGC<br>CGTGATCAACTGGGTGGGCGGCATGCTGTACTTCGCCGACAGCGTGAAG<br>GGCAGGTTCACCGTGAGCCAGGACCAGGCCAAGAACACCGTGTACCTGG<br>AGATGAACAGCCTGAAGCCCGAGGACACCGCCATGTACTACTGCGCCAC<br>CGAGAGCGTGAGCAGCTTCAGCTGCGGCGGCTGGCTGACCAGGCCCGAC<br>AGGGTGCCCTACTGGGGCCAGGGCACCCAGGTGACCGTGAGCAGC<br>(SEQ ID NO: 109) |
| hIL27Ra VHH13 | CAGGTGCAGCTGCAGGAGAGCGGCGGCGGCAGCGTGCAGGCCGGCGGC<br>AGCCTGAGGCTGAGCTGCGTGGCCAGCGGCTACGTGAGCTGCGACTACT<br>TCCTGCCCAGCTGGTACAGGCAGGCCCCCGGCAAGGAGAGGGAGTTCGT<br>GAGCATCATCGACGGCACCGGCAGCACCAGCTACGCCGCCAGCGTGAAG<br>GGCAGGTTCACCGCCAGCCAGGACAGGGGCAAGAACATCGCCTACCTGC<br>AGATGAACAGCCTGAAGCCCGAGGACACCGCCATGTACTACTGCAAGGC<br>CAGCTGCGTGAGGGGCAGGACCATCAGCGAGTACGGGGCCAGGGCACC<br>CAGGTGACCGTGAGCAGC<br>(SEQ ID NO: 110) |
| hIL27Ra VHH14 | CAGGTGCAGCTGCAGGAGAGCGGCGGCGGCAGCGTGCAGGCCGGCGGC<br>AGCCTGAGGCTGAGCTGCGTGGCCAGCGGCTACGTGAGCTGCGACTACT<br>TCCTGCCCAGCTGGTACAGGCAGGCCCCCGGCAAGGAGAGGGAGTTCGT<br>GAGCATCATCGACGGCACCGGCAGCACCAGCTACGCCGCCAGCGTGAAG<br>GGCAGGTTCACCGCCAGCCAGGACAAGGGCAAGAACATCGCCTACCTGC<br>AGATGAACAGCCTGAAGCCCGAGGACACCGCCATGTACTACTGCAAGGC<br>CAGCTGCGTGAGGGGCAGGGCCATCAGCGAGTACGGGGCCAGGGCACC<br>CAGGTGACCGTGAGCAGC<br>(SEQ ID NO: 111) |
| hIL27Ra VHH15 | CAGGTGCAGCTGCAGGAGAGCGGCGGCGGCAGCGTGCAGGCCGGCGGC<br>AGCCTGAGGCTGAGCTGCGTGGCCAGCGGCTACGTGAGCTGCGACTACT<br>TCCTGCCCAGCTGGTACAGGCAGGCCCCCGGCAAGGAGAGGGAGTTCGT<br>GAGCATCATCGACGGCACCGGCAGCACCAGCTACGCCGCCAGCGTGAAG<br>GGCAGGTTCACCGCCAGCCAGGACAAGGGCAAGAACATCGCCTACCTGC<br>AGATGAACACCCTGAAGCCCGAGGACACCGCCATGTACTACTGCAAGGC<br>CAGCTGCGTGAGGGGCAGGGCCATCAGCGAGTACGGGGCCAGGGCACC<br>CAGGTGACCGTGAGCAGC<br>(SEQ ID NO: 112) |
| hIL27Ra VHH16 | CAGGTGCAGCTGCAGGAGAGCGGCGGCGGCAGCGTGCAGGCCGGCGGC<br>AGCCTGAGGCTGAGCTGCAGGGCCAGCGGCAGCACCTACAGCAACTACT<br>GCCTGGGCTGGTTCAGGCAGATCACCGGCAAGGAGAGGGAGGGCGTGGC<br>CGTGATCAACTGGGTGGGCGGCATGCTGTACTTCGCCGACAGCGTGAAG<br>GGCAGGTTCACCGTGAGCCAGGACCAGGCCAAGAACACCGTGTACCTGC<br>AGATGAACAGCCTGAAGCCCGAGGACACCGCCATGTACTACTGCGCCGC<br>CGAGAGCGCCAGCAGCTTCAGCTGCGGCGGCTGGCTGACCAGGCCCGAC<br>AGGGTGCCCTACTGGGGCCAGGGCACCCAGGTGACCGTGAGCAGC<br>(SEQ ID NO: 113) |
| hIL27Ra VHH17 | CAGGTGCAGCTGCAGGAGAGCGGCGGCGGCCTGGTGCAGCCCGGCGGCA<br>GCCTGAGGCTGAGCTGCGCCGCCAGCGGCTTCACCTTCAGCCTGAGCGGC<br>ATGAGCTGGGTGAGGCAGGCCCCCGGCAAGGGCCTGGAGTGGGTGAGCG<br>CCATCAGCAGCGGCGGCGCCAGCACCTACTACACCGACAGCGTGAAGGG<br>CAGGTTCACCATCAGCAGGGACAACGCCAAGAACATGCTGTACCTGCAG |

TABLE 2-continued

DNA Sequences Encoding VHHs of Table 1.

| Name | Sequence |
|---|---|
| | CTGAACAGCCTGAAGACCGAGGACACCGCCATGTACTACTGCGCCAAGG<br>GCGGCAGCGGCTACGGCGACGCCAGCAGGATGACCAGCCCCGGCAGCCA<br>GGGCACCCAGGTGACCGTGAGCAGC<br>(SEQ ID NO: 114) |
| hIL27Ra VHH18 | CAGGTGCAGCTGCAGGAGAGCGGCGGCGGCAGCGTGCAGGCCGGCGGC<br>AGCCTGAGGCTGAGCTGCGTGGCCAGCGGCTACGTGAGCTGCGACTACT<br>TCCTGCCCAGCTGGTACAGGCAGGCCCCCGGCAAGGAGAGGGAGTTCGT<br>GAGCATCATCGACGGCACCGGCCAGCACCAGCTACGCCCGCCAGCGTGAAG<br>GGCAGGTTCACCGCCAGCCAGGACAAGGGCAAGAACATCGCCTACCTGC<br>AGATGAACAGCCTGAAGCCCGAGGACACCGCCATGTACTACTGCAAGGC<br>CAGCTGCGTGAGGGGCAGGGGCATCAGCGAGTACTGGGGCCAGGGCACC<br>CAGGTGACCGTGAGCAGC<br>(SEQ ID NO: 115) |
| hIL27Ra VHH19 | CAGGTGCAGCTGCAGGAGAGCGGCGGCGGCAGCGTGCAGGCCGGCGGC<br>AGCCTGAGGCTGAGCTGCAGGGCCAGCGGCAGCACCTACAGCAACTACT<br>GCCTGGGCTGGTTCAGGCAGATCACCGGCAAGGAGAGGGAGGGCGTGGC<br>CGTGATCAACTGGGTGGGCGGCATGCTGTACTTCGCCGACAGCGTGAAG<br>GGCAGGTTCACCGTGAGCCAGGACCAGGCCAAGAACACCGTGTACCTGC<br>AGATGAACAGCCTGAAGCCCGAGGACACCGCCATGTACTACTGCGCCGC<br>CGAGAGCGTGAGCAGCTTCAGCTGCGGCGGCTGGCTGACCAGGCCCGAC<br>AGGGTGCCCTACTGGGGCCAGGGCACCCAGGTGACCGTGAGCAGC<br>(SEQ ID NO: 116) |
| hIL27Ra VHH20 | CAGGTGCAGCTGCAGGAGAGCGGCGGCGGCCTGGTGCAGCCCGGCGGCA<br>GCCTGAGGCTGAGCTGCGCCGCCAGCGGCTTCACCTTCAGCAGCTACCC<br>ATGAGCTGGGTGAGGCAGGCCCCCGGCAAGGGCCTGGAGTGGGTGAGCA<br>CCATCAGCAGCGGCGGCGACACCACCCTGTACGCCGACAGCGTGAAGGG<br>CAGGTTCACCAGCAGCAGGGACAACGCCAAGAACACCCTGTACCTGCAG<br>CTGAACAGCCTGAAGACCGAGGACACCGCCATGTACTACTGCGCCAAGA<br>GGATCGACTGCAACAGCGGCTACTGCTACAAGAGGAGCTACTGGGGCCA<br>GGGCACCCAGGTGACCGTGAGCAGC<br>(SEQ ID NO: 117) |
| hIL27Ra VHH21 | CAGGTGCAGCTGCAGGAGAGCGGCGGCGGCCTGGTGCAGCCCGGCGGCA<br>GCCTGAGGCTGAGCTGCGCCGCCAGCGGCTTCACCTTCAGCCTGAGCAGC<br>ATGAGCTGGGTGAGGCAGGCCCCCGGCAAGGGCCTGGAGTGGGTGAGCG<br>CCATCAGCAGCGGCGGCGCCAGCACCTACTACACCGACAGCGTGAAGGG<br>CAGGTTCACCATCAGCAGGGACAACGCCAAGAACATGCTGTACCTGCAG<br>CTGAACAGCCTGAAGACCGAGGACACCGCCATGTACTACTGCGCCAAGG<br>GCGGCAGCGGCTACGGCGACGCCAGCAGGATGACCAGCCCCGGCAGCCA<br>GGGCACCCAGGTGACCGTGAGCAGC<br>(SEQ ID NO: 118) |
| hIL27Ra VHH22 | CAGGTGCAGCTGCAGGAGAGCGGCGGCGGCAGCGTGCAGGCCGGCGGC<br>AGCCTGAGGCTGAGCTGCAGGGCCAGCGGCAGCACCTACAGCAACTACT<br>GCCTGGGCTGGTTCAGGCAGACCACCGGCAAGGAGAGGGAGGGCGTGGC<br>CGTGATCAACTGGGTGGGCGGCATGCTGTACTTCGCCGACAGCGTGAAG<br>GGCAGGTTCACCGTGAGCCAGGACCAGGCCAAGAACACCGTGTACCTGC<br>AGATGAACAGCCTGAAGCCCGAGGACACCGCCATGTACTACTGCGCCGC<br>CGAGAGCGTGAGCAGCTTCAGCTGCGGCGGCTGGCTGACCAGGCCCGAC<br>AGGGTGCCCTACTGGGGCCAGGGCACCCAGGTGACCGTGAGCAGC<br>(SEQ ID NO: 119) |
| hIL27Ra VHH23 | CAGGTGCAGCTGCAGGAGAGCGGCGGCGGCAGCGTGCAGGCCGGCGGC<br>AGCCTGAGGCTGAGCTGCAGGGCCAGCAGGAGCCCCTACGGCAACTACT<br>GCCTGGGCTGGTTCAGGCAGAGCACCGGCAAGGAGAGGGAGGGCGTGG<br>CCGTGATCAACTGGGTGGGCGGCATGCTGTACTTCGCCGACAGCGTGAA<br>GGGCAGGTTCACCGTGAGCCAGGACCACGCCAAGAACACCGTGACCCTG<br>CAGATGAACAGCCTGAAGCCCGAGGACACCGCCATGTACTACTGCGCCG<br>CCGAGAGCGTGAGCAGCTTCAGCTGCGGCGGCTGGCTGACCAGGCCCGA<br>CAGGGTGCCCTACTGGGGCCAGGGCACCCAGGTGACCGTGAGCAGC<br>(SEQ ID NO: 120) |
| hIL27Ra VHH24 | CAGGTGCAGCTGCAGGAGAGCGGCGGCGGCCTGGTGCAGCCCGGCGGCA<br>GCCTGAGGCTGAGCTGCGCCGCCAGCGGCTTCACCTTCAGCCACAGCGG<br>CATGAGCTGGGTGAGGCAGGCCCCCGGCAAGGGCCTGGAGTGGGTGAGC<br>ACCATCAACAGCGGCGGCGCCAGCACCTACTACACCGACAGCGTGAAGG<br>GCAGGTTCACCATCAGCAGGGACAACGCCAAGAACATGCTGTACCTGCA<br>GCTGAACAGCCTGAAGACCGAGGACACCGCCATGTACTACTGCGCCAAG<br>GGCGGCAGCGGCTACGGCGACGCCAGCAGGATGACCAGCCCCGGCAGCC<br>AGGGCACCCAGGTGACCGTGAGCAGC<br>(SEQ ID NO: 121) |

In some embodiments, the IL27Ra is the murine IL27Ra.

In some embodiments, a IL27Ra binding molecule comprises a single domain antibody (sdAb) that specifically binds to the extracellular domain of the mouse or murine IL27Ra (mIL27Ra).

In some embodiments, a IL27Ra binding molecule is a sdAb, the sdAb comprising a set of CDRs corresponding to CDR1, CDR2, and CDR3 as shown in a row of Table 3 below.

In some embodiments, the IL27Ra binding molecule comprises a CDR1, a CDR2, and a CDR3 as described in a row of Table 3 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 3 below.

In some embodiments, the IL27Ra binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS: 122, 126, 130, 134, 138, 142, 146, 150, 154, 158, 162, 166, 170 and 174 as shown in Table 3 below.

TABLE 3 mIL2Rq VHHs and CDRs Amino Acid (AA) Sequences

| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| mIL27Ra VHH1 | QVQLQESGGGSVQA GGSLRLSCAASKNSN FMGWFRQAPGKERE GVAAMMTKNNNTY YADSVKGRFTISHDN AKNTVYLQMDSLKP EDTAVYYCAAVYRT RRLRVLEAANFDYW GQGTQVTVSS | 122 | NSNFM G | 123 | AMMTK NNNTY YADSV KG | 124 | VYRTR RLRVLE AANFD Y | 125 |
| mIL27Ra VHH2 | QVQLQESGGGSVQA GGSLRLSCTASGYTS SRYCMGWFRQTPGK KREGVAAIYTGGTT FYHGSVKGRFTISQD NTTNTVYLQMHNLK PEDTAMYYCAAGPV TRACDEYNYWGQGT QVTVSS | 126 | YTSSR YCMG | 127 | AIYTGG GTTFY HGSVK G | 128 | GPVTR ACDEY NY | 129 |
| mIL27Ra VHH3 | QVQLQESGGGSVQA GGSLRLSCAGSGYSL SNYCMGWFRQAPGQ GREGVASLRFVSGAT FYADSVKGRFTIAQD NAKNTLYLQMNSLK PEDTAMYYCGIKSRG ICGGRLVDVDFGNW GQGTQVTVSS | 130 | YSLSN YCMG | 131 | SLRFVS GATFY ADSVK G | 132 | KSRGIC GGRLV DVDFG N | 133 |
| mIL27Ra VHH4 | QVQLQESGGGSVQA GGSLRLSCAASGYSI NRMGWFRQAPGKER EGVAAISIGGGQTYY ADSVKGRFTISQDNA KNTVDLQMNSLKPE DTAMYYCAAGLVYG EAWLDSRHYNKWG QGTQVTVSS | 134 | YSINR MG | 135 | AISIGG GQTYY ADSVK G | 136 | GLVYG EAWLD SRHYN K | 137 |
| mIL27Ra VHH5 | QVQLQESGGGSVQA GGSLRLSCAVSGDST YSMGWFRQPPGKER EGVAAIAKDGITIHA DSVKGRFTISKDNAK NTLYLQMNSLKPEDT AMYYCAAHRPYGPP LNPRWYTYWGQGTQ VTVSS | 138 | DSTYS MG | 139 | AIAKD GITIHA DSVKG | 140 | HRPYG PPLNPR WYTY | 141 |
| mIL27Ra VHH6 | QVQLQESGGGSVQA GGSLRLSCAASGYTY SSYCMAWFRQAPGK EREGVAAIDSDGSTS YADSVKGRFTISKDN AKNTLYLQMNSLKP | 142 | YTYSS YCMA | 143 | AIDSDG STSYAD SVKG | 144 | ASGRC LGPGIR SLI | 145 |

TABLE 3-continued mIL2Rq VHHs and CDRs Amino Acid (AA) Sequences

| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| | EDTAMYYCAAASGR CLGPGIRSLIWGQGT QVTVSS | | | | | | | |
| mIL27Ra VHH7 | QVQLQESGGGSVQA GGSLRLSCAVSGDST YSMGWFRQPPGKER EGVAAITKDITIHADS VKGRFTISKDNAKNT LYLQMNSLKPEDTA MYYCAAHRPYGPPL NPRWYTYWGQGTQ VTVSS | 146 | DSTYS MG | 147 | AITKDI TIHADS VKG | 148 | HRPYG PPLNPR WYTY | 149 |
| mIL27Ra VHH8 | QVQLQESGGGSVQA GGSLRLSCAVSGDST YSMGWFRQPPGKER EGVAAIPTDGITIHAD SVKGRFTISKDNAKN TLYLQMNSLKPEDTA MYYCAAHRPYGPPL NPRWYTYWGQGTQ VTVSS | 150 | DSTYS MG | 151 | AIPTDG ITIHAD SVKG | 152 | HRPYG PPLNPR WYTY | 153 |
| mIL27Ra VHH9 | QVQLQESGGGSVQA GGSLRLSCAVSGDST YSMGWFRQPPGKER EGVAAIAKDGITIHA DSVKGRFTISKDNAK NTLYLQMSSLKPEDT AMYYCAAHRPYGPP LNPRWYTYWGQGTQ VTVSS | 154 | DSTYS MG | 155 | AIAKD GITIHA DSVKG | 156 | HRPYG PPLNPR WYTY | 157 |
| mIL27Ra VHH10 | QVQLQESGGGSVQA GGSLRLSCAVSGDST YSMGWFRQPPGKER EGVAAIGKDGITIHA DSVKGRFTISKDNAK NTLYLQMNSLKPEDT AMYYCAAHRPYGPP LNPRWYTYWGQGTQ VTVSS | 158 | DSTYS MG | 159 | AIGKD GITIHA DSVKG | 160 | HRPYG PPLNPR WYTY | 161 |
| mIL27Ra VHH11 | QVQLQESGGGSVQA GGSLRLSCAVSGDST YSMGWFRQPPGKER EGVAAITKDITIHADS VKGRFTISKDNAKNT LYLQMNSLRPEDTA MYYCAAHRPYGPPL NPRWYTYWGQGTQ VTVSS | 162 | DSTYS MG | 163 | AITKDI TIHADS VKG | 164 | HRPYG PPLNPR WYTY | 165 |
| mIL27Ra VHH12 | QVQLQESGGGSVQT GGSLRLSCAASGYSI NRMAWFRQAPGKER EGVAAISIGGDRTYY ADSVKGRFTISQDNA KHTVDLQMNSLKPE DTAMYYCAAGLVYG EAWLDSRHYNKWG QGTQVTVSS | 166 | YSINR MA | 167 | AISIGG DRTYY ADSVK G | 168 | GLVYG EAWLD SRHYN K | 169 |
| mIL27Ra VHH13 | QVQLQESGGGSVQA GGSLRLSCAASGYSI NRMGWFRQAPGKER EGVAAISIGGGRTYY ADSVKGRFTISQDNA KNTVDLQMNSLKPE DTAMYYCAAGLVYG EAWLDSRHYNKWG QGTQVTVSS | 170 | YSINR MG | 171 | AISIGG GRTYY ADSVK G | 172 | GLVYG EAWLD SRHYN K | 173 |

TABLE 3-continued mIL2Rq VHHs and CDRs Amino Acid (AA) Sequences

| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| mIL27Ra VHH14 | QVQLQESGGGSVQA GGSLRLSCAVSGDST YSMGWFRQPPGKER EGVAAITKDGITIHAD SVKGRFTISGDNAKN TLYLQMNNLKPEDT AMYYCAAHRPYGPP LNPRWYTYWGQGTQ VTVSS | 174 | DSTYS M | 175 | AITKDG ITIHAD SVKG | 176 | HRPYG PPLNPR WYTY | 177 |

In some embodiments, the foregoing sets of CDRs are incorporated in a humanized VHH framework to provide "humanized" sdAb IL27Rα binding molecules.

The disclosure further provides methods of chemical or recombinant processes for the preparation of the IL27Rα binding molecules of the present disclosure.

The disclosure further provides nucleic acids encoding the IL27Ra binding molecules. Table 4 below provide examples of DNA sequences encoding hIL27Ra binding molecules as described in Table 3 above.

TABLE 4

DNA Sequences Encoding VHHs of Table 3.

| Name | DNA Sequence | SEQ ID NO. |
|---|---|---|
| mIL27Ra VHH1 | CAGGTGCAGCTGCAGGAGAGCGGCGGCGGCAGCGTGCAGGCCG GCGGCAGCCTGAGGCTGAGCTGCGCCGCCAGCAAGAACAGCAA CTTCATGGGCTGGTTCAGGCAGGCCCCCGGCAAGGAGAGGGAGG GCGTGGCCGCCATGATGACCAAGAACAACAACACCTACTACGCC GACAGCGTGAAGGGCAGGTTCACCATCAGCCACGACAACGCCA AGAACACCGTGTACCTGCAGATGGACAGCCTGAAGCCCGAGGAC ACCGCCGTGTACTACTGCGCCGCCGTGTACAGGACCAGGAGGCT GAGGGTGCTGGAGGCCGCCAACTTCGACTACTGGGGCCAGGGCA CCCAGGTGACCGTGAGCAGC | 178 |
| mIL27Ra VHH2 | CAGGTGCAGCTGCAGGAGAGCGGCGGCGGCAGCGTGCAGGCCG GCGGCAGCCTGAGGCTGAGCTGCACCGCCAGCGGCTACACCAGC AGCAGGTACTGCATGGGCTGGTTCAGGCAGACCCCCGGCAAGAA GAGGGAGGGCGTGGCCGCCATCTACACCGGCGGCGGCACCACCT TCTACCACGGCAGCGTGAAGGGCAGGTTCACCATCAGCCAGGAC AACACCACCAACACCGTGTACCTGCAGATGCACAACCTGAAGCC CGAGGACACCGCCATGTACTACTGCGCCGCCGGCCCCGTGACCA GGGCCTGCGACGAGTACAACTACTGGGGCCAGGGCACCCAGGTG ACCGTGAGCAGC | 179 |
| mIL27Ra VHH3 | CAGGTGCAGCTGCAGGAGAGCGGCGGCGGCAGCGTGCAGGCCG GCGGCAGCCTGAGGCTGAGCTGCGCCGGCAGCGGCTACAGCCTG AGCAACTACTGCATGGGCTGGTTCAGGCAGGCCCCCGGCCAGGG CAGGGAGGGCGTGGCCAGCCTGAGGTTCGTGAGCGGCGCCACCT TCTACGCCGACAGCGTGAAGGGCAGGTTCACCATCGCCCAGGAC AACGCCAAGAACACCCTGTACCTGCAGATGAACAGCCTGAAGCC CGAGGACACCGCCATGTACTACTGCGGCATCAAGAGCAGGGGCA TCTGCGGCGGCAGGCTGGTGGACGTGGACTTCGGCAACTGGGGC CAGGGCACCCAGGTGACCGTGAGCAGC | 180 |
| mIL27Ra VHH4 | CAGGTGCAGCTGCAGGAGAGCGGCGGCGGCAGCGTGCAGGCCG GCGGCAGCCTGAGGCTGAGCTGCGCCGCCAGCGGCTACAGCATC AACAGGATGGGCTGGTTCAGGCAGGCCCCCGGCAAGGAGAGGG AGGGCGTGGCCGCCATCAGCATCGGCGGCGGCCAGACCTACTAC GCCGACAGCGTGAAGGGCAGGTTCACCATCAGCCAGGACAACG CCAAGAACACCGTGGACCTGCAGATGAACAGCCTGAAGCCCGA GGACACCGCCATGTACTACTGCGCCGCCGGCCTGGTGTACGGCG AGGCCTGGCTGGACAGCAGGCACTACAACAAGTGGGGCCAGGG CACCCAGGTGACCGTGAGCAGC | 181 |

TABLE 4-continued

DNA Sequences Encoding VHHs of Table 3.

| Name | DNA Sequence | SEQ ID NO. |
|---|---|---|
| mIL27Ra VHH5 | CAGGTGCAGCTGCAGGAGAGCGGCGGCGGCAGCGTGCAGGCCG GCGGCAGCCTGAGGCTGAGCTGCGCCGTGAGCGGCGACAGCACC TACAGCATGGGCTGGTTCAGGCAGCCCCCCGGCAAGGAGAGGG AGGGCGTGGCCGCCATCGCCAAGGACGGCATCACCATCCACGCC GACAGCGTGAAGGGCAGGTTCACCATCAGCAAGGACAACGCCA AGAACACCCTGTACCTGCAGATGAACAGCCTGAAGCCCGAGGAC ACCGCCATGTACTACTGCGCCGCCCACAGGCCCTACGGCCCCCC CCTGAACCCCAGGTGGTACACCTACTGGGGCCAGGGCACCCAGG TGACCGTGAGCAGC | 182 |
| mIL27Ra VHH6 | CAGGTGCAGCTGCAGGAGAGCGGCGGCGGCAGCGTGCAGGCCG GCGGCAGCCTGAGGCTGAGCTGCGCCGCCAGCGGCTACACCTAC AGCAGCTACTGCATGGGCTGGTTCAGGCAGGCCCCCGGCAAGGA GAGGGAGGGCGTGGCCGCCATCGACAGCGACGGCAGCACCAGC TACGCCGACAGCGTGAAGGGCAGGTTCACCATCAGCAAGGACA ACGCCAAGAACACCCTGTACCTGCAGATGAACAGCCTGAAGCCC GAGGACACCGCCATGTACTACTGCGCCGCCGCCAGCGGCAGGTG CCTGGGCCCCGGCATCAGGAGCCTGATCTGGGGCCAGGGCACCC AGGTGACCGTGAGCAGC | 183 |
| mIL27Ra VHH7 | CAGGTGCAGCTGCAGGAGAGCGGCGGCGGCAGCGTGCAGGCCG GCGGCAGCCTGAGGCTGAGCTGCGCCGTGAGCGGCGACAGCACC TACAGCATGGGCTGGTTCAGGCAGCCCCCCGGCAAGGAGAGGG AGGGCGTGGCCGCCATCACCAAGGACATCACCATCCACGCCGAC AGCGTGAAGGGCAGGTTCACCATCAGCAAGGACAACGCCAAGA ACACCCTGTACCTGCAGATGAACAGCCTGAAGCCCGAGGACACC GCCATGTACTACTGCGCCGCCCACAGGCCCTACGGCCCCCCCCT GAACCCCAGGTGGTACACCTACTGGGGCCAGGGCACCCAGGTGA CCGTGAGCAGC | 184 |
| mIL27Ra VHH8 | CAGGTGCAGCTGCAGGAGAGCGGCGGCGGCAGCGTGCAGGCCG GCGGCAGCCTGAGGCTGAGCTGCGCCGTGAGCGGCGACAGCACC TACAGCATGGGCTGGTTCAGGCAGCCCCCCGGCAAGGAGAGGG AGGGCGTGGCCGCCATCCCCACCGACGGCATCACCATCCACGCC GACAGCGTGAAGGGCAGGTTCACCATCAGCAAGGACAACGCCA AGAACACCCTGTACCTGCAGATGAACAGCCTGAAGCCCGAGGAC ACCGCCATGTACTACTGCGCCGCCCACAGGCCCTACGGCCCCCC CCTGAACCCCAGGTGGTACACCTACTGGGGCCAGGGCACCCAGG TGACCGTGAGCAGC | 185 |
| mIL27Ra VHH9 | CAGGTGCAGCTGCAGGAGAGCGGCGGCGGCAGCGTGCAGGCCG GCGGCAGCCTGAGGCTGAGCTGCGCCGTGAGCGGCGACAGCACC TACAGCATGGGCTGGTTCAGGCAGCCCCCCGGCAAGGAGAGGG AGGGCGTGGCCGCCATCGCCAAGGACGGCATCACCATCCACGCC GACAGCGTGAAGGGCAGGTTCACCATCAGCAAGGACAACGCCA AGAACACCCTGTACCTGCAGATGAGCAGCCTGAAGCCCGAGGAC ACCGCCATGTACTACTGCGCCGCCCACAGGCCCTACGGCCCCCC CCTGAACCCCAGGTGGTACACCTACTGGGGCCAGGGCACCCAGG TGACCGTGAGCAGC | 186 |
| mIL27Ra VHH10 | CAGGTGCAGCTGCAGGAGAGCGGCGGCGGCAGCGTGCAGGCCG GCGGCAGCCTGAGGCTGAGCTGCGCCGTGAGCGGCGACAGCACC TACAGCATGGGCTGGTTCAGGCAGCCCCCCGGCAAGGAGAGGG AGGGCGTGGCCGCCATCGGCAAGGACGGCATCACCATCCACGCC GACAGCGTGAAGGGCAGGTTCACCATCAGCAAGGACAACGCCA AGAACACCCTGTACCTGCAGATGAACAGCCTGAAGCCCGAGGAC ACCGCCATGTACTACTGCGCCGCCCACAGGCCCTACGGCCCCCC CCTGAACCCCAGGTGGTACACCTACTGGGGCCAGGGCACCCAGG TGACCGTGAGCAGC | 187 |
| mIL27Ra VHH11 | CAGGTGCAGCTGCAGGAGAGCGGCGGCGGCAGCGTGCAGGCCG GCGGCAGCCTGAGGCTGAGCTGCGCCGTGAGCGGCGACAGCACC TACAGCATGGGCTGGTTCAGGCAGCCCCCCGGCAAGGAGAGGG AGGGCGTGGCCGCCATCACCAAGGACATCACCATCCACGCCGAC AGCGTGAAGGGCAGGTTCACCATCAGCAAGGACAACGCCAAGA ACACCCTGTACCTGCAGATGAACAGCCTGAGGCCCGAGGACACC GCCATGTACTACTGCGCCGCCCACAGGCCCTACGGCCCCCCCCT GAACCCCAGGTGGTACACCTACTGGGGCCAGGGCACCCAGGTGA CCGTGAGCAGC | 188 |
| mIL27Ra VHH12 | CAGGTGCAGCTGCAGGAGAGCGGCGGCGGCAGCGTGCAGACCG GCGGCAGCCTGAGGCTGAGCTGCGCCGCCAGCGGCTACAGCATC AACAGGATGGGCCTGTTCAGGCAGGCCCCCGGCAAGGAGAGGG AGGGCGTGGCCGCCATCAGCATCGGCGGCGACAGGACCTACTAC | 189 |

TABLE 4-continued

DNA Sequences Encoding VHHs of Table 3.

| Name | DNA Sequence | SEQ ID NO. |
|---|---|---|
| | GCCGACAGCGTGAAGGGCAGGTTCACCATCAGCCAGGACAACG<br>CCAAGCACACCGTGGACCTGCAGATGAACAGCCTGAAGCCCGAG<br>GACACCGCCATGTACTACTGCGCCGCCGGCCTGGTGTACGGCGA<br>GGCCTGGCTGGACAGCAGGCACTACAACAAGTGGGGCCAGGGC<br>ACCCAGGTGACCGTGAGCAGC | |
| mIL27Ra VHH13 | CAGGTGCAGCTGCAGGAGAGCGGCGGCGGCAGCGTGCAGGCCG<br>GCGGCAGCCTGAGGCTGAGCTGCGCCGCCAGCGGCTACAGCATC<br>AACAGGATGGGCTGGTTCAGGCAGGCCCCCGGCAAGGAGAGGG<br>AGGGCGTGGCCGCCATCAGCATCGGCGGCGGCAGGACCTACTAC<br>GCCGACAGCGTGAAGGGCAGGTTCACCATCAGCCAGGACAACG<br>CCAAGAACACCGTGGACCTGCAGATGAACAGCCTGAAGCCCGA<br>GGACACCGCCATGTACTACTGCGCCGCCGGCCTGGTGTACGGCG<br>AGGCCTGGCTGGACAGCAGGCACTACAACAAGTGGGGCCAGGG<br>CACCCAGGTGACCGTGAGCAGC | 190 |
| mIL27Ra VHH14 | CAGGTGCAGCTGCAGGAGAGCGGCGGCGGCAGCGTGCAGGCCG<br>GCGGCAGCCTGAGGCTGAGCTGCGCCGTGAGCGGCGACAGCACC<br>TACAGCATGGGCTGGTTCAGGCAGCCCCCGGCAAGGAGAGGG<br>AGGGCGTGGCCGCCATCACCAAGGACGGCATCACCATCCACGCC<br>GACAGCGTGAAGGGCAGGTTCACCATCAGCGGCGACAACGCCA<br>AGAACACCCTGTACCTGCAGATGAACAACCTGAAGCCCGAGGAC<br>ACCGCCATGTACTACTGCGCCGCCCACAGGCCCTACGGCCCCCC<br>CCTGAACCCCAGGTGGTACACCTACTGGGGCCAGGGCACCCAGG<br>TGACCGTGAGCAGC | 191 |

The disclosure further provides recombinant viral and non-viral vectors comprising a nucleic acid encoding the IL27Rα binding molecules of the present disclosure or the CDRs of the IL27Rα binding molecules of the present disclosure.

The disclosure further provides host cells comprising recombinant viral and non-viral vectors comprising a nucleic acid the IL27Rα binding molecules of the present disclosure or the CDRs of the IL27Rα binding molecules of the present disclosure.

The disclosure further provides host cells comprising recombinant viral and non-viral vectors comprising a nucleic acid the IL27Rα binding molecules of the present disclosure or the CDRs of the IL27Rα binding molecules of the present disclosure.

The disclosure further kits comprising the IL27Rα binding molecules of the present disclosure.

In another aspect, the present disclosure provides constructs for the identification of cells expressing the IL27Rα wherein the IL27Rα binding molecule is conjugated to one or more imaging agents, optionally through a chemical or polypeptide linker. The disclosure further provides methods of use of the foregoing in the identification of cells expressing the IL27Rα in a subject, the method comprising the administration of an effective amount of the IL27Rα binding molecule conjugated to the imaging agent to a subject in need to treatment and evaluating the subject for the presence of the imaging agent that is conjugated to the IL27Rα binding molecule.

In another aspect, the present disclosure provides IL27Rα binding molecules which have been modified for extended duration of action in vivo wherein the IL27Rα binding molecule is conjugated to one or more carrier molecules.

The present disclosure provides IL27Rα binding molecules comprising a polypeptide sequence that specifically binds to the extracellular domain of the IL27Rα and methods of use thereof in the isolation, depletion or enrichment of cells expressing IL27Rα in a biological sample.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader's convenience, the single and three letter amino acid codes are provided in Table 5 below:

TABLE 5

Amino Acid Abbreviations

| Single Letter Abbreviation | Name | 3-letter abbreviation |
| --- | --- | --- |
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g., an an IL27Rα binding molecule or an engineered cell expressing an IL27Rα binding molecule, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant $K_D$, a ratio of the dissociation rate constant between the molecule and the its target ($k_{off}$) and the association rate constant between the molecule and its target ($k_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind specifically to an antigen and compete for binding with the parent antibody, from which it is derived. The term "single domain antibody" includes scFv and VHH molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IL27Rα cell: The terms "IL27Rα cell", "IL27Rα-expressing cell", "IL27Rα-positive cell" and "IL27Rα+" cell are used interchangeably herein to refer to a cell which expresses and displays the IL27Rα antigen on the extracellular surface of the cell membrane. Similarly, the terms "IL27Rα-negative cell", "IL27Rα– cells" as are used interchangeably herein to describe cells which do not express or display IL27Rα antigen on the cell surface.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chem.* 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. In the context of the present disclosure, unless otherwise specified, the numbering of the CDR positions is provided according to the Kabat or a hybrid of Kabat and Chothia numbering convention.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) *J. Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS (USA) 89:10915-10919).

In An Amount Sufficient Amount to Effect a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) Ann. NY Acad Sci. 190:382-93; Kabat, et al., (1991) Sequences of Proteins of Immunological Interest, Fifth Edition, U.S. Department of Health and Human Services, NIH Publication No. 91-3242). The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs 2 and 3 in the variable region of an antibody follows Kabat numbering or simply, "Kabat." The positioning of CDR1 in the variable region of an antibody follows a hybrid of Kabat and Chothia numbering schemes.

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of viable cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant between antibody and the antigen is greater than about $10^6$ M, alternatively greater than about $10^8$ M, alternatively greater than about $10^{10}$ M, alternatively greater than about $10^{11}$ M, greater than about $10^{12}$ M as determined by, e.g., Scatchard analysis (Munsen, et al. (1980) Analyt. Biochem. 107:220-239). In one embodiment where the ligand is an IL27Rα binding sdAb and the receptor comprises an IL27Rα, the IL27Rα binding sdAb specifically binds if the equilibrium dissociation constant of the IL27Rα binding sdAb/IL27Rα ECD is greater than about $10^5$M, alternatively greater than about $10^6$ M, alternatively greater than about $10^7$M, alternatively greater than about $10^8$M, alternatively greater than about $10^9$M, alternatively greater than about $10^{10}$ M, or alternatively greater than about $10^{11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8K, Biacore 8K+, Biacore S200, Biacore T200 (Cytiva, 100 Results Way, Marlborough MA 01752). In some embodiments, the present disclosure provides molecules (e.g., IL27Rα binding sdAbs) that specifically bind to the IL27Rα isoform. As used herein, the binding affinity of an IL27Rα binding molecule for the IL27Rα, the binding affinity may be determined and/or quantified by surface plasmon resonance ("SPR"). In evaluating binding affinity of an IL27Rα binding molecule for the IL27Rα, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CMS chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 195) or 8×His (SEQ ID NO: 196)) for retention on a chip conjugated with NTA. In some embodiments, the IL27Rα binding molecule may be immobilized on the chip and IL27Rα (or ECD fragment thereof) be provided in the mobile phase. Alternatively, the IL27Rα (or ECD fragment thereof) may be immobilized on the chip and the IL27Rα binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of IL27Rα binding molecule for IL27Rα using SPR, the IL2Rb binding molecule may be derivatized by the C-terminal addition of a poly-His sequence (e.g., 6×His (SEQ ID NO: 195) or 8×His (SEQ ID NO: 196)) and immobilized on the NTA derivatized sensor chip and the IL27Rα receptor subunit for which the ligand's binding affinity is being evaluated is provided in the mobile phase. The means for incorporation of a poly-His sequence into the C-terminus of the IL27Rα binding molecule produced by recombinant DNA technology is well known to those of skill in the relevant art of biotechnology. In some embodiments, the binding affinity of IL27Rα binding molecule for a IL27Rα using SPR substantial accordance with the teaching of the Examples.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve $CD8^+$ T cells, cytotoxic $CD8^+$ T cells, naïve $CD4^+$ T cells, helper T cells, e.g., $T_H1$, $T_H2$, $T_H9$, $T_H11$, $T_H22$, $T_{FH}$; regulatory T cells, e.g., $T_R1$, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL27Rα isoform referred to interchangeably as IL27Rα cell, IL27Rα+ cell, IL27Rα T cell, or IL27Rα+ T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Transmembrane Domain: The term "transmembrane domain" or "TM" refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as contacting the subject with pharmaceutical composition comprising an IL27Rα binding sdAb alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell", "Treg cell", or "Treg" are interchangeably herein to refers to a type of CD4+ T cell that can suppress the responses of other T cells including but not limited to effector T cells (Teff). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term "conventional CD4+ T cells" is used to distinguish non-Treg CD4+ T cells from CD4+ Tregs.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IL27Rα

The IL27Rα binding molecules of the present disclosure specifically bind to the extracellular domain of the IL27Rα.

Human IL27Rα

In one embodiment, specifically bind to the extracellular domain of the human IL27Rα receptor subunit (hIL27Rα). hIL27Rα is expressed as a 636 amino acid precursor comprising a 32 amino acid N-terminal signal sequence which is post-translationally cleaved to provide an 604 amino acid mature protein. The canonical full-length acid hIL27Rα precursor (including the signal peptide) is a 636 amino acid polypeptide having the amino acid sequence:

(SEQ ID NO: 1)
MRGGRGAPFWLWPLPKLALLPLLWVLFQRTRPQGSAGPLQCYGVGPLGD

LNCSWEPLGDLGAPSELHLQSQKYRSNKTQTVAVAAGRSWVAIPREQLT

-continued
MSDKLLVWGTKAGQPLWPPVFVNLETQMKPNAPRLGPDVDFSEDDPLEA

TVHWAPPTWPSHKVLICQFHYRRCQEAAWTLLEPELKTIPLTPVEIQDL

ELATGYKVYGRCRMEKEEDLWGEWSPILSFQTPPSAPKDVWVSGNLCGT

PGGEEPLLLWKAPGPCVQVSYKVWFWVGGRELSPEGITCCCSLIPSGAE

WARVSAVNATSWEPLTNLSLVCLDSASAPRSVAVSSIAGSTELLVTWQP

GPGEPLEHVVDWARDGDPLEKLNWVRLPPGNLSALLPGNFTVGVPYRIT

VTAVSASGLASASSVWGFREELAPLVGPTLWRLQDAPPGTPAIAWGEVP

RHQLRGHLTHYTLCAQSGTSPSVCMNVSGNTQSVTLPDLPWGPCELWVT

ASTIAGQGPPGPILRLHLPDNTLRWKVLPGILFLWGLFLLGCGLSLATS

GRCYHLRHKVLPRWVWEKVPDPANSSSGQPHMEQVPEAQPLGDLPILEV

EEMEPPPVMESSQPAQATAPLDSGYEKHFLPTPEELGLLGPPRPQVLA

For purposes of the present disclosure, the numbering of amino acid residues of the human IL27Rα polypeptides as described herein is made in accordance with the numbering of this canonical sequence (UniProt Reference No Q6UWB1, SEQ ID NO:1). Amino acids 1-32 of SEQ ID NO:1 are identified as the signal peptide of hIL27Rα, amino acids 33-516 of SEQ ID NO:1 are identified as the extracellular domain, amino acids 517-537 of SEQ ID NO:1 are identified as the transmembrane domain, and amino acids 538-636 of SEQ ID NO:1 are identified as the intracellular domain.

For the purposes of generating antibodies that bind to the ECD of IL27Rα, immunization may be performed with the extracellular domain of the hIL27Rα. The extracellular domain of hIL27Rα is a 484 amino acid polypeptide of the sequence:

(SEQ ID NO: 192)
QGSAGPLQCYGVGPLGDLNCSWEPLGDLGAPSELHLQSQKYRSNKTQTV

AVAAGRSWVAIPREQLTMSDKLLVWGTKAGQPLWPPVFVNLETQMKPNA

PRLGPDVDFSEDDPLEATVHWAPPTWPSHKVLICQFHYRRCQEAAWTLL

EPELKTIPLTPVEIQDLELATGYKVYGRCRMEKEEDLWGEWSPILSFQT

PPSAPKDVWVSGNLCGTPGGEEPLLLWKAPGPCVQVSYKVWFWVGGREL

SPEGITCCCSLIPSGAEWARVSAVNATSWEPLTNLSLVCLDSASAPRSV

AVSSIAGSTELLVTWQPGPGEPLEHVVDWARDGDPLEKLNWVRLPPGNL

SALLPGNFTVGVPYRITVTAVSASGLASASSVWGFREELAPLVGPTLWR

LQDAPPGTPAIAWGEVPRHQLRGHLTHYTLCAQSGTSPSVCMNVSGNTQ

SVTLPDLPWGPCELWVTASTIAGQGPPGPILRLHLPDNTLRWK.

Mouse IL27Rα

In one embodiment, specifically bind to the extracellular domain of the mouse or murine IL27Rα receptor subunit (mIL27Rα). mIL27Rα is expressed as a 623 amino acid precursor comprising a 24 amino acid N-terminal signal sequence which is post-translationally cleaved to provide a 599 amino acid mature protein. The canonical full-length acid mIL27Rα precursor (including the 24 amino acid signal peptide) is a 623 amino acid polypeptide having the amino acid sequence:

(SEQ ID NO: 193)
MNRLRVARLTPLELLLSLMSLLLGTRPHGSPGPLQCYSVGPLGILNCSW

EPLGDLETPPVLYHQSQKYHPNRVWEVKVPSKQSWVTIPREQFTMADKL

LIWGTQKGRPLWSSVSVNLETQMKPDTPQIFSQVDISEEATLEATVQWA

PPVWPPQKVLICQFRYKECQAETWTRLEPQLKTDGLTPVEMQNLEPGTC

YQVSGRCQVENGYPWGEWSSPLSFQTPFLDPEDVWVSGTVCETSGKRAA

LLVWKDPRPCVQVTYTVWFGAGDITTTQEEVPCCKSPVPAWMEWAVVSP

GNSTSWVPPTNLSLVCLAPESAPCDVGVSSADGSPGIKVTWKQGTRKPL

EYVVDWAQDGDSLDKLNWTRLPPGNLSTLLPGEFKGGVPYRITVTAVYS

GGLAAAPSVWGFREELVPLAGPAVWRLPDDPPGTPVVAWGEVPRHQLRG

QATHYTFCIQSRGLSTVCRNVSSQTQTATLPNLHLGSFKLWVTVSTVAG

QGPPGPNLSLHLPDNRIRWKALPWFLSLWGLLLMGCGLSLASTRCLQAR

CLHWRHKLLPQWIWERVPDPANSNSGQPYIKEVSLPQPPKDGPILEVEE

VELQPVVESPKASAPIYSGYEKHFLPTPEELGLLV

For purposes of the present disclosure, the numbering of amino acid residues of the mIL27Rα polypeptides as described herein is made in accordance with the numbering of this canonical sequence (UniProt Reference No. O70394, SEQ ID NO:193). Amino acids 1-24 of SEQ ID NO: 193 are identified as the signal peptide of mIL27Rα, amino acids 23-510 of SEQ ID NO: 193 are identified as the extracellular domain, amino acids 511-531 of SEQ ID NO: 193 are identified as the transmembrane domain, and amino acids 532-623 of SEQ ID NO: 193 are identified as the intracellular domain.

For the purposes of generating antibodies that bind to the ECD of IL27Rα, immunization may be performed with the extracellular domain of the mIL27Rα. The extracellular domain of the mIL27Rα receptor is a 486 amino acid polypeptide of the sequence:

(SEQ ID NO: 194)
TRPHGSPGPLQCYSVGPLGILNCSWEPLGDLETPPVLYHQSQKYHPNRV

WEVKVPSKQSWVTIPREQFTMADKLLIWGTQKGRPLWSSVSVNLETQMK

PDTPQIFSQVDISEEATLEATVQWAPPVWPPQKVLICQFRYKECQAETW

TRLEPQLKTDGLTPVEMQNLEPGTCYQVSGRCQVENGYPWGEWSSPLSF

QTPFLDPEDVWVSGTVCETSGKRAALLVWKDPRPCVQVTYTVWFGAGDI

TTTQEEVPCCKSPVPAWMEWAVVSPGNSTSWVPPTNLSLVCLAPESAPC

DVGVSSADGSPGIKVTWKQGTRKPLEYVVDWAQDGDSLDKLNWTRLPPG

NLSTLLPGEFKGGVPYRITVTAVYSGGLAAAPSVWGFREELVPLAGPAV

WRLPDDPPGTPVVAWGEVPRHQLRGQATHYTFCIQSRGLSTVCRNVSSQ

TQTATLPNLHLGSFKLWVTVSTVAGQGPPGPNLSLHLPDNRIRWK

IL27Rα Binding Molecules and Single Domain Antibodies

In some embodiments, an IL27Rα binding molecule of the present disclosure is a single domain antibody (sdAb). The present disclosure relates to IL27Rα binding molecules comprising single domain antibodies (sdAbs) that specifically bind to the extracellular domain of the human IL27Rα isoform (hIL27Rα) which are found on all IL27Rα-expressing cells.

A single-domain antibody (sdAb) is an antibody containing a single monomeric variable antibody domain. Like a full-length antibody, sdAbs are able to bind specifically to an antigenic determinant. hIL27Rα binding VHH single-domain antibodies can be engineered from heavy chain antibodies isolated from Camelidae mammals (e.g., camels, llamas, dromedary, alpaca, and guanaco) immunized with the extracellular domain of hIL27Rα or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) *Antibodies* (Basel) 8(1); and De Vlieger, et al. (2018) *Antibodies* (Basel) 8(1). Alternatively, hIL27Rα single domain antibodies may be engineered from heavy chain antibodies isolated from the IgNAR heavy chain antibodies isolated from cartilaginous fishes immunized with the extracellular domain of hIL27Rα or an immunologically active fragment thereof hIL27Rα binding sdAbs may also be obtained by splitting the dimeric variable domains from immunoglobulin G (IgG) isotypes from other mammalian species including humans, rats, rabbits immunized with the extracellular domain of hIL27Rα or an immunologically active fragment thereof. Although most research into sdAbs is currently based on heavy chain variable domains, sdAbs derived from light chains have also been shown to bind specifically to the target proteins comprising the antigenic immunization sequence. Moller et al. *J. Biol Chem.* 285(49):38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IL27Rα binding molecules comprising a polypeptide having at least 75%, alternatively 80%, alternatively 90%, alternatively 95%, alternatively 98%, or alternatively 99% or 100% identity to a polypeptide of any one of SEQ ID NOS:2-25.

The present disclosure provides IL27Rα binding molecules comprising a polypeptide having at least 75%, alternatively 80%, alternatively 90%, alternatively 95%, alternatively 98%, or alternatively 99% or 100% identity to a polypeptide of any one of SEQ ID NOS:61-74.

The present disclosure provides IL27Rα binding molecules comprising a CDR1, a CDR2, and a CDR3 as described in a row of Table 1 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 provided herein.

The present disclosure provides IL27Rα binding molecules comprising a CDR1, a CDR2, and a CDR3 as described in a row of Table 3 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 3 provided herein.

Experimental

The single domain antibodies of the present disclosure were obtained from camels by immunization with an extracellular domain of a IL27Rα receptor. IL27Rα VHH molecules of the present disclosure of the present disclosure were generated in substantial accordance with the teaching of the Examples. Briefly, a camel was sequentially immunized with the ECD of the human IL27Rα and mouse IL27Rα over a period several weeks of by the subcutaneous an adjuvanted composition containing a recombinantly produced fusion proteins comprising the extracellular domain of the IL27Rα, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into E. coli to generate a phage library. Multiple rounds of biopanning of the phage library were conducted to identify VHHs that bound to the ECD of IL27Rα (human or mouse as appropriate). Individual phage clones were isolated for periplasmic extract ELISA (PE-ELISA) in a 96-well plate format and selective binding confirmed by colorimetric determination. The IL27Rα binding molecules that demonstrated specific binding to the IL27Rα antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence. The VHH molecules demonstrating specific binding to the hIL27Rα ECD antigen (anti-human IL27Rα VHHs) and the CDRs isolated from such VHHs are provided in Table 1. The VHH molecules demonstrating specific binding to the mIL27Rα ECD antigen (anti-mouse IL27Rα VHHs) and the CDRs isolated from such VHHs are provided in Table 3. Nucleic acid sequences encoding the VHHs of Table 1 and 3 are provide in Tables 2 and 4 respectively.

To more fully characterize the binding properties and evaluate binding affinity of the VHH molecules generated in accordance with the foregoing, representative examples of each of the human VHH clonotypes were subjected to analysis of by surface plasmon resonance in substantial accordance with the teaching of Example 5 herein. The results of these SPR studies are summarized in Table 6 below.

TABLE 6 anti-hIL274Ra Mono-Fc VHHs (ligand) binding to hIL27Ra-his
(Antigen: Origene, Catalog# TP307012)

| Ligand | SEQ ID NO: | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|---|
| hIL27R VHH1  | 2  | 3.0E+04 | 5.7E−04 | 19.0 | 142* | 1319 | 3564 | 4%  |
| hIL27R VHH15 | 16 | 9.1E+04 | 4.1E−04 | 4.5  | 102  | 305  | 824  | 12% |
| hIL27R VHH9  | 11 | 5.9E+04 | 1.0E−03 | 17   | 79   | 232  | 627  | 13% |
| hIL27R VHH19 | 21 | 1.5E+05 | 7.6E−04 | 5.2  | 115* | 210  | 568  | 20% |
| hIL27R VHH21 | 23 | 1.3E+05 | 7.7E−04 | 6.1  | 149* | 305  | 823  | 18% |

*Both association and dissociation kinetics constants might be suppressed at Rmax >100. If existing, this effect is likely cancelled in the kinetics ratio, i.e. affinity constant.

As demonstrated by the data presented in Table 6, above the IL27Rα VHH binding molecules exhibited specific binding to the antigen and provided a range of affinities for the IL27Rα antigen.

In some instances, due to sequence or structural similarities between the extracellular domains of IL27Rα receptors from various mammalian species, immunization with an antigen derived from a IL27Rα of a first mammalian species (e.g., the hIL27Rα-ECD) may provide antibodies which specifically bind to IL27Rα receptors of one or more additional mammalian species. Such antibodies are termed "cross reactive." For example, immunization of a camelid with a human derived antigen (e.g., the hIL27Rα-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL27Rα VHH" or "hIL27Rα VHH" merely denotes that the species of the IL27Rα antigen used for immunization of the camelid from which the VHH was derived was the human IL27Rα (e.g., the hIL27Rα, ECD, SEQ ID NO:192 but should not be understood as limiting with respect to the specific binding affinity of the VHH for hIL27Rα molecules of other mammalian species. Similarly, the use of the term "mouse IL27Rα VHH" or "mIL27Rα" merely denotes that the species of the IL27Rα antigen used for immunization of the camelid from which the VHH was derived was the murine IL27Rα (e.g., the mIL27Rα ECD, SEQ ID NO:194) but should not be understood as limiting with respect to the specific binding affinity of the VHH for IL27Rα molecules of other mammalian species.

Modified Forms of Single Domain Antibodies

CDR Grafted sdAbs

In some embodiments, the IL27Rα binding sdAb of the present disclosure is a CDR grafted IL27Rα binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides an IL27Rα binding molecule comprising a CDR grafted IL27Rα binding sdAb, said CDR-grafted IL27Rα binding sdAb comprising a set of CDRs1, 2, and 3 as shown in a row of the Table 3 above.

Chimeric and Humanized sdAbs

Any framework region can be used with the CDRs as described herein. In some embodiments, the IL27Rα binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IL27Rα binding sdAbs derived from hIL27Rα binding VHHs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

IL27Rα Binding Molecules Comprising Additional Agents

In some embodiments, an IL27Rα binding molecule of the present disclosure comprises an IL27Rα single domain antibody (sdAb) conjugated to one or more additional biologically active agents including but not limited to, therapeutic agents, chemically, optically or radioactively active agents, including combinations thereof. The conjugation of at least one such biologically, chemically, optically or radioactively active agent confer additional biological or chemical properties to IL27Rα binding sdAb, the combination providing an IL27Rα binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IL27Rα binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in an IL27Rα binding molecule as contemplated herein facilitates the release of a therapeutic agent into the intracellular cytoplasm upon internalization of the IL27Rα binding molecule. A non-cleavable linker would allow release upon digestion of the IL27Rα binding molecule of or it could be used with an agent that does not require release from the antibody (e.g., an imaging agent).

In some embodiments, where the IL27Rα binding molecule comprises an IL27Rα binding sdAb in stable association with an additional agent joined via a linker. A linker is a covalent linkage between two elements of an IL27Rα binding molecule (e.g., a hIL27Rα binding VHH and PEG polymer). A linker can be a covalent bond, chemical linker or a peptide linker. Suitable linkers include "flexible linkers" which are generally of sufficient length to permit some movement between the IL27Rα binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IL27Rα binding sdAbs disclosed herein. In some embodiments the linkers have the formula (GGGS)n (SEQ ID NO: 197), (GGGSG)n (SEQ ID NO: 198), (GGGGS)n (SEQ ID NO: 199), (GGS)nG (SEQ ID NO: 200), or (GGSG)n (SEQ ID NO: 201), wherein n is an integer selected from 1, 2, 3, 4, 5, 6, 7, 8, 9 and 10.

Immunomodulatory Agents

In some embodiments, IL27Rα binding molecules of the present disclosure are operably linked to immunomodulatory agent (immunoconjugates). Immunomodulatory agents that may conjugated to the hIL27Rα binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IL27Rα or cells expressing the IL27Rα.

Flag Tags

In some embodiments, IL27Rα binding molecules of the present disclosure are operably linked to an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL27Rα binding sdAb polypeptide further comprises a C-terminal c-myc epitope tag.

Chelating Peptides

In some embodiments, IL27Rα binding molecules of the present disclosure are operably linked to one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IL27Rα binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IL27Rα binding molecule are polypeptides comprising 3-6 contiguous histidine residues (SEQ ID NO: 202) such as a six-histidine $(His)_6$ peptide (SEQ ID NO: 195) and are frequently referred to in the art as "His-tags." In addition to providing a purification "handle" for the recombinant proteins or to facilitate immobilization on SPR sensor chips, such the conjugation of the h IL27Rα binding molecule to a chelating peptide facilitates the targeted delivery to IL27Rα expressing cells of transition metal ions as kinetically inert or kinetically labile complexes in substantial accordance with the teaching of Anderson, et al., (U.S. Pat. No. 5,439,829 issued Aug. 8, 1995 and Hale, J. E (1996) Analytical Biochemistry 231(1):46-49. The transition metal ion is a reporter molecule such as a fluorescent compound or radioactive agent, including as radiological imaging or therapeutic agents.

Carrier Molecules

In some embodiments the IL27Rα binding sdAbs of the present disclosure may be conjugated to one or more carrier molecules. Carrier molecules are typically large, slowly metabolized macromolecules which provide for stabilization and/or extended duration of action in vivo to distinguish such molecules from conventional carrier molecules used in the preparation of pharmaceutical formulations as described below. Examples of in vivo carriers that may be incorporated into IL27Rα binding molecules, but are not limited to: proteins (including but not limited to human serum albumin); fatty acids (acylation); polysaccharides (including but not limited to (N- and O-linked) sugars, sepharose, agarose, cellulose, or cellulose); polypeptides amino acid copolymers, acylation, or polysialylation, an polyethylene glycol (PEG) polymers.

Water Soluble Polymers

In some embodiments, the IL27Rα binding sdAb is conjugated to one or more water-soluble polymers. Examples of water soluble polymers useful in the practice of the present IL27Rα binding molecule include polyethylene glycol (PEG), poly-propylene glycol (PPG), polysaccharides (polyvinylpyrrolidone, copolymers of ethylene glycol and propylene glycol, poly(oxyethylated polyol), poly-olefinic alcohol, polysaccharides, poly-alpha-hydroxy acid, polyvinyl alcohol (PVA), polyphosphazene, polyoxazolines (POZ), poly(N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGylated polypeptide may be further referred to as monopegylated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, an IL27Rα binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IL27Rα binding molecules of the present disclosure possess an N-terminal glutamine ("1Q") residue. N-terminal glutamine residues have been observed to spontaneously cyclize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL27Rα binding molecules of the present disclosure, particularly when aldehyde chemistry is to be employed, the IL27Rα binding molecules possessing an amino acid at position 1 (e.g., 1Q) are substituted at position 1 with an alternative amino acid or are deleted at position 1 (e.g., des-1Q). In some embodiments, the IL27Rα binding molecules of the present disclosure comprise an amino acid substitution selected from the group Q1E and Q1D.

PEGs suitable for conjugation to a polypeptide sequence are generally soluble in water at room temperature, and have the general formula $$R(O-CH_2-CH_2)_nO-R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in an IL27Rα binding molecule is not restricted to any particular range. The PEG component of an IL27Rα binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IL27Rα binding molecule, the PEG is a 40 kD branched PEG comprising two 20 kD arms.

The present disclosure also contemplates an IL27Rα binding molecule comprising more than one PEG moiety wherein the PEGs have different sizes values, and thus the various different PEGs are present in specific ratios. For example, in the preparation of a PEGylated IL27Rα binding molecule, some compositions comprise a mixture of mono-, di-, tri-, and quadra-PEGylated sdAb conjugates. In some compositions, the percentage of mono-PEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimidyl carbonate PEG (SC-PEG; see, e.g., Zalipsky, et al. (1992) Biotechnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to an IL27Rα binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IL27Rα binding molecule may be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 on one chain and Y349 on the second chain which results in a stabilizing disulfide bridge between the two antibody heavy chains in the Fc region (Carter, et al. (2001) Immunol Methods 248, 7-15). The knob-into-hole format is used to facilitate the expression of a first polypeptide (e.g., an IL27Rα binding sdAb) on a first Fc monomer with a "knob" modification and a second polypeptide on the second Fc monomer possessing a "hole" modification to facilitate the expression of heterodimeric polypeptide conjugates.

Targeting Domains

In some embodiments, the IL27Rα binding molecule is provided as a component of a multivalent (e.g., bivalent) fusion protein with a polypeptide sequence ("targeting domain") to facilitate selective binding to particular cell type or tissue expressing a cell surface molecule that specifically binds to such targeting domain, optionally incorporating a linker between the IL27Rα binding sdAb sequence and the sequence of the targeting domain of the fusion protein.

In some embodiments of the IL27Rα binding molecule, the IL27Rα binding molecule may be targeted to a particular cell type cell by incorporation of a targeting domain into the structure of the IL27Rα binding molecules. As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is an IL27Rα+ T cell.

In some embodiments, the targeting domain is a ligand for a receptor. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, IL34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a multivalent binding molecule, the multivalent binding molecule comprising: (a) an IL27Rα binding molecule and (b) a second binding molecule that specifically binds to the extracellular domain of a second cell surface molecule, wherein the IL27Rα binding molecule and second binding molecule are operably linked, optionally through a chemical or polypeptide linker. In some embodiments, the IL27Rα binding molecules of the present disclosure are useful in the preparation of the multivalent binding molecules described in Gonzalez, et al. PCT/US2018/021301 published as WO 2018/182935 A1 on Oct. 4, 2018. In some aspects, the second binding molecule specifically binds to the extracellular domain of: (i) a component of cytokine receptor that activates the JAK/STAT pathway in the cell; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/F1k2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TNFRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2 (TNFRSF10D), EDAR, Fas (TNFRSF6), HVEM (TNFRSF14), LTBR (TNFRSF3), OX40 (TNFRSF4), RANK (TNFRSF11A), TACI (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16).

In some embodiments, the targeting domain is a polypeptide that specifically binds to a cell surface molecule associated with a tumor cell (e.g., a cognate ligand for a tumor cell receptor) selected from the group consisting of GD2, BCMA, CD19, CD33, CD38, CD70, GD2, IL3Ra2, CD19, mesothelin, Her2, EpCam, Muc1, ROR1, CD133, CEA, EGRFRVIII, PSCA, GPC3, Pan-ErbB and FAP.

In some embodiments, the targeting domain of the IL27Rα binding molecule is an antibody (as defined hereinabove to include molecules such as VHHs, scFvs, etc.) Examples of antibodies that may incorporated as a targeting domain of an IL27Rα binding molecule include but are not limited to the group consisting of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Muc1 antibodies, anti-ROR1 antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody Labels In some embodiments, IL27Rα binding molecules of the present disclosure are operably linked to a label. In some embodiments, the label is incorporated to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment an IL27Rα binding sdAb an IL27Rα binding VHH) molecule in stable association (e.g., covalent, coordinate covalent) with an imaging labels. The term imaging labels is used to describe any of a variety of compounds a signature that facilitates identification, tracing and/or localization of the IL27Rα binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I) Gallium-67 ($^{67}$Ga), and Lutetium-177 ($^{177}$Lu), phosphorus ($^{32}$P), carbon ($^{14}$C), tritium ($^{3}$H), yttrium ($^{90}$Y), actinium ($^{225}$Ac), astatine ($^{211}$At) rhenium ($^{186}$Re), bismuth ($^{212}$Bi or $^{213}$Bi), and rhodium ($^{188}$Rh).

Therapeutic Agents

In some embodiments, IL27Rα binding molecules of the present disclosure are operably linked to a therapeutic agent. Examples of therapeutic agents include therapeutic small molecule (e.g., chemotherapeutic agents) or biologic therapeutic agents including antibodies, cytotoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies, chemotherapeutic agents, as described more fully herein.

In some embodiments, the therapeutic agent which may be incorporated into the IL27Rα binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{177}$Lu), actinium-225 ($^{225}$Ac), astatine-211 ($^{211}$At), rhenium-186 ($^{186}$Re) bismuth-212 ($^{212}$Bi), bismuth-213 ($^{213}$Bi), and rhodium-188 ($^{188}$Rh).

In some embodiments, IL27Rα binding molecules of the present disclosure are operably linked to a cytotoxic agent (or derivative thereof), such maytansinol or the DM1 maytansinoid), a taxane, or a calicheamicin, Pseudomonas exotoxin A, deBouganin, ricin toxin, diphtheria toxin, an amatoxin, such as a-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

Synthesis of IL27Rα Binding Molecules:

In some embodiments, the IL27Rα binding molecules of the present disclosure are polypeptides. However, in some embodiments, only a portion of the IL27Rα binding molecule is a polypeptide, for example where the IL27Rα binding molecule comprises a non-peptidyl domain (e.g., a PEG IL27Rα binding sdAb conjugate, a radionucleotide IL27Rα binding sdAb conjugate, or a small molecule IL27Rα binding sdAb conjugate). The following provides guidance to enable the solid phase and recombinant synthesis of the polypeptide portions (domains) of IL27Rα binding molecules of the present disclosure. In those embodiments where only a portion of the IL27Rα binding molecule is a polypeptide, it will be understood that the peptidyl domain(s) of the IL27Rα binding molecule are an intermediate in the process which may undergo further processing to complete the synthesis of the desired IL27Rα binding molecules. The polypeptide domains of IL27Rα binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IL27Rα binding molecules can be chemically synthesized. Chemically synthesized polypeptides are routinely generated by those of skill in the art. Chemical synthesis includes direct synthesis of a peptide by chemical means of the polypeptide domains of IL27Rα binding molecules exhibiting the properties described. This method can incorporate both natural and unnatural amino acids at desired positions that facilitate linkage of particular molecules (e.g., PEG).

In some embodiments, the polypeptide domains of IL27Rα binding molecules of the present disclosure may be prepared by chemical synthesis. The chemical synthesis of the polypeptide domains of IL27Rα binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IL27Rα binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

Alternatively, polypeptide domains of IL27Rα binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IL27Rα Binding Molecule

In some embodiments, the polypeptide domains of IL27Rα binding molecule is produced by recombinant methods using a nucleic acid sequence encoding the polypeptide domains of IL27Rα binding molecule (or fusion protein comprising the polypeptide domains of IL27Rα binding molecule). The nucleic acid sequence encoding the desired polypeptide domains of IL27Rα binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IL27Rα binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IL27Rα binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IL27Rα binding molecule may be obtained from various commercial sources that provide custom synthesis of nucleic acid sequences. Amino acid sequence variants of the HUMAN IL27Rα binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IL27Rα binding molecule and expressing those sequences in a suitably transformed host include, but are not limited to, using a PCR-assisted mutagenesis technique. Mutations that consist of deletions or additions of amino acid residues to polypeptide domains of IL27Rα binding molecule can also be made with standard recombinant techniques. In the event of a deletion or addition, the nucleic acid molecule encoding polypeptide domains of IL27Rα binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IL27Rα binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IL27Rα binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL27Rα binding molecule (i.e. the human IL27Rα signal sequence). The inclusion of a signal sequence depends on whether it is desired to secrete the IL27Rα binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL27Rα binding molecule into the culture medium as described in Singh, U.S. Pat. No. 7,198,919 B1.

In the event the polypeptide domain of IL27Rα binding molecules to be expressed is to be expressed as a chimera (e.g., a fusion protein comprising an IL27Rα binding molecule and a heterologous polypeptide sequence), the chimeric protein can be encoded by a hybrid nucleic acid molecule comprising a first sequence that encodes all or part of the polypeptide domains of IL27Rα binding molecule and a second sequence that encodes all or part of the heterologous polypeptide. For example, polypeptide domains of IL27Rα binding molecules described herein may be fused to a hexa-histidine tag (SEQ ID NO: 195) to facilitate purification of bacterially expressed protein, or to a hexa-histidine (SEQ ID NO: 195), hemagglutinin, or Fc tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IL27Rα binding molecule. For example, the N-terminus may be linked to a targeting domain and the C-terminus linked to a hexa-histidine tag (SEQ ID NO: 195) purification handle.

The complete amino acid sequence of the polypeptide domain of IL27Rα binding molecule (or fusion/chimera) to be expressed can be used to construct a back-translated gene. A DNA oligomer containing a nucleotide sequence coding for the polypeptide domain of IL27Rα binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IL27Rα binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors

Once assembled (by synthesis, site-directed mutagenesis or another method), the nucleic acid sequence encoding polypeptide domains of IL27Rα binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IL27Rα binding molecules of the present disclosure contain a regulatory sequence that is recognized by the host organism and is operably linked to nucleic acid sequence encoding the polypeptide domains of IL27Rα binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL27Rα binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IL27Rα binding molecule. A cell of the present disclosure is a transfected cell, i.e., a cell into which a nucleic acid molecule, for example a nucleic acid molecule encoding a polypeptide domains of IL27Rα binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IL27Rα binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IL27Rα binding molecule or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IL27Rα binding molecule can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IL27Rα binding molecule may be glycosylated or unglycosylated depending on the host organism used to produce the IL27Rα binding molecule. If bacteria are chosen as the host then the polypeptide domains of IL27Rα binding sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the elimination of the Asn-X-Ser (N-X-S) N-linked glycosylation motif may be achieved by the incorporation of conservative amino acid substitution of the Asn (N) residue and/or Ser (S) residue of the Asn-X-Ser (N-X-S) N-linked glycosylation motif. In some embodiments, the elimination of the Asn-X-Thr (N-X-T) N-linked glycosylation motif may be achieved by the incorporation of conservative amino acid substitution of the Asn (N) residue and/or Thr (T) residue of the Asn-X-Thr (N-X-T) N-linked glycosylation motif. In some embodiments, elimination of the As procaryotic host cells do not provide the mechanism for glycosylation of recombinant proteins, when employing a procaryotic expression system to produce a recombinant Crissrecombinant IL27Rα binding sdAb the modification of the sequence to eliminate the N-linked glycosylation sites may be obviated.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs of the can be introduced into host cells to thereby produce the recombinant polypeptide domains of IL27Rα binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IL27Rα binding polypeptides can be recovered from the culture medium as a secreted polypeptide if a secretion leader sequence is employed. Alternatively, the IL27Rα binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of IL27Rα binding molecule produced by the transformed host can be purified according to any suitable method. IL27Rα binding molecules can be isolated from inclusion bodies generated in *E. coli*, or from conditioned medium from either mammalian or yeast cultures producing a given IL27Rα binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IL27Rα binding molecule produced in accordance with the foregoing can be confirmed by an IL27Rα binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Inhibition of IL27Rα Activity

In one embodiment, the present disclosure provides a method of modulating the activity of cells expressing the IL27Rα by the administration of an IL27Rα binding molecule to a subject in an amount sufficient to interfere with the activity of receptors comprising the of IL27Rα. The present disclosure further provides a method of modulating the activity of cells expressing the IL27Rα in a mixed population of cells comprising contacting said population of cells, in vivo and/or ex vivo, with an IL27Rα binding molecule or complex of the present disclosure to in an amount sufficient to interfere with the activity of receptors comprising the IL27Rα.

Identification Isolation, Enrichment or Depletion of IL27Rα+ Cells

In one embodiment, the present disclosure provides a method of use of the IL27Rα binding molecules of the present disclosure useful in a process for in the isolation, enrichment or depletion of IL27Rα+ cells from a biological sample comprising IL27Rα+ cells. The biological sample may comprise cells of blood origin such as PBMC, T cells, B cells of cell culture origin or of tissue origin such as brain or bone marrow. Processes suitable for the isolation, enrichment or depletion of IL27Rα+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IL27Rα+ cells through the use of an IL27Rα binding molecule as described herein.

In one embodiment, the sorting procedure employs an IL27Rα binding molecule comprising a fluorescent label for use in FACS isolation or depletion of IL27Rα+ cells from a sample. The fluorescent label may be attached to the sdAb of the IL27Rα binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IL27Rα+ cells may be separated from a mixed cell population using conventional FACS technology.

In an alternative embodiment, the selection procedure employs IL27Rα binding molecules of the present disclosure (e.g., an IL27Rα binding VHH) are conjugated to magnetic particles which provide magnetic labeling of the IL27Rα+ cells for use in magnetic cell separation procedures. In one embodiment the method comprises: (a) conjugation of one or more IL27Rα binding molecule of the present disclosure (e.g., an IL27Rα binding VHH) to a magnetic particle; (b) creating a mixture by contacting the biological sample with a quantity of the magnetic particles conjugated to IL27Rα binding molecule; (c) subjecting to a magnetic field such that the magnetically labelled IL27Rα+ cells are retained; (d) removing the non-magnetically labelled cells from the mixture; and (e) removal of the magnetic field enabling isolation of the IL27Rα+ cells.

The cell selection procedure (e.g., FACS or magnetic separation) results in two products: (a) a population of cells depleted of IL27Rα+ cells and (b) a population of cells enriched for IL27Rα+ cells. Each of these populations may be further processed by convention procedures to identify particular IL27Rα+ or IL27Rα− cell subsets which may be useful in research, diagnostic or clinical applications. For example, isolation of specific IL27Rα+ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IL27Rα binding molecule may be used for depletion of IL27Rα-expressing cells from a biological sample comprising IL27Rα-expressing cells such peripheral blood or lymphoid tissue which may optionally be further processed for further isolation of IL27Rα+naïve T cell subsets, isolation human IL27Rα+ memory T cells from a population of CD4+ or CD8+ cells, or isolation of human IL27RαRA+naïve T cells from presorted CD4+ or CD8+ cells by depletion of IL27Rα+ cells. In one embodiment, the IL27Rα binding molecule provides a method of generating a population of cells enriched for naïve Tregs from a biological sample, the method comprising depleting IL27Rα+ cells using an IL27Rα binding molecule of the present disclosure as described above, optionally further comprising the steps of depleting CD8+ and/or CD19+ cells. The IL27Rα+ depleted cell population may optionally be further expanded in vitro for particular cell types to in the preparation of a cell product comprising a therapeutically effective amount of the IL27Rα+ depleted cell product which may be administered to a subject suffering from a disease, disorder or condition. The IL27Rα+ enriched cell population may optionally be further expanded in vitro to in the preparation of a cell product comprising a therapeutically effective amount of the IL27Rα+ cells.

Kits

The present disclosure also contemplates kits comprising pharmaceutical compositions of IL27Rα binding molecules. The kits are generally in the form of a physical structure housing various components, as described below, and can be utilized, for example, in practicing the methods described above. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL27Rα binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IL27Rα binding molecule, and are not intended to limit the scope of what the inventors regard as their IL27Rα binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IL27Rα binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid; PBMCs=primary peripheral blood mononuclear cells; FBS=fetal bovine serum; FCS=fetal calf serum; HEPES=4-(2-hydroxyethyl)-1piperazineethanesulfonic acid; LPS=lipopolysaccharide; ATCC=American Type Culture Collection

Example 1. Immunization Protocol

The process for isolation of the anti-hIL27Rα VHHs was initiated by immunization of a camel with a polypeptide corresponding to amino acids 33-516 of hIL27Rα, (UNIPROT Reference No. Q6UWB1). The process for isolation of the anti-mIL27Rα VHHs was the initiated by immunization of a camel with the with the 201 amino acid extracellular domain of the mIL27Rα, amino acids 25-510 of the mIL27Rα precursor (UNIPROT Reference No. O70394). With respect to each antigen, the following methodology was used to identify and isolate the VHHs.

The synthetic DNA sequence encoding the antigen was inserted into the pFUSE_hIgG1 Fc2 vector (Generay Biotechnology) and transfected into the HEK293F mammalian cell host cell for expression. The antigen is expressed as an Fc fusion protein which is purified using Protein A chromatography. The antigen was diluted with 1×PBS (antigen total about 1 mg). The quality was estimated by SDS-PAGE to ensure the purity was sufficient (>80%) for immunization. The camel was acclimated at the facility for at least 7 days before immunization. The immunization with the antigen was conducted using once weekly administration of the antigen over a period of 7 weeks. For the initial immunization, the immunogen was prepared as follows: 10 mL of complete Freund's Adjuvant (CFA) was added into mortar, then 10 mL antigen in 1×PBS was slowly added into the mortar with the pestle grinding and sample ground until the antigen was emulsified until milky white and hard to disperse. For the subsequent six immunizations (weeks 2-7) in the immunization protocol, immunogen was prepared as above except that Incomplete Freund's Adjuvant (IFA) was used in place of CFA. At least six sites on the camel were injected subcutaneously with approximately 2 ml of the emulsified antigen for a total of approximately 10 mL per camel. When injecting the antigen, the needle is maintained in the in the subcutaneous space for approximately 10 to 15 seconds after each injection to avoid leakage of the emulsion.

Example 2. Phage Library Construction

A blood sample was collected from the camel three days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with Pst I and Not I, subsequently, ligated to pMECS/Nb recombinant. After ligation, the products were transformed into Escherichia coli (E. coli) TG1 cells by electroporation. The transformants were enriched in growth medium, followed by transfer to 2YT+2% glucose agar plates.

Example 3: Isolation of Antigen Specific VHHs

Bio-panning of the phage library was conducted to identify VHHs that bind IL27Rα. A 96-well plate was coated with IL27Rα and the phage library was incubated in each well to allow phage-expressing IL27Rα reactive VHH to bind to the IL27Rα on the plate. Non-specifically bound phage were washed off and the specifically bound phage isolated. After the selection, the enriched phage library expressing IL27Rα reactive VHH were amplified in TG1 cells. The aforementioned bio-panning process was repeated for 2-3 rounds to enrich the library for VHH selective for IL27Rα.

Example 4: Identification of Antibodies Exhibiting Specific Binding to IFNgR1

Upon completion of the biopanning of Example 3, three 96-well plates of individual phage clones were isolated in order to perform periplasmic extract ELISA (PE-ELISA) on IL27Rα coated plates to identify positive VHH binders that selectively bound IFNgR1. A 96-well plate was coated with IL27Rα and PBS under the same conditions. Next, wells were blocked at 37° C. for 1 h. Then, 100 µl of extracted antibodies was added to each well and incubated for 1 h. Subsequently, 100 µl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader. Antibodies with absorbance of the antigen-coated well at least threefold greater than PBS-coated control were defined as exhibiting specific binding to IL27Rα. Positive clones were sequenced, and sequences analyzed to identify unique clonotypes.

Example 5. Evaluation of Binding Affinity Via Surface Plasmon Resonance

A representative example from each hIL27Rα VHH clonotype generated in accordance with Examples 1-3 was selected for evaluation of binding via SPR as follows. Evaluation of binding affinity of the hIL27Rα binding molecules corresponding to SEQ ID NOS 2-27 was conducted using surface plasmon resonance (SPR) in substantial accordance with the following procedure. All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with a Protein A derivatized sensor chip (Cytiva). Mono-Fc VHH ligands were flowed at 5 µl/min for variable time ranging from 18 to 300 seconds, reaching the capture loads listed in the tables below. Following ligand capture, injections of a 2-fold dilution series of the extracellular domain of the IL27Rα-receptor modified to incorporate a C-terminal poly-His sequence, typically comprising at least five concentrations between 1 µM and 1 nM, were performed in either high performance or single cycle kinetics mode. Surface regeneration was achieved by flowing 10 mM glycine-HCl, pH 1.5 (60 seconds, 50 µL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated $R_{max}$ values were generated using the equation: Rmax=Load (RU)×valency of ligand×(Molecular weight of analyte/Molecular weight of ligand). Surface activity was defined as the ratio of experimental/calculated Rmax. The results of these binding affinity experiments are provided in Table 6.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

---

The invention claimed is:

1. An Interleukin-27 receptor alpha (IL27Rα) binding molecule that specifically binds to the extracellular domain of IL27Rα, wherein the IL27Rα binding molecule comprises a single domain antibody comprising:
   a complementarity determining region (CDR) 1 comprising the amino acid sequence of SEQ ID NO:50, a CDR2 comprising the amino acid sequence of SEQ ID NO:51, and a CDR3 comprising the amino acid sequence of SEQ ID NO:52; or
   a CDR1 comprising the amino acid sequence of SEQ ID NO:26, a CDR2 comprising the amino acid sequence of SEQ ID NO:27, and a CDR3 comprising the amino acid sequence of SEQ ID NO: 28; or
   a CDR1 comprising the amino acid sequence of SEQ ID NO:29, a CDR2 comprising the amino acid sequence of SEQ ID NO:30, and a CDR3 comprising the amino acid sequence of SEQ ID NO: 31; or
   a CDR1 comprising the amino acid sequence of SEQ ID NO:32, a CDR2 comprising the amino acid sequence of SEQ ID NO:33, and a CDR3 comprising the amino acid sequence of SEQ ID NO: 34; or
   a CDR1 comprising the amino acid sequence of SEQ ID NO:35, a CDR2 comprising the amino acid sequence of SEQ ID NO:36, and a CDR3 comprising the amino acid sequence of SEQ ID NO: 37; or
   a CDR1 comprising the amino acid sequence of SEQ ID NO:38, a CDR2 comprising the amino acid sequence of SEQ ID NO:39, and a CDR3 comprising the amino acid sequence of SEQ ID NO: 40; or
   a CDR1 comprising the amino acid sequence of SEQ ID NO:41, a CDR2 comprising the amino acid sequence of SEQ ID NO:42, and a CDR3 comprising the amino acid sequence of SEQ ID NO: 43; or
   a CDR1 comprising the amino acid sequence of SEQ ID NO:44, a CDR2 comprising the amino acid sequence of SEQ ID NO:45, and a CDR3 comprising the amino acid sequence of SEQ ID NO: 46; or
   a CDR1 comprising the amino acid sequence of SEQ ID NO:47, a CDR2 comprising the amino acid sequence of SEQ ID NO:48, and a CDR3 comprising the amino acid sequence of SEQ ID NO: 49; or
   a CDR1 comprising the amino acid sequence of SEQ ID NO:53, a CDR2 comprising the amino acid sequence of SEQ ID NO:54, and a CDR3 comprising the amino acid sequence of SEQ ID NO: 55; or
   a CDR1 comprising the amino acid sequence of SEQ ID NO:56, a CDR2 comprising the amino acid sequence of SEQ ID NO:57, and a CDR3 comprising the amino acid sequence of SEQ ID NO: 58; or
   a CDR1 comprising the amino acid sequence of SEQ ID NO:59, a CDR2 comprising the amino acid sequence of SEQ ID NO:60, and a CDR3 comprising the amino acid sequence of SEQ ID NO: 61; or
   a CDR1 comprising the amino acid sequence of SEQ ID NO:62, a CDR2 comprising the amino acid sequence of SEQ ID NO:63, and a CDR3 comprising the amino acid sequence of SEQ ID NO: 64; or a CDR1 comprising the amino acid sequence of SEQ ID NO:65, a CDR2 comprising the amino acid sequence of SEQ ID NO:66, and a CDR3 comprising the amino acid sequence of SEQ ID NO: 67; or a CDR1 comprising the amino acid sequence of SEQ ID NO:68, a CDR2 comprising the amino acid sequence of SEQ ID NO:69, and a CDR3 comprising the amino acid sequence of SEQ ID NO: 70; or a CDR1 comprising the amino acid sequence of SEQ ID NO:71, a CDR2 comprising the amino acid sequence of SEQ ID NO:72, and a CDR3 comprising the amino acid sequence of SEQ ID NO: 73; or a CDR1 comprising the amino acid sequence of SEQ ID NO:74, a CDR2 comprising the amino acid sequence of SEQ ID NO:75, and a CDR3 comprising the amino acid sequence of SEQ ID NO: 76; or a CDR1 comprising the amino acid sequence of SEQ ID NO:77, a CDR2 comprising the amino acid sequence of SEQ ID NO:78, and a CDR3 comprising the amino acid sequence of SEQ ID NO: 79; or a CDR1 comprising the amino acid sequence of SEQ ID NO:80, a CDR2 comprising the amino acid sequence of SEQ ID NO:81, and a CDR3 comprising the amino acid sequence of SEQ ID NO: 82; or a CDR1 comprising the amino acid sequence of SEQ ID NO:83, a CDR2 comprising the amino acid sequence of SEQ ID NO:84, and a CDR3 comprising the amino acid sequence of SEQ ID NO: 85; or a CDR1 comprising the amino acid sequence of SEQ ID NO:86, a CDR2 comprising the amino acid sequence of SEQ ID NO:87, and a CDR3 comprising the amino acid sequence of SEQ ID NO: 88; or a CDR1 comprising the amino acid sequence of SEQ ID NO:89, a CDR2 comprising the amino acid sequence of SEQ ID NO:90, and a CDR3 comprising the amino acid sequence of SEQ ID NO: 91; or a CDR1 comprising the amino acid sequence of SEQ ID NO:92, a CDR2 comprising the amino acid sequence of SEQ ID NO:93, and a CDR3 comprising the amino acid sequence of SEQ ID NO: 94; or a CDR1 comprising the amino acid sequence of SEQ ID NO:95, a CDR2 comprising the amino acid sequence of SEQ ID NO:96, and a CDR3 comprising the amino acid sequence of SEQ ID NO: 97.

2. The IL27Rα binding molecule of claim 1, wherein the IL27Rα binding molecule is a $V_H H$.

3. The IL27Rα binding molecule of claim 1, wherein the single domain antibody is humanized or comprises CDRs grafted onto a heterologous framework.

4. The IL27Rα binding molecule of claim 1, further comprising a labeling agent, an imaging agent, and/or a therapeutic agent.

5. A kit comprising the IL27Rα binding molecule of claim 1.

6. The IL27Rα binding protein of claim 1, wherein the CDR1 comprises the amino acid sequence of SEQ ID NO: 50; the CDR2 comprises the amino acid sequence of SEQ ID NO: 51; and the CDR3 comprises the amino acid sequence of SEQ ID NO: 52.

7. The IL27Rα binding protein of claim 1, wherein the single domain antibody comprises the amino acid sequence of SEQ ID NO: 10.

8. The IL27Rα binding protein of claim 1, wherein the CDR1 comprises the amino acid sequence of SEQ ID NO: 53; the CDR2 comprises the amino acid sequence of SEQ ID NO: 54; and the CDR3 comprises the amino acid sequence of SEQ ID NO: 55.

9. The IL27Rα binding protein of claim 8, wherein the single domain antibody comprises the amino acid sequence of SEQ ID NO: 11.

10. The IL27Rα binding protein of claim 1, wherein the CDR1 comprises the amino acid sequence of SEQ ID NO: 26; the CDR2 comprises the amino acid sequence of SEQ ID NO: 27; and the CDR3 comprises the amino acid sequence of SEQ ID NO: 28.

11. The IL27Rα binding protein of claim 10, wherein the single domain antibody comprises the amino acid sequence of SEQ ID NO: 2.

12. The IL27Rα binding protein of claim 1, wherein the CDR1 comprises the amino acid sequence of SEQ ID NO: 29; the CDR2 comprises the amino acid sequence of SEQ ID NO: 30; and the CDR3 comprises the amino acid sequence of SEQ ID NO: 31.

13. The IL27Rα binding protein of claim 12, wherein the single domain antibody comprises the amino acid sequence of SEQ ID NO: 3.

14. The IL27Rα binding protein of claim 1, wherein the CDR1 comprises the amino acid sequence of SEQ ID NO: 32; the CDR2 comprises the amino acid sequence of SEQ ID NO: 33; and the CDR3 comprises the amino acid sequence of SEQ ID NO: 34.

15. The IL27Rα binding protein of claim 14, wherein the single domain antibody comprises the amino acid sequence of SEQ ID NO: 4.

16. The IL27Rα binding protein of claim 1, wherein the CDR1 comprises the amino acid sequence of SEQ ID NO: 35; the CDR2 comprises the amino acid sequence of SEQ ID NO: 36; and the CDR3 comprises the amino acid sequence of SEQ ID NO: 37.

17. The IL27Rα binding protein of claim 16, wherein the single domain antibody comprises the amino acid sequence of SEQ ID NO: 5.

18. The IL27Rα binding protein of claim 1, wherein the CDR1 comprises the amino acid sequence of SEQ ID NO: 38; the CDR2 comprises the amino acid sequence of SEQ ID NO: 39; and the CDR3 comprises the amino acid sequence of SEQ ID NO: 40.

19. The IL27Rα binding protein of claim 18, wherein the single domain antibody comprises the amino acid sequence of SEQ ID NO: 6.

20. The IL27Rα binding protein of claim 1, wherein the CDR1 comprises the amino acid sequence of SEQ ID NO: 41; the CDR2 comprises the amino acid sequence of SEQ ID NO: 42; and the CDR3 comprises the amino acid sequence of SEQ ID NO: 43.

21. The IL27Rα binding protein of claim 20, wherein the single domain antibody comprises the amino acid sequence of SEQ ID NO: 7.

22. The IL27Rα binding protein of claim 1, wherein the CDR1 comprises the amino acid sequence of SEQ ID NO: 44; the CDR2 comprises the amino acid sequence of SEQ ID NO: 45; and the CDR3 comprises the amino acid sequence of SEQ ID NO: 46.

23. The IL27Rα binding protein of claim 22, wherein the single domain antibody comprises the amino acid sequence of SEQ ID NO: 8.

24. The IL27Rα binding protein of claim 1, wherein the CDR1 comprises the amino acid sequence of SEQ ID NO: 47; the CDR2 comprises the amino acid sequence of SEQ ID NO: 48; and the CDR3 comprises the amino acid sequence of SEQ ID NO: 49.

25. The IL27Rα binding protein of claim 24, wherein the single domain antibody comprises the amino acid sequence of SEQ ID NO: 9.

26. The IL27Rα binding protein of claim 1, wherein the CDR1 comprises the amino acid sequence of SEQ ID NO: 56; the CDR2 comprises the amino acid sequence of SEQ ID NO: 57; and the CDR3 comprises the amino acid sequence of SEQ ID NO: 58.

27. The IL27Rα binding protein of claim 26, wherein the single domain antibody comprises the amino acid sequence of SEQ ID NO: 12.

28. The IL27Rα binding protein of claim 1, wherein the CDR1 comprises the amino acid sequence of SEQ ID NO: 59; the CDR2 comprises the amino acid sequence of SEQ ID NO: 60; and the CDR3 comprises the amino acid sequence of SEQ ID NO: 61.

29. The IL27Rα binding protein of claim 28, wherein the single domain antibody comprises the amino acid sequence of SEQ ID NO: 13.

30. The IL27Rα binding protein of claim 1, wherein the CDR1 comprises the amino acid sequence of SEQ ID NO: 62; the CDR2 comprises the amino acid sequence of SEQ ID NO: 63; and the CDR3 comprises the amino acid sequence of SEQ ID NO: 64.

31. The IL27Rα binding protein of claim 30, wherein the single domain antibody comprises the amino acid sequence of SEQ ID NO: 14.

32. The IL27Rα binding protein of claim 1, wherein the CDR1 comprises the amino acid sequence of SEQ ID NO: 65; the CDR2 comprises the amino acid sequence of SEQ ID NO: 66; and the CDR3 comprises the amino acid sequence of SEQ ID NO: 67.

33. The IL27Rα binding protein of claim 32, wherein the single domain antibody comprises the amino acid sequence of SEQ ID NO: 15.

34. The IL27Rα binding protein of claim 1, wherein the CDR1 comprises the amino acid sequence of SEQ ID NO: 68; the CDR2 comprises the amino acid sequence of SEQ ID NO: 69; and the CDR3 comprises the amino acid sequence of SEQ ID NO: 70.

35. The IL27Rα binding protein of claim 34, wherein the single domain antibody comprises the amino acid sequence of SEQ ID NO: 16.

36. The IL27Rα binding protein of claim 1, wherein the CDR1 comprises the amino acid sequence of SEQ ID NO: 71; the CDR2 comprises the amino acid sequence of SEQ ID NO: 72; and the CDR3 comprises the amino acid sequence of SEQ ID NO: 73.

37. The IL27Rα binding protein of claim 36, wherein the single domain antibody comprises the amino acid sequence of SEQ ID NO: 17.

38. The IL27Rα binding protein of claim 1, wherein the CDR1 comprises the amino acid sequence of SEQ ID NO: 74; the CDR2 comprises the amino acid sequence of SEQ ID NO: 75; and the CDR3 comprises the amino acid sequence of SEQ ID NO: 76.

39. The IL27Rα binding protein of claim 38, wherein the single domain antibody comprises the amino acid sequence of SEQ ID NO: 18.

40. The IL27Rα binding protein of claim 1, wherein the CDR1 comprises the amino acid sequence of SEQ ID NO: 77; the CDR2 comprises the amino acid sequence of SEQ ID NO: 78; and the CDR3 comprises the amino acid sequence of SEQ ID NO: 79.

41. The IL27Rα binding protein of claim 40, wherein the single domain antibody comprises the amino acid sequence of SEQ ID NO: 19.

42. The IL27Rα binding protein of claim 1, wherein the CDR1 comprises the amino acid sequence of SEQ ID NO: 80; the CDR2 comprises the amino acid sequence of SEQ ID NO: 81; and the CDR3 comprises the amino acid sequence of SEQ ID NO: 82.

43. The IL27Rα binding protein of claim 42, wherein the single domain antibody comprises the amino acid sequence of SEQ ID NO: 20.

44. The IL27Rα binding protein of claim 1, wherein the CDR1 comprises the amino acid sequence of SEQ ID NO: 83; the CDR2 comprises the amino acid sequence of SEQ ID NO: 84; and the CDR3 comprises the amino acid sequence of SEQ ID NO: 85.

45. The IL27Rα binding protein of claim 44, wherein the single domain antibody comprises the amino acid sequence of SEQ ID NO: 21.

46. The IL27Rα binding protein of claim 1, wherein the CDR1 comprises the amino acid sequence of SEQ ID NO: 86; the CDR2 comprises the amino acid sequence of SEQ ID NO: 87; and the CDR3 comprises the amino acid sequence of SEQ ID NO: 88.

47. The IL27Rα binding protein of claim 46, wherein the single domain antibody comprises the amino acid sequence of SEQ ID NO: 22.

48. The IL27Rα binding protein of claim 1, wherein the CDR1 comprises the amino acid sequence of SEQ ID NO: 89; the CDR2 comprises the amino acid sequence of SEQ ID NO: 90; and the CDR3 comprises the amino acid sequence of SEQ ID NO: 91.

49. The IL27Rα binding protein of claim 48, wherein the single domain antibody comprises the amino acid sequence of SEQ ID NO: 23.

50. The IL27Rα binding protein of claim 1, wherein the CDR1 comprises the amino acid sequence of SEQ ID NO: 92; the CDR2 comprises the amino acid sequence of SEQ ID NO: 93; and the CDR3 comprises the amino acid sequence of SEQ ID NO: 94.

51. The IL27Rα binding protein of claim 50, wherein the single domain antibody comprises the amino acid sequence of SEQ ID NO: 24.

52. The IL27Rα binding protein of claim 1, wherein the CDR1 comprises the amino acid sequence of SEQ ID NO: 95; the CDR2 comprises the amino acid sequence of SEQ ID NO: 96; and the CDR3 comprises the amino acid sequence of SEQ ID NO: 97.

53. The IL27Rα binding protein of claim 52, wherein the single domain antibody comprises the amino acid sequence of SEQ ID NO: 25.

\* \* \* \* \*